US008252742B2

(12) United States Patent  (10) Patent No.: US 8,252,742 B2
Yamka et al.  (45) Date of Patent: *Aug. 28, 2012

(54) METHODS FOR ENHANCING THE QUALITY OF LIFE OF A SENIOR ANIMAL

(75) Inventors: Ryan Michael Yamka, Topeka, KS (US); Kim Gene Friesen, Carthage, IN (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 905 days.

This patent is subject to a terminal disclaimer.

(21) Appl. No.: 12/176,331

(22) Filed: Jul. 18, 2008

(65) Prior Publication Data

US 2009/0111877 A1  Apr. 30, 2009

Related U.S. Application Data

(63) Continuation-in-part of application No. 11/813,276, filed as application No. PCT/US2005/047461 on Dec. 30, 2005, now Pat. No. 8,148,325.

(60) Provisional application No. 60/640,890, filed on Dec. 30, 2004.

(51) Int. Cl.
*A61K 38/00* (2006.01)
*A61K 31/34* (2006.01)
*A61K 31/20* (2006.01)
*A23K 1/00* (2006.01)

(52) U.S. Cl. .......... 514/5.5; 514/474; 514/560; 426/635

(58) Field of Classification Search ................. 426/635; 514/5.5, 474, 549, 560
See application file for complete search history.

(56) References Cited

U.S. PATENT DOCUMENTS

| | | |
|---|---|---|
| 2,980,716 A | 4/1961 | Reed |
| 3,202,514 A | 8/1965 | Burgess |
| 3,946,123 A | 3/1976 | Hanna |
| 4,053,647 A | 10/1977 | Prussin |
| 4,247,562 A | 1/1981 | Bernotavicz |
| 4,898,890 A | 2/1990 | Sato et al. |
| 4,997,671 A | 3/1991 | Spanier |
| 4,997,672 A | 3/1991 | DeSimone |
| 5,004,624 A | 4/1991 | Koschak et al. |
| 5,030,458 A | 7/1991 | Shug et al. |
| 5,114,704 A | 5/1992 | Spanier et al. |
| 5,118,505 A | 6/1992 | Koltringer |
| 5,292,538 A | 3/1994 | Paul et al. |
| 5,339,771 A | 8/1994 | Axelrod |
| 5,419,283 A | 5/1995 | Leo |
| 5,455,264 A | 10/1995 | Beisswenger et al. |
| 5,532,010 A | 7/1996 | Spanier et al. |
| 5,569,670 A | 10/1996 | Weischer et al. |
| 5,599,835 A | 2/1997 | Fischer |
| 5,621,117 A | 4/1997 | Bethge et al. |
| 5,624,896 A | 4/1997 | Axworthy |
| 5,723,441 A | 3/1998 | Higley et al. |
| 5,728,735 A | 3/1998 | Ulrich et al. |
| 5,730,988 A | 3/1998 | Womack |
| 5,756,088 A | 5/1998 | Matsuura et al. |
| 5,851,573 A | 12/1998 | Lepine et al. |
| 5,858,024 A | 1/1999 | De Lacharriere et al. |
| 5,883,083 A | 3/1999 | Harless |
| 5,916,912 A | 6/1999 | Ames et al. |
| 5,932,257 A | 8/1999 | Wright et al. |
| 5,976,548 A | 11/1999 | Hsia et al. |
| 5,976,568 A | 11/1999 | Riley |
| 5,977,162 A | 11/1999 | Seidman |
| 5,981,767 A | 11/1999 | Tanner et al. |
| 5,994,393 A | 11/1999 | Beisswenger et al. |
| 6,039,952 A | 3/2000 | Sunvold et al. |
| 6,080,788 A | 6/2000 | Sole et al. |
| 6,090,414 A | 7/2000 | Passwater |
| 6,117,477 A | 9/2000 | Paluch |
| 6,133,323 A | 10/2000 | Hayek |
| 6,136,339 A | 10/2000 | Gardiner |
| 6,136,859 A | 10/2000 | Hienriksen |
| 6,184,227 B1 | 2/2001 | Karmali |
| 6,190,591 B1 | 2/2001 | Van Lengerich |
| 6,194,454 B1 | 2/2001 | Dow |
| 6,197,340 B1 | 3/2001 | Byrd et al. |
| 6,232,346 B1 | 5/2001 | Sole et al. |
| 6,264,994 B1 | 7/2001 | Castillo et al. |
| 6,277,842 B1 | 8/2001 | Carthron |
| 6,306,392 B1 | 10/2001 | Cavazza |

(Continued)

FOREIGN PATENT DOCUMENTS

CN  1469712  1/2004

(Continued)

OTHER PUBLICATIONS

Hossain, M.S. et al. "Antioxidative effects of docosahexaenoic acid in the cerebrum versus the cerebellum and brainstem of aged hypercholesterolemic rats," Journal of Neurochemistry (1999) pp. 1133-1138, vol. 72. Kearns, R. J., et al., "Effect of age, breed and dietary omega-6 (n-6): omega-3 (n-3) fatty acid ratio on immune function, eicosanoid production and lipid peroxidation in young and aged dogs," Veterinary Immunology and Immunopathology, (1999) pp. 165-183 vol. 69.

Hall, et al. "Dietary (n-30 fatty acids alter plasma fatty acids and leukotriene B synthesis by stimulated neutrophils from healthy geriatric Beagles," Prostaglandins Leukotrienes and Essential Fatty Acids, (2005) pp. 335-341 73:5.

Araujo, Joseph et al. "Assessment of nutritional interventions for modification of age-associated cognitive decline using a canine model of human aging," Age: Journal of the American Aging Association (2005) pp. 27-37, 27:1.

International Search Report PCT/US2009/051114 date of mailing Dec. 1, 2009.

Rogers, Peter J., "A healthy body, a healthy mind: long-term impact of diet on mood and cognitive function," Proceedings of the Nutrition Society (2001) 135-143 vol. 60.

Hornstra, Gerard, et al. "Essential fatty acids in pregnancy and early human development," European Journal of Obstetrics & Gynecology and Reproductive Biology, (1995) 57-62 vol. 61.

(Continued)

*Primary Examiner* — Raymond Henley, III
(74) *Attorney, Agent, or Firm* — Michael F. Morgan

(57) ABSTRACT

Methods for enhancing the quality of life of a senior or super senior animal by feeding the animal a composition comprising at least one omega-3 polyunsaturated fatty acid and various combinations of amino acids, minerals, and antioxidants in amounts effective to enhance alertness, improve vitality, protect cartilage, maintain muscle mass, enhance digestibility, and improve skin and pelage quality. Changes in expression of genes associated with several biological pathways induced in an animal by feeding it said composition are consistent with an enhanced quality of life.

32 Claims, No Drawings

U.S. PATENT DOCUMENTS

| | | |
|---|---|---|
| 6,306,442 B1 | 10/2001 | Sunvold et al. |
| 6,310,090 B1 | 10/2001 | Hayek |
| 6,335,361 B1 | 1/2002 | Hamilton |
| 6,365,211 B1 | 4/2002 | Corrigan |
| 6,365,622 B1 | 4/2002 | Cavazza |
| 6,365,623 B1 | 4/2002 | Perricone |
| 6,379,727 B1 | 4/2002 | Addy |
| 6,426,362 B1 | 7/2002 | Miller et al. |
| 6,441,024 B1 | 8/2002 | Klatt et al. |
| 6,447,989 B1 | 9/2002 | Comper |
| 6,448,287 B1 | 9/2002 | Casciari et al. |
| 6,458,767 B1 | 10/2002 | Murphy-Ullrich et al. |
| 6,479,069 B1 | 11/2002 | Hamilton |
| 6,492,325 B1 | 12/2002 | Cosgrove |
| 6,517,877 B2 | 2/2003 | Gannon |
| 6,572,888 B2 | 6/2003 | Byrd |
| 6,572,899 B1 | 6/2003 | Gorsek |
| 6,589,748 B2 | 7/2003 | Comper |
| 6,596,762 B2 | 7/2003 | Sokol |
| 6,599,876 B2 | 7/2003 | Kojima |
| 6,746,678 B1 | 6/2004 | Shapiro |
| 6,784,159 B2 | 8/2004 | Holub et al. |
| 6,902,739 B2 | 6/2005 | McPeak et al. |
| 6,914,071 B2 | 7/2005 | Zicker et al. |
| 6,974,841 B1 | 12/2005 | Rapisarda |
| 7,202,270 B2 | 4/2007 | Majeed et al. |
| 7,282,225 B1 | 10/2007 | Davis et al. |
| 2001/0043983 A1 | 11/2001 | Hamilton |
| 2001/0044448 A1 | 11/2001 | Dib |
| 2002/0006907 A1 | 1/2002 | Gardiner et al. |
| 2002/0028762 A1 | 3/2002 | Kojima |
| 2002/0052402 A1 | 5/2002 | Zicker et al. |
| 2002/0076469 A1 | 6/2002 | Zicker et al. |
| 2002/0076470 A1 | 6/2002 | Zicker et al. |
| 2002/0110582 A1 | 8/2002 | Place et al. |
| 2002/0115710 A1 | 8/2002 | Zicker et al. |
| 2002/0119182 A1 | 8/2002 | Zicker et al. |
| 2002/0183382 A1 | 12/2002 | Sokol |
| 2003/0000477 A1 | 1/2003 | Abril |
| 2003/0007998 A1 | 1/2003 | Block et al. |
| 2003/0035821 A1 | 2/2003 | Heaton |
| 2003/0044466 A1 | 3/2003 | Markey |
| 2003/0060503 A1 | 3/2003 | Hamilton |
| 2003/0068309 A1 | 4/2003 | DeSimone |
| 2003/0138477 A1 | 7/2003 | Barclay |
| 2003/0194478 A1 | 10/2003 | Davenport et al. |
| 2003/0198730 A1 | 10/2003 | Stewart |
| 2003/0224061 A1 | 12/2003 | Pacioretty |
| 2004/0037944 A1 | 2/2004 | Cupp et al. |
| 2004/0047896 A1 | 3/2004 | Malnoe et al. |
| 2004/0068010 A1 | 4/2004 | Zicker et al. |
| 2004/0105879 A1 | 6/2004 | Heaton et al. |
| 2004/0166157 A1 | 8/2004 | Thombre |
| 2005/0026225 A1 | 2/2005 | Comper |
| 2005/0100617 A1 | 5/2005 | Malnoe et al. |
| 2005/0123628 A1 | 6/2005 | Zabrecky |
| 2005/0232976 A1 | 10/2005 | Zicker et al. |
| 2005/0249787 A1 | 11/2005 | Reynolds et al. |
| 2005/0266051 A1 | 12/2005 | Kelley |
| 2005/0266052 A1 | 12/2005 | Bartlett et al. |
| 2006/0002985 A1 | 1/2006 | Zicker |
| 2006/0134014 A1 | 6/2006 | Scherl et al. |
| 2006/0141011 A1 | 6/2006 | Jewell |
| 2007/0264287 A1 | 11/2007 | Zicker et al. |
| 2008/0038323 A1 | 2/2008 | Zicker et al. |
| 2008/0057039 A1 | 3/2008 | Rogers et al. |
| 2008/0069834 A1 | 3/2008 | Zicker et al. |
| 2008/0206398 A1 | 8/2008 | Yamka |
| 2008/0214653 A1 | 9/2008 | Zicker et al. |
| 2008/0299286 A1 | 12/2008 | Josephson et al. |
| 2008/0317725 A1 | 12/2008 | Baum |
| 2008/0317884 A1 | 12/2008 | Jewell |
| 2009/0004299 A1 | 1/2009 | Wedekind et al. |
| 2009/0047361 A1 | 2/2009 | Jewell |
| 2009/0111877 A1 | 4/2009 | Yamka |
| 2009/0149529 A1 | 6/2009 | Zicker et al. |
| 2009/0155393 A1 | 6/2009 | Zicker et al. |
| 2009/0156658 A1 | 6/2009 | Zicker et al. |
| 2009/0176864 A1 | 7/2009 | Zicker et al. |
| 2009/0182032 A1 | 7/2009 | Zicker et al. |
| 2009/0227665 A1 | 9/2009 | Zicker et al. |
| 2009/0227666 A1 | 9/2009 | Jewell |
| 2010/0076064 A1 | 3/2010 | Zicker et al. |

FOREIGN PATENT DOCUMENTS

| | | |
|---|---|---|
| EP | 0678247 | 10/1995 |
| EP | 1155627 | 11/2001 |
| EP | 1 350 435 A2 | 10/2003 |
| GB | 2027577 | 2/1980 |
| JP | S55-19090 | 2/1980 |
| JP | S57-132849 | 8/1982 |
| JP | H08-38063 | 2/1996 |
| JP | 2003-527124 | 9/2003 |
| JP | 2004-141130 | 5/2004 |
| RU | 2131677 | 6/1999 |
| RU | 2221456 | 1/2004 |
| WO | WO 97/13415 | 4/1997 |
| WO | WO 00/18247 | 4/2000 |
| WO | WO 2004/024930 | 3/2004 |
| WO | WO 2005/051093 | 6/2005 |
| WO | 2006/074089 A2 | 7/2006 |
| WO | WO 2006/074089 | 7/2006 |
| WO | 2007/002837 A2 | 1/2007 |
| WO | WO 2007/002837 | 1/2007 |
| WO | 2007/059439 A1 | 5/2007 |
| WO | WO 2007/059439 | 5/2007 |
| WO | 2009/088433 A1 | 7/2009 |
| WO | WO 2009/088433 | 7/2009 |

OTHER PUBLICATIONS

Hornstra et al., "Essential Fatty Acids in Pregnancy and Early Human Development," European Journal of Obstetrics & Gynecology and Reproductive Biology (1995) pp. 57-62.

Lim et al., "Intakes of Dietary Docosahexaenoic Acid Ethyl Ester and Egg Phosphatidylcholine Improve Maze-Learning Ability in Young and Old Mice," American Society for Nutritional Sciences (2000) 130 pp. 1629-1632.

International Search Report of the International Searching Authority dated May 10, 2007 for International Application No. PCT/US2005/047461.

SEQUENCE LISTING

<160> NUMBER OF SEQ ID NOS: 57

<210> SEQ ID NO 1
<211> LENGTH: 351
<212> TYPE: DNA
<213> ORGANISM: Canis familiaris

<400> SEQUENCE: 1

```
ggagccatgc attttatgac agtcaaacgt gggaaaatat tcttaaggac agaatgggat      60
cctcgctaat gattgaaaca gcaagaaacc cttcatgtcc taaggatgga ggtttgcttc     120
tgaataaccc ttcagcgcta gcaatgcacg agtgcaaatg tctttggcct gacgtcccat     180
tagagtgcat tgtgtccctg gcaccgggc gttatgagag tgatgtgaga aactctgtga      240
catctacaag cttgaaaacc aaactgtcta atgtcattaa cagtgctaca gatacagaag     300
aagtccacgt aatgcttgat ggtcttttac ctcctgacac ctattttaga t              351
```

<210> SEQ ID NO 2
<211> LENGTH: 528
<212> TYPE: DNA
<213> ORGANISM: Canis familiaris

<400> SEQUENCE: 2

```
gtgctgcaat gcaacctgtt agctaacgtg tccactgtgg cagttcccac gcatccctgc      60
cctggaagcc ccacagtgct gactctccat ccctcagatc actttgacta catcagggca     120
gtcattggat ccaagttcat tggaattggt ggagattatg atggggccag acgtttccct     180
caggggctgg aggatgtgtc cacatacccca gttctgatag aggagttgct gaggcgtggc     240
tggagtaggg aagagctcca gggtgtcctt cgaggaaacc tactgcgggt cttttggacag     300 gtggaacagg tacgggaggc aagcaagggg caaaggccct tggaggatga gttcccggat     360
gagcagctga gcagctcttg ccgctccgtt ctctcacgtc tgcatcagac acagtaccct     420
gctccatacc agaaactaac tgagatttca cctgagtggt cccctaaaca gtcattgtca     480
aaatctctcc ccatcatggc cccaggcctc atagttattg ctgcttgt                 528
```

<210> SEQ ID NO 3
<211> LENGTH: 583
<212> TYPE: DNA
<213> ORGANISM: Canis familiaris

<400> SEQUENCE: 3

```
atcgctggct atgagatcat caccaacacg ctctcttttg ccacctacct cctggccacc      60
aaccctgact gccaagagaa gcttctggca gaggtggaca gctttaagga gaaatatacg     120
gcccttgact actgcagcct ccaggaaggc ctgccctacc tggacatggt gattgcggag     180
accttgagga tctacccccc ggctttcagg ttcacacggg aggcggcgcg ggactgcgag     240
```

```
gtgcggggac agcgcatccc cgcgggcgcc gtggtggagg tggccgtggg cgccctgcac      300
cgtgaccctg agtactggcc acaaccggag accttcaacc ccgagaggtt caaggccgag      360
gcgcagcgac gacagcaacc cttcacctac ctgccgttcg gcgcgggccc ccggagctgc      420
ctcggggtgc ggctggggct gctggaggtc aagctgacgc tgctgcaggt cctgcaccag      480
ttccggttcg aggcctgccc ggagacgcag gtaccactgc agctagactc caaatctgcc      540
ctaggtccaa agaatggcat ctacatcaag attgtctccc gct                       583

<210> SEQ ID NO 4
<211> LENGTH: 107
<212> TYPE: DNA
<213> ORGANISM: Canis familiaris

<400> SEQUENCE: 4
gatttggccc gtgaccctcc agcacaatgt tctgcaggtc ctgtttggga tgatatgttt      60
cattggcaag ccacaattat aggacctaat gacagcccat atcaagg                   107

<210> SEQ ID NO 5
<211> LENGTH: 457
<212> TYPE: DNA
<213> ORGANISM: Canis familiaris
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (253)..(253)
<223> OTHER INFORMATION: n is a, c, g, or t

<400> SEQUENCE: 5
ggaatgggct actctactca tgcagncaag caggncctgc atcaggccag tgggaacctg      60
gacgaagccc tgaagattct tctcagcaat cctcagatgt ggtggttaaa tgattcagat      120
cctgaaacga ncaaccagca agaaagtcct tcccaggaaa acattgacca actggtgtac      180
atgggcttcg acgctgtggt ggctgatgct gccttgagag tgttcagggg aaacgtgcag      240
ctggcagctc agncccctcgc ccacaacgga ggaactcttc ctcctgacct gcagctcttg      300
gtggaagact cttcatcaac gccatccacg tcccccttccg actccgcagg tacctctagt      360
gcctcaacag atgaagatat ggaaaccgaa gctgtcaatg aaatactgga agatattcca      420
gaacatgaag aagattatct tgactcaaca ctggaag                              457

<210> SEQ ID NO 6
<211> LENGTH: 93
<212> TYPE: DNA
<213> ORGANISM: Canis familiaris

<400> SEQUENCE: 6
gagatggagt cctgagcacc tggtttctgt tttgttgatc ccacttcact gtgagggaa      60 ggcctttca tgggaactct ccaaatatca ttc                                   93

<210> SEQ ID NO 7
<211> LENGTH: 374
```

```
<212> TYPE: DNA
<213> ORGANISM: Canis familiaris
<220> FEATURE:
<221> NAME/KEY: misc_feature
<222> LOCATION: (349)..(349)
<223> OTHER INFORMATION: n is a, c, g, or t

<400> SEQUENCE: 7
gtagttgatt cctggttcgc ctttcctctt gggtcccata ggttcgaatc cccttctacc     60
tcagtcggga gtactgtcct ccatggtgct tcccttcctc tccttaatgt ggggaagacc    120
atggggcaat gcatggcgca ggacctgcct cccccaaaag cagtctactt gctccacgga    180
gagagaactg ggtccacgtg ccagagtctt gcccttggc ccagagtagc ctggtcttca    240
tggctgtatg ggagacaagt gccttctctg cttcttgttg taggtgatgc taatctcctt    300
aaccaaacct ttgtcccagc cgctaatctg ttctaactct ccctcctcnt gattctcctg    360
ctcaaagtct gttc                                                     374

<210> SEQ ID NO 8
<211> LENGTH: 500
<212> TYPE: DNA
<213> ORGANISM: Canis familiaris

<400> SEQUENCE: 8
agatgttcaa gggtttcagc gccttgggga atgcctcgga catccgcttc gtcgacaccc     60
ccgccctgga gagcgtctgc ggatacttgc acaggtccca gaaccgcagc gaggagtttc    120
tggtcgccgg aaacctgcgg gacggacact tgcagatcaa cacctgcagt ttcgtggccc    180
cgtggagcag cctgagtacc gctcagcgcc ggggcttcac caagacctat gctgctggct    240
gtgaggggtg cacagtgttt acctgttcat ccatcccctg caaactgcag agtgacactc    300
actgcttgtg gacggaccag ttcctcacag gctctgacaa gggtttccag agccgccacc    360
tggcctgcct gccaagagag ccagggatat gcacctggca gtccctgcgg ccccggatgg    420
cctaaatcct actccccgtg gaagccaaag cctgcacagt gttcacccca cttcccactc    480
ctgtctttct ttatccaaaa                                                500

<210> SEQ ID NO 9
<211> LENGTH: 300
<212> TYPE: DNA
<213> ORGANISM: Canis familiaris

<400> SEQUENCE: 9
gaagtggagt aggtgccgct gttgctgctg gtgttgaatt cagaactgta gcgggacatg     60
gggctggagg acgagcaaaa gatgctgacc gggtccggag atcccaagga ggatccccta    120
acaacagtga gagagcaatg cgagcagctg gagaaatgtg taaaggctcg ggagcggcta    180
gagctctgtg accagcgtgt atcctccagg tcacagacag aggaggattg cacagaggag    240
ctctttgact tcctgcatgc aagggaccac tgtgtggccc acaaactctt taacagcttg    300

<210> SEQ ID NO 10
<211> LENGTH: 560
<212> TYPE: DNA
<213> ORGANISM: Canis familiaris

<400> SEQUENCE: 10
tgtgggtccg agctaacagc tacgtggggc ctctgatggc aggacggcgg ccctctgccc     60
tgagcctggg tcgtgggcag gacctgctag gtacggtggg cgttaggtac tccagccaca    120
gcctctgagg cgacggtggg cagtttgggg accttgagag gctgtgatgg gccctcctat    180
```

-continued

```
caggatcttg ctgggggtgg gtgggcaggg agcacaggat tggggggagg ccttaagcac    240
cttttctggg tcagaagcct cctctccgca ttgcatgtgc aacctcagtg aagcagcatg    300
ggcaggggag ccggacgggc acccaacag agctccttat gctgcaggag gggttcacag    360
accactcgga catcaccatc accttggggg gggtgcttga gggaaaagca aattgaacag    420
agcgtgattc tcacgtgcag gtacctaagg gaactgggga agagatgcac caagacgaga    480
gccctcgtca tccctgggga gcccaagcct aggggttttc ttcctcttcc cgtttagcat    540
tttccaccat cgtatgttac                                                560
```

<210> SEQ ID NO 11
<211> LENGTH: 546
<212> TYPE: DNA
<213> ORGANISM: Canis familiaris

<400> SEQUENCE: 11

```
agttttgacc aattcgctct gtacaaggag ggggacactg agccccacaa gcaatctgca     60
gaacagtact gggccaattt ccccatcacc gcagtgactg ttgcccacag tgggatctac    120
cgatgctata gcttttccag caagttcccg tacctgtggt cagcccccag cgaccccctg    180
gagcttgtgg taacaggtga gggagatgca gtccaagcct ttcttcttca gctcttgcat    240
actctggtgg aagttccagg ggaggggcca acagtgcctt ctaggactat cactgtctct    300
ccaaaggggt cagactctcc aactggtctt gctcaccagc actacaccaa gggcaatctg    360
gtccggatat gccttggagc tgtgattcta atactcctgg tgggaattct ggcagaagat    420
tggcacagca gaaagaaacc cctgttgctc cgggtcagag ctgtccacag gccactccca    480
cccctcccac agacccagaa accacacagt catcaggatg ggggtcgacc agatggccat    540
aaccat                                                               546
```

<210> SEQ ID NO 12
<211> LENGTH: 406
<212> TYPE: DNA
<213> ORGANISM: Canis familiaris

<400> SEQUENCE: 12

```
tctgggctgc cacggaggcc accaacgact gccccgcaga gtgcacctgc cagaccctgg     60
agaccatggg gctgtgggtg gactgcaggg ggcggggact caaggccctg cccgccctgc    120
cggtccacac ccgccacctc ctgctggcca ataacagcct ccgctccgtg cccccctggtg   180 ccttcgacca cctgcctggg ctgcagatcc tcgacgtgat gcacaacccc tggcactgtg    240
actgcagcct cacctacctg cgtctctggc tggaggacca cacgcccgag gccttgctgc    300
aggtccgctg tgccagcccc gcgctggcca ccacccggcc gctgggctgg ctgacgggct    360
acgagctggg cagctgcggc tggcagctac aggcaccctg gaccta                   406
```

<210> SEQ ID NO 13
<211> LENGTH: 501
<212> TYPE: DNA
<213> ORGANISM: Canis familiaris
<220> FEATURE:
<221> NAME/KEY: misc_feature
<222> LOCATION: (403)..(403)
<223> OTHER INFORMATION: n is a, c, g, or t

<400> SEQUENCE: 13

```
atctctcagg caacatcgtc ttctacaccg gggtctccaa gacggaattc aagaaggaga     60
catttgaagt gacactggag cccttgtctt tcaagagaga ggaggtgctg atcagagcgg    120
```

```
gcgagtacat gggccagctg ctagagcaag catacctgca cttctttgtc acagcgcgtg    180
tcaatgagtc caaggatatt ctggccaagc agaagtccac cgtgctgacg atccccagc    240 tcatcatcaa ggtccgtggc gccaagatgg ttggttctga catggtggtg acagttgagt    300
tcaccaatcc cctgaaagaa actctgcgga atgtgtggat acacctggat ggtcctggag    360
tgataaagcc aatgaggaag atgttccgtg aaatccagcc cantgccacc atacaatggg    420
aagaagtgtg tcgaccctgg gtgtctggcc ctcggaagct gatagccagc atgacgagtg    480
actccctgag acacgtgtat g                                              501

<210> SEQ ID NO 14
<211> LENGTH: 294
<212> TYPE: DNA
<213> ORGANISM: Canis familiaris

<400> SEQUENCE: 14
ggcaacatgt cgtccatgga ggtcaacatc gacatgctgg agcagatgga cctgatggac     60
atctctgacc aggaggccct ggacgtcttc ctgaactccg gcgctgaaga caacacggtg    120
ccgtctccgg tctcagggcc tggctcgggg acagtcggc aggaaatcac gctccgggtt    180
ccagatcccg ccgaatcgca agctgagcct cctccctcgc cgtgtgcctg tcctgagctg    240
gccgccccgg cccccggcga cggtgaggcc cccgtggtcc agtctgacga ggag          294

<210> SEQ ID NO 15
<211> LENGTH: 330
<212> TYPE: DNA
<213> ORGANISM: Canis familiaris
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (248)..(248)
<223> OTHER INFORMATION: n is a, c, g, or t

<400> SEQUENCE: 15
attacaacgt gactctggct ttggtccctg tcctggatga cggctggtgc aaagagagga     60
ccctagacna accagctgct gttcttcctg gtggaggagg aaccggagg catggttgtg    120 ttgacagtga daccccaaga gagaggcgcg gatcacaccc aggccatcgt gctgggctgt    180 gtaggggca tcgtggcagt ggggctgggg ctggtcctgg cttaccggct ctctgtggaa    240
atctacgncc gccgagaatt tagccgcttt gagaaggagc agaagcacct caactggaag    300
caggaaaaca atcctctcta cagaagcgcc                                    330

<210> SEQ ID NO 16
<211> LENGTH: 395
<212> TYPE: DNA
<213> ORGANISM: Canis familiaris

<400> SEQUENCE: 16
tgggcgcatg tatgcacctg cctgggtggc ccctgaagct ctgcagaaga agcctgaaga     60
tacaaacaga cgctcagcag atatgtggag ttttgcagtg cttctgtggg aactggtgac    120
gagggaggta cccttgctg acctctccaa catggagatt ggaatgaagg tggcactgga    180
aggccttcgg cctactatcc caccaggcat ttcccccccat gtgtgtaagc tcatgaagat    240
```

```
ctgcatgaat gaagaccctg ctaagcggcc caagtttgac atgattgtgc ctatcctgga    300
gaagatgcag gacaagtaga gctggaaagc ccttgcctaa actccagagg tgtcaggaca    360
cggttagggg agtgtgtctc cccaaagcag caggc                               395
```

<210> SEQ ID NO 17
<211> LENGTH: 248
<212> TYPE: DNA
<213> ORGANISM: Canis familiaris
<220> FEATURE:
<221> NAME/KEY: misc_feature
<222> LOCATION: (182)..(186)
<223> OTHER INFORMATION: n is a, c, g, or t
<220> FEATURE:
<221> NAME/KEY: misc_feature
<222> LOCATION: (200)..(205)
<223> OTHER INFORMATION: n is a, c, g, or t

<400> SEQUENCE: 17

```
atacgaatgc agagattcct aatcaaactg ttgatcaaaa gactgatcct aaccaatgct     60
ggtgttgcac cttctggaac cacgggctta agaaaacccc caggatcact cctccctgcc    120
ttttctctgc ttgcatatca ttgtggacac ctagaatacg ggacttgcct cgagaccatg    180
cnnnnntcca aatcagactn nnnnngtagc ctctgaacgc gaagagaatc ttccaagagc    240
atgaacag                                                             248
```

<210> SEQ ID NO 18
<211> LENGTH: 453
<212> TYPE: DNA
<213> ORGANISM: Canis familiaris

<400> SEQUENCE: 18

```
gaagcccttg atggatactg tgaacgggaa caggctataa agacccacca ccactcctgt     60
tgccaccacc ctcctagccc tgcccgcgat gagtgctttg cccgtcaggc gccataccccc   120 aactatgacc gggacatcct gacccttgat ttcagccaag ttaccccccaa cctcatgcaa   180 catctctgtg gaaatggaag acttctcacc aagcataaac agattcctgg gctgatccgg    240
aacatgactg cccactgctg tgacctgcca tttccagagc aggcctgctg tgctgaggag    300
gagaaatcgg ccttcattgc agacttgtgt ggttcccgac gtaacttctg gcgagactct    360
gccctctgct gtaacctgaa tcctggagat gaacagacca actgcttcaa cacttattat    420
ctgaggaatg tggctctagt ggctggagac aat                                 453
```

<210> SEQ ID NO 19
<211> LENGTH: 535
<212> TYPE: DNA
<213> ORGANISM: Canis familiaris

<400> SEQUENCE: 19

```
tggttgtagc tcctcacttg tccaagaccg aagcagcaac caaactgaac ttagcctttg     60
ggctgctctt ggtagtcaca gaaatgccca cgcttcagtc ccctgggctt ccaatgcttc    120
tggacctctg aaccagcctg tgatgtccaa ggaaccccac gtcacgctcc aggctgctgc    180
tggtctgtct cccccacaag cttctcaaag tctggtagat tatgacagct ctgatgattc    240
tgaagtagaa gtcacagacc agcactcaac aaacagtaaa caaacatctt tacagcaaga    300
agcaaagaag aaatttcagg acacagttag aacaggtcca gatgaaaaag aacttagcat    360
ggagcctcaa tcaaggcctc tggttccaga acaatctaat attaatattc ccttctctgt    420
tgactgtgac atctccaaag taggaatatc ttacaggaca ctgaagtgct ttcaggagct    480
```

```
acagggtgcc atttaccgtt tgcagaaaaa aaatctttc ccctataatg ccaca         535

<210> SEQ ID NO 20
<211> LENGTH: 264
<212> TYPE: DNA
<213> ORGANISM: Canis familiaris

<400> SEQUENCE: 20
gcggactgtg ttccaacccc ttcagccgac ttgccccctc cgtcccttct cttaagagac   60 ccatccctg gccccccacc ccaccctcac ccagacctgc gggtccctca gagggggtc    120 aggcctcttt ctctttcacc ttcatttgct ggcgtgagct gcggggtgt gtgtttgtat   180 gtggggagta ggtgtttgag gttcccgttc tttcccttcc caagtctctg ggggtggaaa  240
ggaggaagag atattagtta caga                                         264

<210> SEQ ID NO 21
<211> LENGTH: 156
<212> TYPE: DNA
<213> ORGANISM: Canis familiaris
<220> FEATURE:
<221> NAME/KEY: misc_feature
<222> LOCATION: (72)..(77)
<223> OTHER INFORMATION: n is a, c, g, or t
<220> FEATURE:
<221> NAME/KEY: misc_feature
<222> LOCATION: (79)..(83)
<223> OTHER INFORMATION: n is a, c, g, or t
<220> FEATURE:
<221> NAME/KEY: misc_feature
<222> LOCATION: (85)..(89)
<223> OTHER INFORMATION: n is a, c, g, or t

<400> SEQUENCE: 21
aggtcccgta acaccggcat cgcgaccgca cagcgccatc tccccagaat aaagcccagt   60
aaacacccct gnnnnnnann nnnannnnnc accacgtttt gctatcagaa ctctccttgt  120
ttccagagcc cgtgtgcttt tgtttgcccc agcccc                            156

<210> SEQ ID NO 22
<211> LENGTH: 295
<212> TYPE: DNA
<213> ORGANISM: Canis familiaris
<220> FEATURE:
<221> NAME/KEY: misc_feature
<222> LOCATION: (134)..(137)
<223> OTHER INFORMATION: n is a, c, g, or t
<220> FEATURE:
<221> NAME/KEY: misc_feature
<222> LOCATION: (140)..(140)
<223> OTHER INFORMATION: n is a, c, g, or t

<400> SEQUENCE: 22
ccacccatgg tgacgatgac acacatcctg gtggcatgcg tgtgttggtt tagcgttgtc   60
tgcgttgtac tagagcgaaa atgggtgtca ggcttgtcac cattcacaca gaaatttaaa  120
aaaaaaaaaa aaannnngan aaaaaacctt taccaaggga gcatctttgg actctctgtt  180
tttaaaacct cctgaaccat gacttggagc cagcagatta ggctgtggct gtggacttca  240
gcacaaccat caacattgct gatcaagaaa ttacaatata cgtccattcc aagtt        295

<210> SEQ ID NO 23
<211> LENGTH: 502
<212> TYPE: DNA
<213> ORGANISM: Canis familiaris
<220> FEATURE:
<221> NAME/KEY: misc_feature
```

```
<222> LOCATION: (51)..(51)
<223> OTHER INFORMATION: n is a, c, g, or t
<220> FEATURE:
<221> NAME/KEY: misc_feature
<222> LOCATION: (457)..(457)
<223> OTHER INFORMATION: n is a, c, g, or t

<400> SEQUENCE: 23
atacctcaga ggtctcgtag ctcgtgccct tgccatccag agctgggtgg nagagagctg      60
agaagcaggc tcttttctct gatacactcg acctgtcaga actcttccac ccagacacat     120
ttctcaatgc tcttcgccag gaaacagcaa gggtgatggg ctgctctgtg gatagcctta    180
agtttgtagc ttcgtggaaa ggtcggctgc aagaagcaaa gctgcagatc aagatgggcg     240
gcttgcttct ggaaggctgc agttttgacg ggagccggct ctctgaaaac caccacgatt     300
ctccaagtgt gtcaccagtt ctccttgct gtgttggctg gattcccag ggtgcatatg      360 gtccctattc tcctgacgag tgcatatctc tgcccgtgta cacgagcgct gagagggatc     420
gtgtggtagc caacatcgac gtcccgtgtg ggggcancca agaccagtgg attcagtgtg     480
gagccgctct gtttctaaaa aa                                              502

<210> SEQ ID NO 24
<211> LENGTH: 147
<212> TYPE: DNA
<213> ORGANISM: Canis familiaris

<400> SEQUENCE: 24
aggacgacaa ggctcaggac gcaaagtgtg aaactgcctt tgtaacaggg cagaagcagc      60
tctgtattgg attcacaacc tacctatctg cattcaggtg gggctcggag gtcagaggtc     120
tggctacttg aggtttgctg tttgcac                                         147

<210> SEQ ID NO 25
<211> LENGTH: 371
<212> TYPE: DNA
<213> ORGANISM: Canis familiaris
<220> FEATURE:
<221> NAME/KEY: misc_feature
<222> LOCATION: (91)..(91)
<223> OTHER INFORMATION: n is a, c, g, or t

<400> SEQUENCE: 25
agccacagca tttcctttta acttggttca attttgtag caagactgag cagttctaaa       60
tcctttgcgt gcatgcatac ctcatcagtg nactgtacat accttgccct ctcccagaga    120
cagctgtgct cacctcttcc tgctttgtgc cttgactaag gcttttgacc ctaaatttct    180
gaagcacagc caagataaag tacattcctt aattgtcagt gtaaattacc tttattgtgt    240
gtacattttt actgtacttg agacattttt tgtgtgtgac tagttaattt tgcaggatgt    300
gccatatcat tgaatggaac taaagtctgt gacagtggac atagctgctg gaccattcca    360
tcttacatgt a                                                          371

<210> SEQ ID NO 26
<211> LENGTH: 205
<212> TYPE: DNA
<213> ORGANISM: Canis familiaris

<400> SEQUENCE: 26
ggtgctactg tttgaaacag ctctactctc ctccggcttc tcactggagg atccccagac      60
tcactccaac cgcatttacc gcatgataaa gctaggcctg gcatcgatg aagatgaagt     120 ggcagcggag gaacccagtg ctgctgttcc tgatgagatc cctccacttg agggtgatga    180
```

```
ggatgcctct cgcatggaag aagtc                                         205

<210> SEQ ID NO 27
<211> LENGTH: 256
<212> TYPE: DNA
<213> ORGANISM: Canis familiaris

<400> SEQUENCE: 27
gacatcacca gtggagacgg caccggcggt ataagcattt atggtgagac gtttccagat    60
gaaaacttca aactgaagca ttatggcatt ggttgggtca gcatggccaa cgctgggcct   120
gacaccaacg gctctcagtt ctttatcacc ttgaccaagc ccacttggtt ggatggcaaa   180
catgtggtat ttggaaaagt ccttgatgga atgactgtgg tccactccat agaacttcag   240
gcaaccgatg ggcacg                                                   256

<210> SEQ ID NO 28
<211> LENGTH: 343
<212> TYPE: DNA
<213> ORGANISM: Canis familiaris
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (161)..(161)
<223> OTHER INFORMATION: n is a, c, g, or t
<220> FEATURE:
<221> NAME/KEY: misc_feature
<222> LOCATION: (314)..(315)
<223> OTHER INFORMATION: n is a, c, g, or t

<400> SEQUENCE: 28
gaattaacaa tctgcttgag ccccaaaaca ctacttatgc acttcacttg ccaaaagatt    60
tgngcaaggt tttgtaccct ggtaaatgat gccaaagttt gttttctgtg gtgtttgtca   120
aatgttctat gtataattga ctgtctgtaa catgctgttt ncttcctctg cagatgtagc   180
tgctttccta aatctgtctg tctttcttta ggttagctgt atgtctgtaa aagtatgtta   240
aattaaatta ctctatcaga cgcttgtctg tcttttgatg tagaagcaac tttgtagcac   300
cttgttttga ggtnngctgc atttgttgct gtactttgtg cat                     343

<210> SEQ ID NO 29
<211> LENGTH: 566
<212> TYPE: DNA
<213> ORGANISM: Canis familiaris
<220> FEATURE:
<221> NAME/KEY: misc_feature
<222> LOCATION: (139)..(139)
<223> OTHER INFORMATION: n is a, c, g, or t
<220> FEATURE:
<221> NAME/KEY: misc_feature
<222> LOCATION: (394)..(394)
<223> OTHER INFORMATION: n is a, c, g, or t

<400> SEQUENCE: 29
ttcagttcct gtctcatggc cgctcccggg accatgccat cgccgccact gccttctcct    60
gcatcgcttg tgtggcttat gccaccgaag tggcctggac ccgggcccgt cccggagaga   120
tcaccggcta catggccant gtgccgggcc tgctcaaggt gctggagacc tttgtggcct   180
gcatcatctt cgccttcatc agcaaccccc ccctgtacca gcaccagccg gccctggagt   240
ggtgtgtggc cgtctactcc atctgttcca tcctggcggc tgtggccatc ctactgaacc   300
tgggggactg caccaacatg ctgcccatct ccttccccag tttcctgtcg ggcctggccc   360
```

```
tgctctccgt cctgctgtat gccacggctc tggntctctg gccgctctac cagttcaacg      420
agaagtatgg tggccagccc cgtcggtcga gggatgttag ctgcgccgac aggcacacct      480
actacgtgtg tacctgggac cgccgcctgg ctgtggccat cctgacagcc atcaacctgc      540
tggcttacgt ggctgacctg gtgtac                                          566

<210> SEQ ID NO 30
<211> LENGTH: 93
<212> TYPE: DNA
<213> ORGANISM: Canis familiaris

<400> SEQUENCE: 30
ggagcagtca gaactaagac atggtccgtt ttactatatg aagcagccac tcaccacaga       60
ccctgttgat gttgtaccgc aggatggacg gaa                                   93

<210> SEQ ID NO 31
<211> LENGTH: 42
<212> TYPE: DNA
<213> ORGANISM: Canis familiaris

<400> SEQUENCE: 31
cctcttcttc ggatgttttc cttcaaggcc cctaccattg at                         42

<210> SEQ ID NO 32
<211> LENGTH: 336
<212> TYPE: DNA
<213> ORGANISM: Canis familiaris

<400> SEQUENCE: 32
ggtgctgttc accacagtaa gtggcctctc agtgttgctg accaaagtgt gaaatcctag       60
agcttcaggg gagaggacgt gggggaaatc cggggcttga cttttataata ggattataga     120 gatgaaaagt acaccttgct ttaggcaaca gttgggattc ctaagacgca tgtgtaagag     180
catatgtgaa atcccttccc cattgttgat ctctactcac agaattttgt ctttattatg     240
gtgtaagaat cactcttaaa gccacatatt caattcaaag caaatacgtg ttctgcagtt     300
gcaaatgtgt atttaattct tcacaattcc tgtaag                                336

<210> SEQ ID NO 33
<211> LENGTH: 406
<212> TYPE: DNA
<213> ORGANISM: Canis familiaris

<400> SEQUENCE: 33
gaaactcggt ctggtgttcg atgacgtcgt gggcattgtg gagataatca atagtaggga       60
tgtcaaagtt caggtaatgg gtaaagtgcc aaccatttcc atcaacaaaa cagatggctg     120
ccatgtttac ctgagcaaga attccctgga ttgcgaaata gtcagtgcca atcttctga      180 gatgaatgtc ctcattccta ctgaaggcgg tgactataat gaattcccag tccctgagca     240
gttcaagacc ctatggaatg ggcagaagtt ggtcaccaca gtgacagaaa ttgctggata     300
agcgaagtgc cactgggttc tttgccctcc ccctcacacc atgggataaa tctatcagga     360
cggttctttt ctagatttcc tttacctttc tgctcttaaa ctgctt                     406

<210> SEQ ID NO 34
<211> LENGTH: 321
<212> TYPE: DNA
<213> ORGANISM: Canis familiaris

<400> SEQUENCE: 34
```

```
aaatcttacg aagcccaata tgcagggagt taactgaaaa ctatcttggc agtgaggttg      60
gcactgttga taaagctggt cccttccttt aactgtcttt taggttgttc ttgccttgtt     120
gccaggagta ttgcaggtaa tacagtatat tcataagaat atcaatcttg ggctaaaat      180 gccttgattc tttgcacctc ttttacaagt ccttacgttg aattactaat tgataagcag     240
cagcttccta catatagtag gagactgcca cgttttgct atcatgattg gctgggcctg      300
ctgctgttcc tagtaaggta t                                               321

<210> SEQ ID NO 35
<211> LENGTH: 524
<212> TYPE: DNA
<213> ORGANISM: Canis familiaris

<400> SEQUENCE: 35
aatggtgcca tcttactgag ggattttgta ggctgtttta tagattttcc taagcctctg      60
gttgcagtga taaatggtcc agccatagga atctccgtca ccattctcgg ctattcgat     120 cttgtgtatg cttccgacag ggcaacattt cacactcctt ttactcacct gggccaaagt    180
ccagaaggat gttcctccta tactttccc aagataatgg gccaagccaa ggcagcagag     240
atgctcatgt ttggaaagaa gttaacagct agagaagcct gtgctcaagg acttgttact    300 gaagttttc ccgatagcac ttttcagaaa gaagtttgga ccaggctgaa agcatattca      360
aaactccccc gaaataccett gcatatttcc aaacagagca tcagaaatct tgagaaagaa    420
aagctacatg ctgttaacgc agaagaaaac agcgtcctcc aggaaaggtg gctgtcagac    480
gaatgcataa atgcagtcat gagcttctta tcccggaagg ccaa                     524

<210> SEQ ID NO 36
<211> LENGTH: 526
<212> TYPE: DNA
<213> ORGANISM: Canis familiaris
<220> FEATURE:
<221> NAME/KEY: misc_feature
<222> LOCATION: (472)..(472)
<223> OTHER INFORMATION: n is a, c, g, or t
<220> FEATURE:
<221> NAME/KEY: misc_feature
<222> LOCATION: (475)..(477)
<223> OTHER INFORMATION: n is a, c, g, or t

<400> SEQUENCE: 36
atgatagttg ccatgccaac cagctccaga attaccgcaa ttatttgttg cctgcagggt      60
acagccttga ggagcaaaga attctggatt ggcaaccccg tgaaaccct ttccacaatc     120 tgaaggtact cttggtgtca gaccaacagc agaacttcct ggagctctgg tctgagatcc     180
tcatgaccgg gggggcagcc tctgtgaagc agcaccattc aagtgccat aacaaagata     240 ttgctttagg ggtattttgac gtggtggtga cggatccctc atgcccagcc tcggtgctga    300
agtgtgctga agcattgcag ctgcctgtgg tgtcacaaga gtgggtgatc cagtgcctca    360
ttgttgggga gagaattgga ttcaagcagc atccaaaata caaacatgat tatgtttctc    420
actaatactt ggtcttaact gatttttattc cctgctgttg tggagattgt gnttnnncca   480
ggttttaaat gtgtcttgtg tgtaactgga ttccttgcat ggatct                   526

<210> SEQ ID NO 37
<211> LENGTH: 333
<212> TYPE: DNA
<213> ORGANISM: Canis familiaris

<400> SEQUENCE: 37
```

-continued

```
ggcccaccag ctctgagcag atcatgaaga cagggggccct tttgcttcag ggtttcatcc    60
aagatcgagc agggcgaatg ggggagagaa cacctgagct gcccttggag caggtgcccc   120
aggatgcatc caccaagaag ctgagcgaat gtctcaagcg catcggagat gaactggaca   180
gtaacatgga gttgcagagg atgatcgcag ctgtggacac agactctccc cgtgaggtct   240
tcttccgagt ggcagctgag atgttttctg atggcaactt caactggggc cgggttgttg   300
ccctcttcta ctttgccagc aaactggtgc tca                                333
```

<210> SEQ ID NO 38
<211> LENGTH: 454
<212> TYPE: DNA
<213> ORGANISM: Canis familiaris
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (353)..(353)
<223> OTHER INFORMATION: n is a, c, g, or t
<220> FEATURE:
<221> NAME/KEY: misc_feature
<222> LOCATION: (379)..(379)
<223> OTHER INFORMATION: n is a, c, g, or t

<400> SEQUENCE: 38

```
gaaagttcac cactgcatgt tttatgatca gataactcat tgaaatgagt ctttgctctt    60
tagactaaat tcccacctag tactgccatt aaaatgaatt tgccagctgg tgtgcatact   120
ggaaatgaaa agatactgaa agaatggaac gaatggtgag cttaactcag tggcactgtc   180
atactgaaaa aatacagtaa aatcataaaa acagatctgc cagctgatgt ttttattctc   240
agaaacagca ttgttgataa tattttagta tacagagcta ctgtacaatt tttaccttgn   300
aaacatgact gtggttttgt atttgtgttg acttttagggg ttgggataaa atncagtata   360
atatatacct tatcaaacnt tttctttgag ctcttactaa aaatatggca tgcataagat   420
tgttcagaag agtagactgt taacctagtt tgta                               454
```

<210> SEQ ID NO 39
<211> LENGTH: 314
<212> TYPE: DNA
<213> ORGANISM: Canis familiaris
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t

<400> SEQUENCE: 39

```
cttccagagc tgaagctggc cattgatcna aattgacaat ggcttcttct ctcccaagca    60
gcctgncctc ttcaaagatt taatcaatat gctattttat catgacaggt ttaaagtctt   120
cgcagactat gaagcctatg tcaagtgtca agaaaaagtc agccagctgt acatgaatcc   180
aaaggcctgg aacacaatgg tactcaaaaa catagctgcc gcagggaagt tctctagtga   240
ccgaacaatt aaggaatatg ccagggacat ctgaacatg gaaccttcag atctcaagat   300
ttccctatcc aatg                                                    314
```

<210> SEQ ID NO 40
<211> LENGTH: 397

```
<212> TYPE: DNA
<213> ORGANISM: Canis familiaris
<220> FEATURE:
<221> NAME/KEY: misc_feature
<222> LOCATION: (311)..(311)
<223> OTHER INFORMATION: n is a, c, g, or t

<400> SEQUENCE: 40
gactccaccg gaggcaattg cactgtgtag ccgtctgctg gagtatacac caactgcccg      60
attgacacca ctggaagctt gtgcacattc atttttgat gaattaaggg acccaaatgt     120
caaactacca aatgggcgag acacacctgc actcttcaac ttcaccactc aagaactgtc    180
aagtaatcca cctctagcta ccatccttat tcctcctcat gctcggattc aagcagctgc    240
ttcaacccct acaaatgcca cagcagcctc agatgctaat gccggagacc gtggacagac    300
gaacaatgcc ncttctgcat cagcttctaa ctccacctga acagtcccga gcagccagct    360
gcacaggaag aaccaccagt tacttgagtg tcactca                             397

<210> SEQ ID NO 41
<211> LENGTH: 498
<212> TYPE: DNA
<213> ORGANISM: Canis familiaris
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t

<400> SEQUENCE: 41
taatgactgc caactcactg tttgttggag ttatatgcag aaataaagnc caagtcttca      60
gaaacaggct tcaggatgcc ctcaccaggg atggaagagg caggctgcag caaagagatg    120
cagagttccc ttgcacatct cgacttaaat gagtctccca tcaagtcttt tgtttccatt    180
tcagaagcca cagattgctt agtggacttt aaaaagcaac ttaacgttcg gcaaggtagt    240 cggcacacgga ccaaagcagg cagaggaaga aggagaaaac cctgaatttc tagggtccag   300
acacccgaca aaaccattag caatagggggt gggccgtgtc attaagtctt agtggcttct    360
gtttcattgt tgaacaagtt ttttggcccn gcagttttca ccaccagcac caactcagca    420
ttcttgtttt gatgttttct ataagctata cagacaattg tgtatagtat tctgttttat     480
aacagtctgg attcactt                                                   498

<210> SEQ ID NO 42
<211> LENGTH: 83
<212> TYPE: DNA
<213> ORGANISM: Canis familiaris

<400> SEQUENCE: 42
agtggcgctg tgtgctgaaa attggggaac acactccctc agcccttgcg atcatggaaa      60
atgccaacgt tctggcccgt tat                                              83

<210> SEQ ID NO 43
<211> LENGTH: 315
<212> TYPE: DNA
<213> ORGANISM: Canis familiaris

<400> SEQUENCE: 43
agctcactgg catggccttc cgtgtcccca ccccaatgt atcagttgtg gatctgacct       60
gccgcctgga gaaagctgcc aaatatgacg acatcaagaa ggtagtgaag caggcatcgg    120
```
agggacccct caaaggcatc ctgggctaca ctgaggacca ggtggtctcc tgtgacttca 180
acagtgacac ccactcttcc accttcgacg ccggggctgg cattgccctc aatgaccact 240
ttgtcaagct catttcctgg tatgacaatg aatttggcta cagcaaccgg gtggtggacc 300
tcatggtcta catgg 315

<210> SEQ ID NO 44
<211> LENGTH: 536
<212> TYPE: DNA
<213> ORGANISM: Canis familiaris
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (192)..(194)
<223> OTHER INFORMATION: n is a, c, g, or t
<220> FEATURE:
<221> NAME/KEY: misc_feature
<222> LOCATION: (197)..(198)
<223> OTHER INFORMATION: n is a, c, g, or t
<220> FEATURE:
<221> NAME/KEY: misc_feature
<222> LOCATION: (211)..(211)
<223> OTHER INFORMATION: n is a, c, g, or t
<220> FEATURE:
<221> NAME/KEY: misc_feature
<222> LOCATION: (263)..(263)
<223> OTHER INFORMATION: n is a, c, g, or t
<220> FEATURE:
<221> NAME/KEY: misc_feature
<222> LOCATION: (361)..(361)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (380)..(380)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (391)..(391)
<223> OTHER INFORMATION: n is a, c, g, or t
<220> FEATURE:
<221> NAME/KEY: misc_feature
<222> LOCATION: (419)..(419)
<223> OTHER INFORMATION: n is a, c, g, or t
<220> FEATURE:
<221> NAME/KEY: misc_feature
<222> LOCATION: (427)..(427)
<223> OTHER INFORMATION: n is a, c, g, or t
<220> FEATURE:
<221> NAME/KEY: misc_feature
<222> LOCATION: (430)..(430)
<223> OTHER INFORMATION: n is a, c, g, or t
<220> FEATURE:
<221> NAME/KEY: misc_feature
<222> LOCATION: (458)..(458)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t

<400> SEQUENCE: 44

```
gaatgtgttg gcagactgag gcccccatg tttttaatgc gcactgggga caaccatcta    60
aggtctagaa acttttggac cataggaaag ataggtttat ggtcctcttc cagatgcagc   120
cctaggagag cattcccatg gggtctctgg atcccttcn ttgctctgtg aggctctgtg   180 accaccttt gnnntgnngg gggcagggg ncttcctcag ctccgcctcc agtgccccca   240 ggtccccac ggctcacagt ccntgaaaat tcagagctgc cctgtaagga ttttgtccac   300
tgggcaattc agatatactt cgatatccct gagaagaag aggcagcagc aaacactccc   360
nagggcatct gtctcagnan tctctcnttg natgagacag aagcctactt ttcagaaanc   420
ttatcanggn tactttataa gaaactttt tttttttnct aaaatcagac aaaaggtggc   480
ttntgcatat tcttnattaa taactgtgtc tttgtctcct ctgcttaact ttagga       536

<210> SEQ ID NO 45
<211> LENGTH: 483
<212> TYPE: DNA
<213> ORGANISM: Canis familiaris
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (149)..(149)
<223> OTHER INFORMATION: n is a, c, g, or t
<220> FEATURE:
<221> NAME/KEY: misc_feature
<222> LOCATION: (202)..(202)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t

<400> SEQUENCE: 45
ggtacatcac gcctgatcag ctggctgacc tctacaagtc cttcatcagg gactacccag    60
tggtgtctat cgaagacccc ttcgaccagg atgactggga agcttggcag aaattcactg   120
ccagcgctgg aatccaggtg gnggggang atctcaccgt gaccaaccca aagcggattt   180
ccaaggctgt gggcgagaaa tngtgcaact gcctcctgct taaagtgaac cagattggct   240
ctgtgaccga gtctcttcag gcgtgcaagc tggcccagtc caatgggtgg ggcgtcatgg   300
tgtcgcatcg ctccggggag accgaagata ccttcatcgc tgacctggtg gtgggantct   360
gcactgggca gatcaagacg ggtgcaccat gcagatctga gcgcttggcc aagtacaacc   420
agatcctcag aattgaagag gaactgggta gcaaggccaa gttcgccggc agaagcttca   480
gaa                                                                483

<210> SEQ ID NO 46
<211> LENGTH: 349
<212> TYPE: DNA
<213> ORGANISM: Canis familiaris

<400> SEQUENCE: 46
atctgacctg ttactcaagt cgtaatatta aatggcctaa agaaaaaaac atcagtttcc    60
taaagttaca cataggaatg gttcacaaaa ccctgcagct atgtcctgat gctggatgag   120
acctgtcttg tgtagtccta aattggttaa cgtaatatcg gaggcaccac tgccaatgtc   180
atatatgctg cagctactcc ttaaaccaga tgtgtattta ctgtgttttg taacttctga   240
ttccttcatc ccaacatcca acatgcctag gccatctttt cttcttcagt cacatcctgg   300
gatccaatgt ataaattcaa tattgcatgt attgtgcata actcttcta                349
```

<210> SEQ ID NO 47
<211> LENGTH: 532
<212> TYPE: DNA
<213> ORGANISM: Canis familiaris

<400> SEQUENCE: 47

| | | | | | |
|---|---|---|---|---|---|
| agtatgccag | atcggaacct | ttttcccatt | tacagttcat | gttaatccaa | ttttttttat | 60 |
| tatctcactg | gccagttatt | cctttaaaaa | tgaacttcct | tcttttttgat | tccaagctta | 120 |
| tgattttact | gctcattaat | gtgttacaaa | tatgcactta | atgatttcac | agggagataa | 180 |
| aatagtgaag | agagatgggc | tgaggggctg | ttaggacttt | aatgaaacag | atctttcccg | 240 |
| aatatttctc | ccttcacatt | tctcacatta | gatgtttccc | acattgttct | actccacact | 300 |
| ataaataatt | ttaaggccaa | tcttaaaaaa | tggtagttaa | gtgaaggggt | tgtgtttatt | 360 |
| tcactagaaa | tctgataaaa | cgagagatga | catagaaaaa | gttatcattt | ttgttcatac | 420 |
| agatggcttc | taaaaataaa | tcttcaaaac | tgattacttt | taacctccac | ctcccaaaat | 480 |
| gaaacatccc | tacatttgaa | ctgctaggtg | agaactctga | aagccctcat | cc | 532 |

<210> SEQ ID NO 48
<211> LENGTH: 495
<212> TYPE: DNA
<213> ORGANISM: Canis familiaris

<400> SEQUENCE: 48

| | | | | | |
|---|---|---|---|---|---|
| gggtacatcc | tatggctgct | atttcgtccc | cgcgttttca | gggttatatg | caccttactg | 60 |
| ggagcccagt | gcaagaggga | tcatctgtgg | gctcactcaa | ttcaccaata | aatgccatat | 120 |
| tgcttttgct | gcattagaag | ctgtttgttt | ccaaacccgg | gagattttgg | atgccatgaa | 180 |
| ccgagactgc | ggaattccac | tcagtcattt | gcaggtagat | ggaggaatga | ccaacaacaa | 240 |
| aattcttatg | caactacaag | cagacattct | atatatccca | gtagtgaagc | cctcgatgcc | 300 |
| agaaacaact | gccctgggag | ctgccatggc | agccggggct | gcggagggag | ttggtgtttg | 360 |
| gagtcttgaa | cccgaggatc | tgtcagcagt | cacgatggag | cgatttgaac | ccagatcaa | 420 |
| tgctgaggaa | agtgaaattc | gttactctac | atggaagaag | gctgtgatga | agtcagtggg | 480 |
| ctgggttaca | actca | | | | | 495 |

<210> SEQ ID NO 49
<211> LENGTH: 572
<212> TYPE: DNA
<213> ORGANISM: Canis familiaris

<400> SEQUENCE: 49

| | | | | | |
|---|---|---|---|---|---|
| gaagatctgg | ccatgtttcg | gtccatcccc | actgctacga | tcttttaccc | aagtgacggg | 60 |
| gtgtcaacag | agaaggcggt | ggaattagca | gccaatacaa | agggcatctg | cttcatccgg | 120 |
| accagccgcc | cagaaaacgc | catcatctat | aacaacaatg | aggatttcca | aatcaaacaa | 180 |
| gccaaggtgg | tcctgaagag | caaggatgac | caggtgactg | tgattggggc | cggagtgacc | 240 |
| ctacatgagg | ccttggctgc | tgctgaactg | ctgaagaaag | agaagatcaa | cattcgtgtg | 300 |
| ttggacccct | tcaccatcaa | gcccctggac | agaaatctca | ttctcgaaag | cgcccgtgcg | 360 |
| accaagggca | ggatcgtcac | cgtggaggac | cattactatg | aaggtggcat | aggtgaggca | 420 |
| gtgtcctctg | ccttggtggg | tgagcctggc | atccgtgtct | cccgccttgc | agttggtgag | 480 |
| gtaccaagaa | gcgggaagcc | agctgagctg | ctgaagatgt | ttggcattga | cagggacgcc | 540 |
| atcgcacaag | ctgtgaggga | ccttgtcgcc | aa | | | 572 |

```
<210> SEQ ID NO 50
<211> LENGTH: 263
<212> TYPE: DNA
<213> ORGANISM: Canis familiaris
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t

<400> SEQUENCE: 50
ccccaaggag atgaggagcg atgaccccag caacaggaan aacagcccac tgaagggctg      60
gtgtgtgtgt ncttcacgtg ccagaagaga agtttagatc ctcccagggg aatcgcaatg    120
ttgtggcgtc ctgacttgta tgtcacgttt tgtgtaaaaa tggtatattc tttaaaatag    180
tgttgataac tggaatattg tatgtatgct tggagatgct ttgtgtgaac ctaagactgt    240
cactcaacag atgttggatt ggg                                            263

<210> SEQ ID NO 51
<211> LENGTH: 123
<212> TYPE: DNA
<213> ORGANISM: Canis familiaris

<400> SEQUENCE: 51
agcctttcta ctgaccctgc aagagtggag cgtgttcacc ttgaacccca gcgtgcagc      60 tgaggtagac atgcctctcc aggagccttt gccttaatgc atctgtgcca gacagacggc    120
tgg                                                                  123

<210> SEQ ID NO 52
<211> LENGTH: 181
<212> TYPE: DNA
<213> ORGANISM: Canis familiaris

<400> SEQUENCE: 52
ggcagtttga aaataaagtt ccagagaaac aaaagctatt tcaggaggat aatggaattc      60
cagtgcatct aaagggtgga gtagctgatg ccctcctgta tagagccact atgatgctta    120
cagttggtgg aacagcatat gccatgtatc agctagctgt ggcttctttt cccaagaagc    180
a                                                                    181

<210> SEQ ID NO 53
<211> LENGTH: 416
<212> TYPE: DNA
<213> ORGANISM: Canis familiaris
<220> FEATURE:
<221> NAME/KEY: misc_feature
<222> LOCATION: (161)..(161)
<223> OTHER INFORMATION: n is a, c, g, or t

<400> SEQUENCE: 53
ggtccgcagt cgttctgtgc ggtcatgtct gtgctggtgc cgcagctgct gaggggccta      60
acaggcctca cccggcggct cccggtgcat cgtgcccaga tccattccaa gccgccgcgg    120
gagcagctcg ggaccatgga tgttgccgtt gggctcacct nctgcttcct gtgtttcctc    180
ctgccatcgg gctgggtcct gtcacacctg gagagctaca agaagcggga gtgaaggggg    240
ctgtcctgtc cctcaccctg tgacctgacc acccctggcc tgtcctgatc atgtctgctg    300
cattcctggc cggccttcca tggatcatgt ccttcaatta cagtgacctc ttctacagtc    360
```

```
atgacctctt gatttctcca tggtgacatc ctgggaccaa acatattggt ttataa      416
```

<210> SEQ ID NO 54
<211> LENGTH: 493
<212> TYPE: DNA
<213> ORGANISM: Canis familiaris
<220> FEATURE:
<221> NAME/KEY: misc_feature
<222> LOCATION: (408)..(408)
<223> OTHER INFORMATION: n is a, c, g, or t
<220> FEATURE:
<221> NAME/KEY: misc_feature
<222> LOCATION: (427)..(427)
<223> OTHER INFORMATION: n is a, c, g, or t
<220> FEATURE:
<221> NAME/KEY: misc_feature
<222> LOCATION: (430)..(430)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t

<400> SEQUENCE: 54

```
cttatgcatt ccttccaaaa ttggatcatt taggtcaaat tatttgatgt taaatcataa      60
gttttcattt gcttacattt acgatatcag cgtcagctac ggaatcaatc tgctgaagga     120
ccgtggctgg cggcgtgtac gatccagcaa ccagcgcctg gacccgact tcatccagga      180
acccctcaga agactccact gacattagga agactcataa gaaccttaca agaaaaagta    240
tcaaccccat caaaacggca gaaaagaaac atatcttgtt attagtagct gaaattccat    300
tttctacatg ttgccatacc ttataaaaac tacactaagc tacgcttaag gaaatacatt    360
ttcttaaata aattagaatt gaaaccaatt tttaagtaaa tctagggntt caatttattc    420
tcattgngtn ttgtttctgg tgcaatcatg aanaacagca tnctattaac caaccttggt    480
cccatgtaca taa                                                        493
```

<210> SEQ ID NO 55
<211> LENGTH: 281
<212> TYPE: DNA
<213> ORGANISM: Canis familiaris
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t

<400> SEQUENCE: 55

```
aattgggact gtgtttggga gcctcatcat tggttatncc aggaatccct ctctgaagca     60
acagctcttc tcctacgcca ttctgggctt tgccctcncg gaggccatgg ggcttttttg    120
cctgatngtg gcctttctca tcctcttngc catgtgaagg agtcgtctcc acctcccata    180
ggtcttttctc ccatgtcttg tctgccctgt atgccctgta tgttccttttt cctatacctc   240
```

```
cccaggcagc ctggggaaag tggttggctc agggtttgac a                281
```

<210> SEQ ID NO 56
<211> LENGTH: 558
<212> TYPE: DNA
<213> ORGANISM: Canis familiaris
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (492)..(493)
<223> OTHER INFORMATION: n is a, c, g, or t
<220> FEATURE:
<221> NAME/KEY: misc_feature
<222> LOCATION: (495)..(496)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (517)..(517)
<223> OTHER INFORMATION: n is a, c, g, or t
<220> FEATURE:
<221> NAME/KEY: misc_feature
<222> LOCATION: (519)..(519)
<223> OTHER INFORMATION: n is a, c, g, or t

<400> SEQUENCE: 56

```
ggtgactttg gacgtccgtt cctgctctgt ggaggcnntg cttcgttccg ggccttgcgg    60
caactcggtn tttccttccc ctgcgcggga gacctctgcc acaaccatgt tacgccagat   120
catcggtcag gccaagaagc atccgagctt gatccccctc ttcatattta ttggggcagg   180
aggtactgga gcagcgctgt atgtattgcg cttggcattg ttcaatccag atgttagttg   240
ggataggaag aataacccag aaccttggaa caaactgggt cccaatgatc aatacaagtt   300
ctactcagtg aatgtagatt acagcaaact gaagaaagaa ggtccagact tctaaatgaa   360
atgtttcact ataaagctgc ttagaatgaa ggtcttccag aagccatccg cacaattttc   420
cacttatcca ggaaatattt cccctctaaa tgcacgaaat catgttggtg tattgtgttg   480
gggtttacac tnnannanta aatatctgaa acttgananng tgtcactatt taatgctgaa   540
aatttgctct gaacttta                                                 558
```

<210> SEQ ID NO 57
<211> LENGTH: 384
<212> TYPE: DNA
<213> ORGANISM: Canis familiaris

<400> SEQUENCE: 57

```
ttggaaggat ggatgcttgc cccaggtcat ggacacctcc acaaatcatc tagtttccca    60
gtatttttat aaatggagat tgggctccat gacactttac ttggtcttcc ttcttacata   120
ggttttttga ttacccttcc tctccttggt gcttatatac ttaagaccct ttagccaaac   180
ccttgccaat gacagtattt cagtcactag ttctcactgt ttcctctgat cattgagcct   240
ttggaaaaaa aatctcacag agcttatatg taatggggct tggttgaaca gatgacttcc   300
```

```
tgtaactgca cctctacttt tggcttctca aaaacagtgg gttggcagta atgcagcgtg    360
gaagttttcc catttctcag tgac                                          384
```

METHODS FOR ENHANCING THE QUALITY OF LIFE OF A SENIOR ANIMAL

CROSS-REFERENCE TO RELATED APPLICATIONS

This application is a continuation-in-part of pending U.S. patent application Ser. No. 11/813,276, filed Mar. 28, 2008, which is a US national stage entry under 35 U.S.C. §371 of International Application No. PCT US 2005/047461 filed Dec. 30, 2005, publication No. WO 2006/074089, which claims priority to U.S. Provisional Application Ser. No. 60/640,890, filed Dec. 30, 2004, each of which is incorporated by reference in its entirety for all purposes.

FIELD OF THE INVENTION

The present invention relates generally to methods for enhancing the quality of life of an animal and particularly to using food compositions containing omega-3 polyunsaturated fatty acids for enhancing the quality of life of a senior or super senior animal.

BACKGROUND OF THE INVENTION

Companion animals such as dogs and cats frequently require differing diets depending on their life stage (age), size, body composition, and breed. Both dog and cat nutrient requirements can be separated into three different life-stages, based on age: growing dogs (or cats), adult dogs (or cats), and senior dogs (or cats). The latter category, senior dogs (or cats), can be further separated into two stages, which include senior (or mature adult) and super senior (or geriatric). Dogs are further separated into different categories for regular breed dogs versus large-breed dogs.

Essential fatty acids, consisting of omega-3 and omega-6 polyunsaturated fatty acids, are critical nutrients for the health of an animal. These nutrients, however, either cannot be made by animals or cannot be made in sufficient amounts to elicit benefits and therefore must be consumed in an animal's diet. See, e.g., Hornstra, G., et al., "Essential fatty acids in pregnancy and early human development", Eur. J. Obs. & Gyn. and Reprod. Biology, 61:57-62 (1995). It has previously been postulated that Docosahexaenoic Acid ("DHA"), an omega-3 polyunsaturated fatty acid, is effective in increasing the maze-learning ability and brain functions in aged mice. See, Lim, S.-Y., "Intakes of dietary docosahexaenoic acid ethyl ester and egg phosphatidylcholine improve maze-learning ability in young and old mice", J. Nutr., 130:1629-1632 (2000).

Rogers discusses the theory of the potential use of antioxidants to slow the deterioration of cognitive function, particularly in the elderly. See Rogers, P., "A healthy body, a healthy mind: long-term impact of diet on mood and cognitive function", Proceedings of the Nutrition Society, 60:135-143 (2001).

Despite the studies and developments relating to improving cognitive abilities, there continues to be a need for methods for enhancing the quality of life of senior animals, as measured by, e.g., enhanced alertness, improved vitality, cartilage protection, maintenance of muscle mass, enhanced digestibility, and improved skin and pelage quality in senior and super senior animals. As previously reported, the super senior pet food composition described herein may be administered to achieve this result. Additionally, we now report herein our surprising discovery that the enhanced quality of life of senior and super senior animals achieved by the administration of the pet food compositions disclosed herein is reflected at the genomic level. Specifically, as described in detail in the Examples below, gene chip data indicate that the expression of genes that encode proteins associated with several biological pathways such as blood clotting and platelet activation and aggregation, bone and muscle integrity, inflammatory responses, cartilage degradation and pain response, DNA damage and repair pathways, neural function, glycogen synthesis and degradation, glycolysis, gluconeogenesis, the pentose phosphate pathway and electron transport are modified, i.e., in general, the majority are beneficially altered through administration to the animal of the super senior pet food compositions described herein.

SUMMARY OF THE INVENTION

The invention provides methods for improving the quality of life of senior and super senior animals by feeding the animal a composition comprising at least about 9% by weight protein, at least about 5% by weight fat, and at least about 0.05% by weight of at least one omega-3 polyunsaturated fatty acid.

In one embodiment, the method comprises feeding the animal an amount of a composition effective to enhance the animal's quality of life, wherein enhanced quality of life is evidenced by improvement in one or more characteristics selected from the group consisting of alertness, vitality, cartilage protection, muscle mass maintenance, digestibility, and skin and pelage quality.

In another embodiment, the method comprises feeding the animal a composition comprising at least one omega-3 polyunsaturated fatty acid selected from the group consisting of docosahexaenoic acid ("DHA") and eicosapentaenoic acid ("EPA"). In an additional embodiment, the method comprises feeding the animal a composition further comprising at least one antioxidant and at least one nutrient selected from the group consisting of choline, manganese, methionine, cysteine, L-carnitine, lysine, and mixtures thereof.

In one embodiment, the method comprises feeding the animal an amount of a composition effective to improve or enhance the animal's quality of life, wherein enhanced quality of life is evidenced by improvement in one or more biological pathways selected from the group consisting of blood clotting and platelet activation and aggregation, bone and muscle integrity, inflammatory responses, cartilage degradation and pain response, DNA damage and repair pathways, neural function, glycogen synthesis and degradation, glycolysis, gluconeogenesis, the pentose phosphate pathway and electron transport.

In another embodiment, the method comprises feeding the animal an amount of a composition effective to enhance the animal's quality of life, wherein enhanced quality of life is evidenced by a change in expression of one or more genes which encode proteins associated with or related to biological pathways selected from the group consisting of blood clotting and platelet activation and aggregation, bone and muscle integrity, inflammatory responses, cartilage degradation and pain response, DNA damage and repair pathways, neural function, glycogen synthesis and degradation, glycolysis, gluconeogenesis, the pentose phosphate pathway and electron transport.

In yet another embodiment, the invention relates to a method to treat an animal suffering from a disorder or disease associated with or related to a biological pathway selected from the group consisting of blood clotting and platelet activation and aggregation, bone and muscle integrity, inflammatory responses, cartilage degradation and pain response, DNA damage and repair pathways, neural function, glycogen synthesis and degradation, glycolysis, gluconeogenesis, the pentose phosphate pathway and electron transport comprising administering to said animal a composition disclosed herein. In one embodiment, said composition comprises at least about 9% by weight protein, at least about 5% by weight fat, and at least about 0.05% by weight of at least one omega-3 polyunsaturated fatty acid. In a further embodiment said composition comprises at least one omega-3 polyunsaturated fatty acid selected from the group consisting of docosahexaenoic acid ("DHA") and eicosapentaenoic acid ("EPA"). In yet an additional embodiment, the composition further comprises at least one antioxidant and at least one nutrient selected from the group consisting of choline, manganese, methionine, cysteine, L-carnitine, lysine, and mixtures thereof.

In another embodiment, the invention relates to methods of measuring or characterizing the enhancement in the quality of life of an animal, particularly a senior or super senior animal, fed a composition described herein by quantitating the gene expression levels of one or more genes selected from a group consisting of those disclosed in Tables 5-14 in said animal and comparing said levels in the animal to levels in the animal prior to administration of the feed composition.

In a further embodiment, the invention relates to methods to enhance the quality of life of an animal by modulating the expression level of one or more genes listed on Tables 5-14 (i.e., up or down regulation as indicated therein) in an animal in order to mimic the pattern of expression seen in vivo after administration of the pet food compositions of the present invention. It is also contemplated herein that modulating the expression levels of these genes may have therapeutic value with regard to the treatment of diseases or disorders associated with the various biological pathways.

The invention also relates to methods to identify an animal that might benefit from feeding a composition as disclosed herein comprising measuring the gene expression levels of any one or more genes listed in Tables 5-14 in said animal and comparing said levels to the gene expression levels seen in Tables 5-14 wherein an animal with levels different than those seen in Tables 5-14 would be identified as potentially benefiting from feeding a composition of the present invention.

In yet another aspect of the present invention there are provided assay methods and kits comprising the components necessary to detect expression of polynucleotides encoding the genes disclosed herein, or levels of encoded protein, or fragments thereof, in body tissue samples derived from an animal, such kits comprising, e.g., antibodies that bind to said polypeptides, or to fragments thereof, or oligonucleotide probes that hybridize with said polynucleotides. In a preferred embodiment, such kits also comprise instructions detailing the procedures by which the kit components are to be used.

Other and further objects, features, and advantages of the present invention will be readily apparent to those skilled in the art.

DETAILED DESCRIPTION OF THE INVENTION

Definitions

It is contemplated that the invention described herein is not limited to the particular methodology, protocols, and reagents described as these may vary. It is also to be understood that the terminology used herein is for the purpose of describing particular embodiments only, and is not intended to limit the scope of the present invention in any way.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices and materials are now described. All publications mentioned herein are incorporated by reference for the purpose of describing and disclosing the materials and methodologies that are reported in the publication which might be used in connection with the invention.

In practicing the present invention, many conventional techniques in molecular biology may be used. These techniques are well known and are explained in, for example, Current Protocols in Molecular Biology, Volumes I, II, and III, 1997 (F. M. Ausubel ed.); Sambrook et al., 1989, Molecular Cloning: A Laboratory Manual, Second Edition, Cold Spring Harbor Laboratory Press, Cold Spring Harbor, N.Y.; DNA Cloning: A Practical Approach, Volumes I and II, 1985 (D. N. Glover ed.); Oligonucleotide Synthesis, 1984 (M. L. Gait ed.); Nucleic Acid Hybridization, 1985, (Hames and Higgins); Transcription and Translation, 1984 (Hames and Higgins eds.); Animal Cell Culture, 1986 (R. I. Freshney ed.); Immobilized Cells and Enzymes, 1986 (IRL Press); Perbal, 1984, A Practical Guide to Molecular Cloning; the series, Methods in Enzymology (Academic Press, Inc.); Gene Transfer Vectors for Mammalian Cells, 1987 (J. H. Miller and M. P. Calos eds., Cold Spring Harbor Laboratory); and Methods in Enzymology Vol. 154 and Vol. 155 (Wu and Grossman, and Wu, eds., respectively).

As used herein and in the appended claims, the singular forms "a", "an", and "the" include plural reference unless the context clearly dictates otherwise.

The terms "senior" or "mature adult" refers to the life-stage of an animal. For small or regular breed canines, the "senior" life stage is from about 7 to about 10 years of age. For felines, the "senior" life stage is from about 7 to about 12 years of age. For large breed canines, over 5 years of age represents "super senior" as described below.

The terms "super senior" or "geriatric" refers to a specific life-stage of an animal. For small or regular breed canines, the super senior stage is any age greater than 10 years of age. For large breed canines, the super senior stage is any age greater than 5 years of age. For felines, the super senior stage is any age greater than 12 years of age.

The term "large breed" canine means a canine that weighs more than 55 pounds when an adult.

The term "regular breed" canine means a canine that weighs less than 55 pounds when an adult.

The term "small breed" canine means a canine that weighs less than 20 pounds when an adult.

The term "super senior pet food composition" refers to any and all of the pet food compositions disclosed herein.

The term "carbohydrate" as used herein includes polysaccharides (e.g., starches and dextrins) and sugars (e.g. sucrose, lactose, maltose, glucose, and fructose) that are metabolized for energy when hydrolyzed. Examples of carbohydrates suitable for inclusion in the compositions disclosed herein include, but are not limited to, corn, grain sorghum, wheat, barley, and rice.

The term "antioxidant" means a substance that is capable of reacting with free radicals and neutralizing them. Illustrative examples of such substances include beta-carotene, selenium, coenzyme Q10 (ubiquinone), luetin, tocotrienols, soy isoflavones, S-adenosylmethionine, glutathione, taurine, N-acetylcysteine, vitamin E, vitamin C, lipoic acid and L-carnitine. Examples of foods containing useful levels of one or more antioxidants include but are not limited to ginkgo biloba, green tea, broccoli, citrus pulp, grape pomace, tomato pomace, carrot spinach, and a wide variety of fruit meals and vegetable meals. It will be understood by one of skill in the art that while units of antioxidants may be provided herein as "ppm", appropriate amounts of antioxidants may also be provided as "IU/kg" where appropriate and customary for a given antioxidant such as, e.g., Vitamin E The terms "beneficial change" in gene expression, or gene expression may be "beneficially altered" and like terms refer to a modification in gene expression (e.g., up or down regulation of mRNA levels) such that levels of proteins encoded by the genes may be correspondingly modified such that an associated biological pathway may be more likely to function normally and with less tendency to reflect pathological changes in the pathway that, e.g., may be typical of a super senior animal. Generally, beneficial changes in gene expression relate to improved health and/or reduced propensity for disease in an animal. As used herein, measuring differences in gene expression "levels" and like terms refer to, e.g., characterizing whether expression of a gene is up or down regulated in an animal compared to a control level.

As used herein, "improving" or "enhancing" the quality of life of an animal refers to as an improvement or enhancement in one or more characteristics selected from a group consisting of alertness, vitality, protection of cartilage, maintenance of muscle mass, digestibility, and skin and pelage quality. Additionally, improvement/enhancement in blood clotting and platelet activation and aggregation, bone and muscle integrity, inflammatory responses, cartilage degradation and pain response, DNA damage and repair pathways, neural function, glycogen synthesis and degradation, glycolysis, gluconeogenesis, the pentose phosphate pathway and electron transport are also contemplated.

An "improvement" or an "enhancement" in a characteristic or biological pathway refers to a modification in said characteristic or biological pathway such that there is a tendency for the characteristic or pathway to appear and/or function normally and with less tendency to reflect pathological changes in the characteristic or pathway that, e.g., may be typical of a super senior animal.

As used herein, methods to "treat" an animal suffering from a disease or disorder is also meant to encompass methods to prevent and/or to ameliorate the disease or disorder as well.

The Invention

The present invention provides methods for improving or enhancing the quality of life of a senior or super senior animal. The methods comprise feeding the animal a composition comprising at least about 9% by weight protein, at least about 5% by weight fat, and at least about 0.05% by weight omega-3 polyunsaturated fatty acid. The methods are useful for enhancing alertness, improving vitality, protecting cartilage, maintaining muscle mass, enhancing digestibility, and improving skin and pelage quality in a senior or super senior animal. The methods are also useful for improving in an animal one or more biological pathways selected from the group consisting of blood clotting and platelet activation and aggregation, bone and muscle integrity, inflammatory responses, cartilage degradation and pain response, DNA damage and repair pathways, neural function, glycogen synthesis and degradation, glycolysis, gluconeogenesis, the pentose phosphate pathway and the electron transport pathway, such improvements also being reflected in overall beneficial changes at the genomic level. Methods for treating animals suffering from disorders or diseases associated with or related to these biological pathways comprising administering the compositions of the present invention are also contemplated herein.

Without being bound by theory, the benefits of the invention may be the result of physiological effects from the addition of omega-3 polyunsaturated fatty acids to a senior or super senior animal's diet. Similarly, the antioxidants, choline, and other nutrients may play a role in enhancing a senior or super senior animal's quality of life.

Although the methods of the present invention may improve an animal's quality of life by enhancing all of the above described characteristics or improving all of the described biological pathways, it is not necessary to demonstrate substantial improvements in each of the characteristics or pathways to achieve the "enhanced quality of life" as defined herein.

When the compositions are administered to a senior or super senior animal, the animal experiences an enhanced quality of life, e.g., exhibits or experiences one or more of enhanced alertness, improved vitality, protected cartilage, maintained muscle mass, enhanced digestibility, improved skin and pelage quality, as well as improvements in e.g., blood clotting and platelet activation and aggregation, bone and muscle integrity, inflammatory responses, cartilage degradation and pain response, DNA damage and repair pathways, neural function, glycogen synthesis and degradation, glycolysis, gluconeogenesis, the pentose phosphate pathway and the electron transport pathway as indicated by overall beneficial changes at the genomic level. Methods for determining these measurements of quality of life are known to skilled artisans. For example, alertness can be measured by various means, including an analysis of metabolism and antioxidant markers, as well as through clinical studies with follow-up questions to participating pet owners. Potential metabolism markers may include ghrelin, GLP-1, thyroid hormone, and/or growth hormone. Potential markers of antioxidant status may include serum vitamin E, ORAC, glutathione peroxidase, alkanels, and/or cell damage indicators. Further, vitality can be measured by various means, including an analysis of metabolism and antioxidant markers, as well as through clinical studies with follow-up questions to participating pet owners. Similarly, cartilage protection can be measured by various means, including an analysis of arthritis biomarkers. Potential arthritis biomarkers may include type TI collagen synthesis, matrix metaloproteinase, osteocalcin, alkaline phosphatase activity, COMP, and fragments of cartilage damage. Muscle mass maintenance can be measured by various means, including an analysis of body composition and digestibility can be measured by various means, including clinical studies with follow-up questions to participating pet owners and animal feeding to determine the percentage of nutrients digested. Skin and pelage quality can be measured by various means, including clinical studies with follow-up questions to participating pet owners. Additionally, as discussed above, improvements in quality of life is also reflected at the genomic level, as evidenced by gene chip data which indicate beneficial changes on the expression of a majority of genes associated with various important biological pathways including blood clotting and platelet activation and aggregation, bone and muscle integrity, inflammatory responses, cartilage degradation and protection and pain response, DNA damage and repair pathways, neural function, glycogen synthesis and degradation, glycolysis, gluconeogenesis, the pentose phosphate pathway and the electron transport pathway. The identities of these genes are provided in the Examples below.

The methods of the invention are useful for enhancing the quality of life of humans and animals, including primates (e.g., monkeys, chimpanzees, etc.), companion animals (e.g., dogs, cats, horses, etc.), farm animals (e.g., goats, sheep, swine, cattle, etc.), laboratory animals (e.g., mice, rats, etc.), birds (e.g., domestic birds such as canaries, parrots, etc. and commercial birds such as chickens, ducks, turkeys, etc.), rodents (e.g., hamsters, guinea pigs, gerbils, rabbits, hedgehogs, ferrets, chinchillas, etc.), and wild, exotic, and zoo animals (e.g., wolves, bears, deer, etc.). In various embodiments, the animal is a cat, a dog, or a horse.

The compositions of the present invention are designed to enhance digestibility and improve chewability. Canine and feline foods are typically formulated based on life stage (age), size, body composition, and breed. Thus, some embodiments of the present invention include compositions that are formulated to address specific nutritional differences between regular or small breed dogs, large breed dogs, and cats.

The invention provides methods utilizing a variety of compositions containing at least one omega-3 polyunsaturated fatty acid. The compositions include foods, supplements, treats, and toys (typically chewable and consumable toys). The methods also provide the compositions to the designated animals over a period of time that is long enough to effectuate the improved quality of life. In one embodiment, the method provides the animal with a composition for at least thirty days.

The compositions for use in the methods of the present invention generally have an omega-3 polyunsaturated fatty acid content of at least about 0.02% (or from about 0.05% to about 10%, or from about 0.1% to about 6%) by weight on a dry matter basis. In some embodiments, the omega-3 polyunsaturated fatty acid is DHA. In other embodiments, the omega-3 polyunsaturated fatty acid is EPA. In still other embodiments, the omega-3 polyunsaturated fatty acid comprises a mixture of DHA and EPA.

In some embodiments, the composition containing omega-3 polyunsaturated fatty acid is a food. Although both liquid and solid foods are provided, solid foods are typically preferred. Foods include both dry foods and wet foods. Some of the non-polyunsaturated fatty acid components of the food, and their preferred proportions, include those listed in Table 1.

TABLE 1

| Component | Proportion of the composition (% of dry weight of composition or parts per million) |
|---|---|
| Protein | from about 9% to about 55%, or from about 18% to 30%, or from about 33% to about 55% or from about 18% to about 20% or from about 33% to about 36% |
| Fat | from about 7% to about 35%, or from about 18% to about 35%, or from about 7% to about 24%, or from about 14% to about 24%, or from about 14% to about 16% or from about 18% to about 24% |
| Antioxidant | from about 0 ppm to about 7500 ppm, or from about 0.05 ppm to about 3600 ppm, or from about 250 to about 3600, or from about 250 ppm to about 1650 ppm, or from about 5 ppm to about 225 ppm, or from about 0.05 ppm to about 2.4 ppm |

In one embodiment, the methods of this invention comprise feeding a super senior animal a composition in an amount effective to enhance the animal's quality of life. Such compositions generally comprise:
(a) 0.02% (or from about 0.05% to about 10%, or from about 0.1% to about 6%) at least one omega-3 polyunsaturated fatty acid, and
(b) at least one of the following:
  (i) from about 10% to about 55% (or from about 18% to about 30%, or from about 33% to about 55% or from about 18% to about 20% or from about 33% to about 36%) protein,
  (ii) from about 7% to about 35% (or from about 18% to about 35%, or from about 7% to about 24%, or from about 14% to about 24%, or from about 14% to about 16% or from about 18% to about 24%) fat, and
  (iii) at least about 0.05 (or from about 0.05 ppm or IU/kg to about 7500 ppm or IU/kg, or from about 250 ppm or IU/kg to about 3600 ppm or IU/kg, or from about 250 ppm or IU/kg to about 1650 ppm or IU/kg, or from about 5 ppm or IU/kg to about 225 ppm or IU/kg, or from about 0.05 ppm or IU/kg to about 2.4 ppm or IU/kg) antioxidant.

In another embodiment, the methods of this invention comprise feeding a super senior regular or small breed canine a composition in an amount effective to enhance the canine's quality of life. The composition generally comprises:
(a) at least one of the following:
  (i) at least about 0.02% (or from about 0.02% to about 0.3%, or from about 0.05% to about 0.3%, or from about 0.05% to about 0.2%) DHA, and
  (ii) at least about 0.1% (or from about 0.1% to about 0.5%, or from about 0.2% to about 0.5%, or from about 0.2% to about 0.3%) EPA,
(b) at least about 9% (or from about 9% to about 30%, or from about 18% to about 30%, or from about 18% to about 20%) protein,
(c) at least about 7% (or from about 7% to about 24%, or from about 14% to about 24%, or from about 14% to about 16%) fat, and
(d) at least one of the following:
  (i) at least about 250 IU/kg (or from about 250 IU/kg to about 1500 IU/kg, or from about 500 IU/kg to about 1500 IU/kg, or from about 500 IU/kg to about 1000 IU/kg) vitamin E,
  (iv) at least about 50 ppm (or from about 50 ppm to about 500 ppm, or from about 100 ppm to about 500 ppm, or from about 100 ppm to about 301 ppm) vitamin C,
  (v) at least about 600 ppm (or from about 600 ppm to about 2400 ppm, or from about 1260 ppm to about 2400 ppm, or from about 1260 ppm to about 1545 ppm) taurine,
  (vi) at least about 50 ppm (or from about 50 ppm to about 200 ppm, or from about 100 to about 160, or from about 100 to about 155) lipoic acid, and
  (vii) at least about 50 ppm (or from about 50 ppm to about 500 ppm, or from about 200 ppm to about 500 ppm, or from about 200 ppm to about 350 ppm) carnitine.

In another embodiment, the methods of this invention comprise feeding a super senior large breed canine a composition in an amount effective to enhance the canine's quality of life. The compositions generally comprise:
(a) at least one of the following:
  (i) at least about 0.02% (or from about 0.02% to about 0.3%, or from about 0.05% to about 0.3%, or from about 0.05% to about 0.2%) DHA, and
  (ii) at least about 0.1% (or from about 0.1% to about 0.5%, or from about 0.2% to about 0.5%, or from about 0.2% to about 0.3%) EPA,
(b) at least about 9% (or from about 9% to about 30%, or from about 18% to about 30%, or from about 18% to about 20%) protein, (c) at least about 7% (or from about 7% to about 24%, or from about 14% to about 24%, or from about 14% to about 16%) fat, and
(d) at least one of the following:
   (i) at least about 250 IU/kg (or from about 250 IU/kg to about 1500 IU/kg, or from about 500 IU/kg to about 1500 IU/kg, or from about 500 IU/kg to about 1000 IU/kg) vitamin E,
   (viii) at least about 50 ppm (or from about 50 ppm to about 500 ppm, or from about 100 ppm to about 500 ppm, or from about 100 ppm to about 301 ppm) vitamin C,
   (ix) at least about 600 ppm (or from about 600 ppm to about 2400 ppm, or from about 1260 ppm to about 2400 ppm, or from about 1260 ppm to about 1575 ppm) taurine, and
   (x) at least about 50 ppm (or from about 50 ppm to about 200 ppm, or from about 100 to about 160, or from about 100 to about 155) lipoic acid, and
   (xi) at least about 50 ppm (or from about 50 ppm to about 500 ppm, or from about 200 ppm to about 500 ppm, or from about 200 ppm to about 350 ppm) carnitine.

In another embodiment, the methods of this invention comprise feeding a super senior feline a composition in an amount effective to enhance the feline's quality of life. The compositions generally comprise:
(a) at least one of the following:
   (i) at least about 0.05% (or from about 0.05% to about 0.30%, or from about 0.1% to about 0.30%, or from about 0.1% to about 0.2%) DHA, and
   (ii) at least about 0.1% (or from about 0.1% to about 0.5%, or from about 0.2% to about 0.5%, or from about 0.2% to about 0.3%) EPA,
(b) at least about 15% (or from about 15% to about 55%, or from about 30% to about 55%, or from about 33% to about 36%) protein,
(c) at least about 9% (or from about 9% to about 35%, or from about 18% to about 35%, or from about 18% to about 24%) fat, and
(d) at least one of the following:
   (i) at least about 250 IU/kg (or from about 250 IU/kg to about 1500 IU/kg, or from about 500 IU/kg to about 1500 IU/kg, or from about 500 IU/kg to about 1100 IU/kg) vitamin E,
   (xii) at least about 50 ppm (or from about 50 ppm to about 300 ppm, or from about 100 ppm to about 300 ppm, or from about 100 ppm to about 200 ppm) vitamin C,
   (xiii) at least about 1100 ppm (or from about 1100 ppm to about 3500 ppm, or from about 2300 ppm to about 3500 ppm, or from about 2300 ppm to about 2350 ppm) taurine, and
   (xiv) at least about 200 ppm (or from about 200 to about 750 ppm, or from about 400 ppm to about 750 ppm, or from about 400 to about 525 ppm) carnitine, and
   (xv) at least about 0.05% (or from about 0.05% to about 0.6%, or from about 0.1% to about 0.6%, or from about 0.1% to about 0.4%) cystine.

In another embodiment, the methods of this invention comprise feeding a super senior animal a composition in an amount effective to enhance the animal's alertness and vitality. The composition generally comprises:
(a) 0.02% (or from about 0.05% to about 10%, or about 0.1% to about 6%) at least one omega-3 polyunsaturated fatty acid, and
(b) at least one of the following:
   (xvi) from about 10% to about 55% (or from about 18% to about 30%, or from about 33% to about 55% or from about 18% to about 20% or from about 33% to about 36%) protein,
   (xvii) from about 7% to about 35% (or from about 18% to about 35%, or from about 7% to about 24%, or from about 14% to about 24%, or from about 14% to about 16% or from about 18% to about 24%) fat,
   (xviii) at least about 0.05 (or from about 0.05 ppm to about 7500 ppm, or from about 250 to about 3600, or from about 250 ppm to about 1650 ppm, or from about 5 ppm to about 225 ppm, or from about 0.05 ppm to about 2.4 ppm) antioxidant, and
   (xix) at least about 1000 ppm (or from about 1000 ppm to about 5000 ppm, from about 3300 ppm to about 5000 ppm, or from about 2000 ppm to about 3000 ppm, or from about 3000 ppm to about 4000 ppm) choline.

In another embodiment, the methods of this invention comprise feeding a super senior regular or small breed canine a composition in an amount effective to enhance the canine's alertness and vitality. The composition generally comprises:
(a) at least one of the following:
   (i) at least about 0.02% (or from about 0.02% to about 0.3%, or from about 0.05% to about 0.3%, or from about 0.05% to about 0.2%) DHA, and (ii) at least about 0.1% (or from about 0.1% to about 0.5%, or from about 0.2% to about 0.5%, or from about 0.2% to about 0.3%) EPA,
(b) at least about 9% (or from about 9% to about 30%, or from about 18% to about 30%, or from about 18% to about 20%) protein,
(c) at least about 7% (or from about 7% to about 24%, or from about 14% to about 24%, or from about 14% to about 16%) fat,
(d) at least one of the following:
   (i) at least about 250 IU/kg (or from about 250 IU/kg to about 1500 IU/kg, or from about 500 IU/kg to about 1500 IU/kg, or from about 500 IU/kg to about 1000 IU/kg) vitamin E,
   (xx) at least about 50 ppm (or from about 50 ppm to about 500 ppm, or from about 100 ppm to about 500 ppm, or from about 100 ppm to about 301 ppm) vitamin C,
   (xxi) at least about 600 ppm (or from about 600 ppm to about 2400 ppm, or from about 1260 ppm to about 2400 ppm, or from about 1260 ppm to about 1545 ppm) taurine, and
   (xxii) at least about 50 ppm (or from about 50 ppm to about 200 ppm, or from about 100 to about 160, or from about 100 to about 155) lipoic acid, and
   (xxiii) at least about 50 ppm (or from about 50 ppm to about 500 ppm, or from about 200 ppm to about 500 ppm, or from about 200 ppm to about 350 ppm) carnitine,
(e) at least about 1000 ppm (or from about 1000 ppm to about 3200 ppm, or from about 2000 ppm to about 3200 ppm, or from about 2000 ppm to about 2500 ppm) choline,
(f) at least about 50 ppm (or from about 50 ppm to about 150 ppm, or from about 100 ppm to about 150 ppm, or from about 100 ppm to about 110 ppm) manganese, and
(g) at least about 0.4% (or from about 0.4% to about 2%, or from about 0.9% to about 2%, or from about 0.9% to about 1.2%) lysine, and
(h) at least about 0.4% to about 1.5% methionine.

In another embodiment, the methods of this invention comprise feeding a super senior large breed canine a composition in an amount effective to enhance the canine's alertness and vitality. The composition generally comprises:
- (a) at least one of the following:
  - (i) at least about 0.02% (or from about 0.02% to about 0.3%, or from about 0.05% to about 0.3%, or from about 0.05% to about 0.2%) DHA, and
  - (ii) at least about 0.1% (or from about 0.1% to about 0.5%, or from about 0.2% to about 0.5%, or from about 0.2% to about 0.3%) EPA,
- (b) at least about 9% (or from about 9% to about 30%, or from about 18% to about 30%, or from about 18% to about 20%) protein,
- (c) at least about 7% (or from about 7% to about 24%, or from about 14% to about 24%, or from about 14% to about 16%) fat,
- (d) at least one of the following:
  - (i) at least about 250 IU/kg (or from about 250 IU/kg to about 1500 IU/kg, or from about 500 IU/kg to about 1500 IU/kg, or from about 500 IU/kg to about 1000 IU/kg) vitamin E,
  - (xxiv) at least about 50 ppm (or from about 50 ppm to about 500 ppm, or from about 100 ppm to about 500 ppm, or from about 100 ppm to about 301 ppm) vitamin C,
  - (xxv) at least about 600 ppm (or from about 600 ppm to about 2400 ppm, or from about 1260 ppm to about 2400 ppm, or from about 1260 ppm to about 1575 ppm) taurine, and
  - (xxvi) at least about 50 ppm (or from about 50 ppm to about 200 ppm, or from about 100 to about 160, or from about 100 to about 155) lipoic acid, and
  - (xxvii) at least about 50 ppm (or from about 50 ppm to about 500 ppm, or from about 200 ppm to about 500 ppm, or from about 200 ppm to about 350 ppm) carnitine,
- (e) at least about 1000 ppm (or from about 1000 ppm to about 3200 ppm, or from about 2000 ppm to about 3200 ppm, or from about 2000 ppm to about 2500 ppm) choline,
- (f) at least about 50 ppm (or from about 50 ppm to about 150 ppm, or from about 100 ppm to about 150 ppm, or from about 100 ppm to about 110 ppm) manganese, and
- (g) at least about 0.4% (or from about 0.4% to about 2%, or from about 0.9% to about 2%, or from about 0.9% to about 1.2%) lysine, and
- (h) at least about 0.4% to about 1.5% methionine.

In another embodiment, the methods of this invention comprise feeding a super senior feline a composition in an amount effective to enhance the feline's alertness and vitality. The composition generally comprises:
- (a) at least one of the following:
  - (i) at least about 0.05% (or from about 0.05% to about 0.30%, or from about 0.1% to about 0.30%, or from about 0.1% to about 0.2%) DHA, and
  - (ii) at least about 0.1% (or from about 0.1% to about 0.5%, or from about 0.2% to about 0.5%, or from about 0.2% to about 0.3%) EPA,
- (b) at least about 15% (or from about 15% to about 55%, or from about 30% to about 55%, or from about 33% to about 36%) protein,
- (c) at least about 9% (or from about 9% to about 35%, or from about 18% to about 35%, or from about 18% to about 24%) fat,
- (d) at least one of the following:
  - (i) at least about 250 IU/kg (or from about 250 IU/kg to about 1500 IU/kg, or from about 500 IU/kg to about 1500 IU/kg, or from about 500 IU/kg to about 1100 IU/kg) vitamin E,
  - (xxviii) at least about 50 ppm (or from about 50 ppm to about 300 ppm, or from about 100 ppm to about 300 ppm, or from about 100 ppm to about 200 ppm) vitamin C,
  - (xxix) at least about 1100 ppm (or from about 1100 ppm to about 3500 ppm, or from about 2300 ppm to about 3500 ppm, or from about 2300 ppm to about 2350 ppm) taurine, and
  - (xxx) at least about 200 ppm (or from about 200 to about 750 ppm, or from about 400 ppm to about 750 ppm, or from about 400 to about 525 ppm) carnitine, and
  - (xxxi) at least about 0.05% (or from about 0.05% to about 0.6%, or from about 0.1% to about 0.6%, or from about 0.1% to about 0.4%) cystine.
- (e) at least about 1600 ppm (or from about 1600 ppm to about 5000 ppm, or from about 3300 ppm to about 5000 ppm, or from about 3300 ppm to about 3400 ppm) choline,
- (f) at least about 50 ppm (or from about 50 ppm to about 150 ppm, or from about 100 ppm to about 150 ppm, or from about 100 ppm to about 110 ppm) manganese, and
- (g) at least about 0.7% (or from about 0.7% to about 3%, or from about 1.4% to about 3%, or from about 1.4% to about 1.7%) lysine, and
- (h) at least about 0.4% to about 1.5% methionine.

In another embodiment, this invention provides a method for improving the quality of life of a senior or super senior small or regular breed canine. The method comprises feeding the canine a composition comprising:
- from about 60% to about 70% by weight carbohydrate;
- from about 15% to about 25% by weight protein selected from the group consisting of animal protein and vegetable protein;
- from about 5% to about 7% by weight fat selected from the group consisting of animal fat and vegetable fat;
- from about 2.5% to about 4% by weight of at least one omega-3 polyunsaturated fatty acids;
- from about 1% to about 4% by weight fiber;
- from about 1% to about 2% by weight minerals; and
- from about 0.5 to about 1.5% by weight vitamins.

In another embodiment, this invention provides a method for improving the quality of life of a senior or super senior large breed canine. The method comprises feeding the canine a composition comprising:
- from about 60% to about 70% by weight carbohydrate;
- from about 15% to about 25% by weight protein selected from the group consisting of animal protein and vegetable protein;
- from about 5% to 10% by weight fat selected from the group consisting of animal fat and vegetable fat;
- from about 3% to about 5% by weight of at least one omega-3 polyunsaturated fatty acids;
- from about 1% to about 4% by weight fiber;
- from about 0.5% to about 1% by weight minerals; and
- from about 0.75 to about 1.25% by weight vitamins.

In another embodiment, this invention provides a method for improving the quality of life of a senior or super senior feline. The method comprises feeding the feline a composition comprising:
- from about 30% to about 35% by weight carbohydrate;
- from about 35% to about 50% by weight protein selected from the group consisting of animal protein and vegetable protein;

from about 12% to about 15% by weight fat selected from the group consisting of animal fat and vegetable fat;
from about 1% to about 2% by weight of at least one omega-3 polyunsaturated fatty acids;
from about 1% to about 5% by weight fiber;
from about 1% to about 2% by weight minerals; and
from about 1% to about 2% by weight vitamins.

In a further embodiment, this invention provides a method for improving the quality of life of a senior or super senior animal comprising feeding the animal (e.g., small, regular or large breed canine or feline, as the case may be) a composition comprising the components as indicated in Table 1A below:

TABLE 1A

Chemical composition of Super Senior Foods

| Nutrient Component | Small/Regular Breed Canine | Large Breed Canine | Feline |
|---|---|---|---|
| Crude Protein, % | 20.1 | 19.34 | 35.73 |
| Fat, % | 16.45 | 16.92 | 22.47 |
| Calcium, % | 0.71 | 0.73 | 0.94 |
| Phosphorus, % | 0.61 | 0.68 | 0.77 |
| EPA, % | 0.32 | 0.32 | 0.23 |
| DHA, % | 0.22 | 0.22 | 0.32 |
| Linoleic Acid, % | 3.96 | 4.04 | 5.05 |
| Total N-3 fatty acids, % | 1.3 | 2.24 | 1.14 |
| Total N-6 fatty acids, % | 3.96 | 3.99 | 5.09 |
| Taurine, ppm | 1400 | 15.25 | 2100 |
| Carnitine, ppm | 314 | 337 | 367 |
| Methioinine, % | 1 | 1.19 | 1.32 |
| Cystine, % | 0.25 | 0.24 | 0.47 |
| Manganese, ppm | 87 | 100 | 104 |
| Vitamin E, IU/kg | 1492 | 1525 | 1292 |
| Vitamin C, ppm | 127 | 261 | 141 |
| Lipoic Acid, ppm* | 101 | 135 | |

*Lipoic acid based on formulated, not analyzed values.

The compositions for use in the methods of this invention further comprise at least one nutrient selected from the group consisting of manganese, methionine, cysteine, mixtures of methionine and cysteine, L-carnitine, lysine, and arginine. Specific preferred amounts for each component in a composition will depend on a variety of factors including, for example, the species of animal consuming the composition; the particular components included in the composition; the age, weight, general health, sex, and diet of the animal; the animal's consumption rate, and the like. Thus, the component amounts may vary widely, and may even deviate from the proportions given herein.

The omega-3 fatty acids may be obtained from a variety of sources. One convenient source is fish oils from, for example, menhaden, mackerel, herring, anchovy, and salmon. DHA and EPA are typical fatty acids present in such fish oils, and, together often make up a significant portion of the oil, such as from about 25% to about 38% of the oil.

When the composition is an animal food, vitamins and minerals preferably are included in amounts required to avoid deficiency and maintain health. These amounts are readily available in the art. The National Research Council (NRC), for example, provides recommended amounts of such ingredients for farm animals. See, e.g., Nutrient Requirements of Swine (10th Rev. Ed., Nat'l Academy Press, Wash. D.C., 197298), Nutrient Requirements of Poultry (9th Rev. Ed., Nat'l Academy Press, Wash. D.C., 1994), Nutrient Requirements of Horses (Fifth Rev. Ed., Nat'l Academy Press, Wash. D.C., 1989), Nutrient Requirements of Dogs and Cats (Nat'l Academy Press, Wash. D.C., 2006). The American Feed Control Officials (AAFCO), for example, provides recommended amounts of such ingredients for dogs and cats. See American Feed Control Officials, Inc., Official publication, pp. 126-140 (2003). Examples of vitamins useful as food additives include vitamin A, B1, B2, B6, B12, C, D, E, K, H (biotin), K, folic acid, inositol, niacin, and pantothenic acid. Examples of minerals and trace elements useful as food additives include calcium, phosphorus, sodium, potassium, magnesium, copper, zinc, chloride, and iron salts.

The methods of the present invention include compositions that may further contain other additives known in the art. Preferably, such additives are present in amounts that do not impair the purpose and effect provided by the invention. Examples of additives include, for example, substances with a stabilizing effect, processing aids, substances that enhance palatability, coloring substances, and substances that provide nutritional benefits.

Stabilizing substances include, for example, substances that tend to increase the shelf life of the composition. Potentially suitable examples of such substances include, for example, preservatives, antioxidants, synergists and sequestrants, packaging gases, stabilizers, emulsifiers, thickeners, gelling agents, and humectants. Examples of emulsifiers and/or thickening agents include, for example, gelatin, cellulose ethers, starch, starch esters, starch ethers, and modified starches.

Additives for coloring, palatability ("pal enhancers"), and nutritional purposes include, for example, colorants (e.g., iron oxide, such as the red, yellow, or brown forms); sodium chloride, potassium citrate, potassium chloride, and other edible salts; vitamins; minerals; and flavoring. Such additives are known in the art. See, e.g., U.S. Pat. No. 3,202,514. See also, U.S. Pat. No. 4,997,671. Flavorants include, for example, dairy product flavorants (e.g., milk or cheese), meat flavorants (e.g., bacon, liver, beef, poultry, or fish), oleoresin, pinacol, and the various flavorants identified in the trade by a FEMA (Flavor Extract Manufacturers Association) number. Flavorants help provide additional palatability, and are known in the art. See, e.g., U.S. Pat. No. 4,997,672. See also, U.S. Pat. No. 5,004,624. See also, U.S. Pat. No. 5,114,704. See also, U.S. Pat. No. 5,532,010. See also, U.S. Pat. No. 6,379,727. The concentration of such additives in the composition typically may be up to about 5% by weight. In some embodiments, the concentration of such additives (particularly where such additives are primarily nutritional balancing agents, such as vitamins and minerals) is from about 0% to about 2.0% by weight. In some embodiments, the concentration of such additives (again, particularly where such additives are primarily nutritional balancing agents) is from about 0% to about 1.0% by weight.

Supplements include, for example, a feed used with another feed to improve the nutritive balance or performance of the total. Supplements include compositions that are fed undiluted as a supplement to other feeds, offered free choice with other parts of an animal's ration that are separately available, or diluted and mixed with an animal's regular feed to produce a complete feed. The AAFCO, for example, provides a discussion relating to supplements in the American Feed Control Officials, Inc. Official Publication, p. 220 (2003). Supplements may be in various forms including, for example, powders, liquids, syrups, pills, encapsulated compositions, and the like.

Treats include, for example, compositions that are given to an animal to entice the animal to eat during a non-meal time. Treats for canines include, for example, dog bones. Treats may be nutritional, wherein the composition comprises one or more nutrients, and may, for example, have a composition as described above for food. Non-nutritional treats encompass any other treats that are non-toxic.

Toys include, for example, chewable toys. Toys for dogs include, for example, artificial bones. There is a wide range of suitable toys currently marketed. See, e.g., U.S. Pat. No. 5,339,771 (and references disclosed in U.S. Pat. No. 5,339,771). See also, e.g., U.S. Pat. No. 5,419,283 (and references disclosed in U.S. Pat. No. 5,419,283). The invention provides both partially consumable toys (e.g., toys comprising plastic components) and fully consumable toys (e.g., rawhides and various artificial bones). It should be further recognized that this invention provides toys for both human and non-human use, particularly for companion, farm, and zoo animal use, and particularly for dog, cat, or bird use.

A "food" is a nutritionally complete diet for the intended recipient animal (e.g., domestic cat or domestic dog). A "nutritionally complete diet" is a diet that includes sufficient nutrients for maintenance of normal health of a healthy animal on the diet. The methods of this invention utilize compositions that are not intended to be restricted by any specific listing of proteinaceous or fat ingredients or product form. The compositions can be prepared in, for example, a dry, canned, wet, or intermediate moisture form using conventional pet food processes. In some embodiments, the moisture content is from about 10% to about 90% of the total weight of the composition. In other embodiments, the moisture content is from about 65% to about 75% of the total weight of the composition.

In preparing a composition for use with the methods of the present invention, any ingredient (e.g., fish oil) generally may, for example, be incorporated into the composition during the processing of the formulation, such as during and/or after mixing of other components of the composition. Distribution of these components into the composition can be accomplished by conventional means. In one embodiment, ground animal and poultry proteinaceous tissues are mixed with the other ingredients, including fish oils, cereal grains, other nutritionally balancing ingredients, special-purpose additives (e.g., vitamin and mineral mixtures, inorganic salts, cellulose and beet pulp, bulking agents, and the like); and water that is sufficient for processing is also added. These ingredients preferably are mixed in a vessel suitable for heating while blending the components. Heating of the mixture may be effected using any suitable manner, such as, for example, by direct steam injection or by using a vessel fitted with a heat exchanger. Following the addition of the last ingredient, the mixture is heated to a temperature range of from about 50° F. (10° C.) to about 212° F. (100° C.). In some embodiments, the mixture is heated to a temperature range of from about 70° F. (21° C.) to about 140° F. (60° C.). Temperatures outside these ranges are generally acceptable, but may be commercially impractical without use of other processing aids. When heated to the appropriate temperature, the material will typically be in the form of a thick liquid. The thick liquid is filled into cans. A lid is applied, and the container is hermetically sealed. The sealed can is then placed into conventional equipment designed to sterilize the contents. This is usually accomplished by heating to temperatures of greater than about 230° F. (110° C.) for an appropriate time, which is dependent on, for example, the temperature used and the composition.

Methods of the present invention include utilizing compositions that can be prepared in a dry form using conventional processes. In one embodiment, dry ingredients, including, for example, animal protein sources, plant protein sources, grains, etc., are ground and mixed together. Moist or liquid ingredients, including fats, oils, animal protein sources, water, etc., are then added to and mixed with the dry mix. The mixture is then processed into kibbles or similar dry pieces. Kibble is often formed using an extrusion process in which the mixture of dry and wet ingredients is subjected to mechanical work at a high pressure and temperature, and forced through small openings and cut off into kibble by a rotating knife. The wet kibble is then dried and optionally coated with one or more topical coatings which may include, for example, flavors, fats, oils, powders, and the like. Kibble also can be made from the dough using a baking process, rather than extrusion, wherein the dough is placed into a mold before dry-heat processing.

The compositions are also designed to be easier to chew. Canine and feline foods are typically formulated based on life stage (age), size, body composition, and breed. In the methods of this invention, some embodiments of the compositions address specific nutritional differences between super senior regular or small breed dogs, large breed dogs, and cats.

All percentages expressed herein are on a weight by dry matter basis unless specifically stated otherwise.

As noted previously, this invention is directed, in part, to a method for enhancing the quality of life of an animal. The method comprises feeding a senior or super senior animal a composition in an amount effective to enhance alertness, improve vitality, protect cartilage, maintain muscle mass, enhance digestibility, and improve skin and pelage quality. Additionally, we now report herein our surprising discovery that the enhanced quality of life of an animal achieved by administration of the compositions of the present invention is reflected at the genomic level. While it may be that a change in expression of any one gene disclosed in the tables presented below may result in beneficial or deleterious biological effects, the data presented herein indicate that, overall, the observed expression profiles are consistent with the beneficial biological effects seen in vivo after administration of the diets disclosed herein. Specifically, gene chip data indicate that the expression of genes that encode proteins associated with or related to several biological pathways such as blood clotting and platelet activation and aggregation, bone and muscle integrity, inflammatory responses, cartilage degradation and pain response, DNA damage and repair pathways, neural function, glycogen synthesis and degradation, glycolysis, gluconeogenesis, the pentose phosphate pathway and electron transport are, for the most part, beneficially altered through administration to the animal of compositions described herein. Thus, the invention also relates to methods of measuring or characterizing the enhancement in the quality of life of an animal, particularly a senior or super senior animal, fed a composition described herein by quantitating the gene expression levels of one or more genes selected from a group consisting of those disclosed in Tables 5-14 in said animal and comparing said levels in the animal to levels in the animal prior to administration of the feed composition. Quantitation of gene expression may be carried out in numerous ways familiar to one of skill in the art and include such techniques as RT PCR as well as gene chip assays and Northern blotting. Thus, it is contemplated herein that the expression levels detected may be used, for example, in methods to measure enhancement in the quality of life of an animal as disclosed herein.

In another aspect, the present invention relates to kits which comprise:

(a) a polynucleotide of a gene disclosed herein or a fragment thereof, (b) a nucleotide sequence complementary to that of (a);

(c) a polypeptide encoded by a gene disclosed herein, or a fragment thereof, or (d) an antibody to a polypeptide encoded by a gene disclosed herein, or a fragment thereof.

It will be appreciated that in any such kit, (a), (b), (c) or (d) may comprise a substantial component. The manufacture of kits as described herein and components thereof (e.g., antibody production) may be achieved according to conventional methods.

It is contemplated herein that modulating the expression levels of the genes disclosed herein may have therapeutic value with regard to the treatment of diseases or disorders associated with the various biological pathways. Such determination may be made on a gene by gene basis without undue experimentation, for example, by assessing expression levels in tissues as well as in blood samples, or by assaying expression levels in vitro in cells or cell lines relevant to particular disease states and suitable for such experimentation. In vivo models of disease might also be utilized in such experimentation. The nature of these and other suitable additional assays would be familiar to one of skill in the art. Thus, based on the genomic data disclosed herein, the invention also relates to methods to enhance the quality of life of an animal by modulating the expression level of one or more genes listed on Tables 5-14 (i.e. up or down regulation as indicated therein) in an animal in order to mimic the pattern of expression seen in vivo after administration of the pet food compositions of the present invention.

Modulation of gene expression levels may be achieved through the use of known modulators of gene expression suitable for administration in vivo, including, but not limited to, ribozymes, antisense oligonucleotides, triple helix DNA, RNA aptamers and/or double stranded RNA directed to an appropriate nucleotide sequence of a gene of interest. These inhibitory molecules may be created using conventional techniques by one of skill in the art without undue burden or experimentation. For example, modification (e.g. inhibition) of gene expression may be obtained by designing antisense molecules, DNA or RNA, to the control regions of the genes discussed herein, i.e. to promoters, enhancers, and introns. For example, oligonucleotides derived from the transcription initiation site, e.g., between positions −10 and +10 from the start site may be used. Notwithstanding, all regions of the gene may be used to design an antisense molecule in order to create those which gives strongest hybridization to the mRNA and such suitable antisense oligonucleotides may be produced and identified by standard assay procedures familiar to one of skill in the art.

Similarly, inhibition of gene expression may be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). These molecules may also be designed to block translation of mRNA by preventing the transcript from binding to ribosomes.

Ribozymes, enzymatic RNA molecules, may also be used to modulate gene expression by catalyzing the specific cleavage of RNA. The mechanism of ribozyme action involves sequence-specific hybridization of the ribozyme molecule to complementary target RNA, followed by endonucleolytic cleavage. Examples which may be used include engineered "hammerhead" or "hairpin" motif ribozyme molecules that can be designed to specifically and efficiently catalyze endonucleolytic cleavage of gene sequences.

Specific ribozyme cleavage sites within any potential RNA target are initially identified by scanning the target molecule for ribozyme cleavage sites which include the following sequences: GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Ribozyme methods include exposing a cell to ribozymes or inducing expression in a cell of such small RNA ribozyme molecules (Grassi and Marini, 1996, Annals of Medicine 28: 499-510; Gibson, 1996, Cancer and Metastasis Reviews 15: 287-299). Intracellular expression of hammerhead and hairpin ribozymes targeted to mRNA corresponding to at least one of the genes discussed herein can be utilized to inhibit protein encoded by the gene.

Ribozymes can either be delivered directly to cells, in the form of RNA oligonucleotides incorporating ribozyme sequences, or introduced into the cell as an expression vector encoding the desired ribozymal RNA. Ribozymes can be routinely expressed in vivo in sufficient number to be catalytically effective in cleaving mRNA, and thereby modifying mRNA abundance in a cell (Cotten et al., 1989 EMBO J. 8:3861-3866). In particular, a ribozyme coding DNA sequence, designed according to conventional, well known rules and synthesized, for example, by standard phosphoramidite chemistry, can be ligated into a restriction enzyme site in the anticodon stem and loop of a gene encoding a tRNA, which can then be transformed into and expressed in a cell of interest by methods routine in the art. Preferably, an inducible promoter (e.g., a glucocorticoid or a tetracycline response element) is also introduced into this construct so that ribozyme expression can be selectively controlled. For saturating use, a highly and constitutively active promoter can be used. tDNA genes (i.e., genes encoding tRNAs) are useful in this application because of their small size, high rate of transcription, and ubiquitous expression in different kinds of tissues. Therefore, ribozymes can be routinely designed to cleave virtually any mRNA sequence, and a cell can be routinely transformed with DNA coding for such ribozyme sequences such that a controllable and catalytically effective amount of the ribozyme is expressed. Accordingly the abundance of virtually any RNA species in a cell can be modified or perturbed.

Ribozyme sequences can be modified in essentially the same manner as described for antisense nucleotides, e.g., the ribozyme sequence can comprise a modified base moiety.

RNA aptamers can also be introduced into or expressed in a cell to modify RNA abundance or activity. RNA aptamers are specific RNA ligands for proteins, such as for Tat and Rev RNA (Good et al., 1997, Gene Therapy 4: 45-54) that can specifically inhibit their translation.

Gene specific inhibition of gene expression may also be achieved using conventional RNAi technologies. Numerous references describing such technologies exist and include, for example, WO 99/32619; Miller et al. Cell Mol Neurobiol 25:1195-207 (2005); Lu et al. Adv Genet 54:117-42 (2005).

Antisense molecules, triple helix DNA, RNA aptamers and ribozymes of the present invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding the genes discussed herein. Such DNA sequences may be incorporated into a wide variety of vectors with suitable RNA polymerase promoters such as T7 or SP6 according to conventional methods. Alternatively, cDNA constructs that synthesize antisense RNA constitutively or inducibly can be introduced into cell lines, cells, or tissues using methods familiar to one of skill in the art. Vectors may be introduced into cells or tissues by many available means, and may be used in vivo, in vitro or ex vivo. For ex vivo therapy, vectors may be introduced into stem cells taken from an animal and clonally propagated for autologous transplant back into that same animal. Delivery by transfection and by liposome injections may be achieved using methods that are well known in the art.

The instant invention also includes a method to identify an animal that might benefit from feeding a composition as disclosed herein comprising measuring the gene expression levels of any one or more genes listed in Tables 5-14 in said animal and comparing said levels to the gene expression levels seen in Tables 5-14 wherein an animal with levels different than those seen in Tables 5-14 (e.g., up regulated versus down regulated) would be identified as potentially benefiting from feeding a composition of the present invention.

It is also contemplated herein that the invention relates to methods for treating an animal suffering from disorders or disease associated with or relating to any one of more of the following biological pathways: blood clotting and platelet activation and aggregation, bone and muscle integrity, inflammatory responses, cartilage degradation and pain response, DNA damage and repair pathways, neural function, glycogen synthesis and degradation, glycolysis, gluconeogenesis, the pentose phosphate pathway and electron transport comprising administering to the animal a composition of the present invention.

This invention is not limited to the particular methodology, protocols, and reagents described herein because they may vary. Further, the terminology used herein is for the purpose of describing particular embodiments only and is not intended to limit the scope of the present invention. The terms "comprise", "comprises", and "comprising" are to be interpreted inclusively rather than exclusively.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, devices, and materials are described herein.

All patents, patent applications, and publications mentioned herein are incorporated herein by reference to the extent allowed by law for the purpose of describing and disclosing the compositions, compounds, methods, and similar information reported therein that might be used with the present invention. However, nothing herein is to be construed as an admission that the invention is not entitled to antedate such disclosure by virtue of prior invention.

In the specification there have been disclosed typical preferred embodiments of the invention and, although specific terms are employed, they are used in a generic and descriptive sense only and not for purposes of limitation, the scope of the invention being set forth in the following claims. Many modifications and variations of the present invention are possible in light of the above teachings. It is therefore to be understood that within the scope of the appended claims the invention may be practiced otherwise than as specifically described.

EXAMPLES

This invention can be further illustrated by the following examples of preferred embodiments thereof, although it will be understood that these examples are included merely for purposes of illustration and are not intended to limit the scope of the invention unless otherwise specifically indicated.

Example 1

A composition formulated for senior or super senior regular or small breed canines is described in Table 2.

TABLE 2

Ingredient Composition for Canine Regular or Small Breed Super Senior

| Ingredient | % of composition |
|---|---|
| Carbohydrate | 65.83 |
| Animal Protein | 14.31 |
| Vegetable Protein | 6.05 |
| Animal/Vegetable Fat | 6.60 |
| Omega Fat | 3.38 |
| Fiber | 1.42 |
| Minerals | 1.63 |
| Vitamins | 0.78 |

Example 2

A composition formulated for senior or super senior large breed canines is described in Table 3.

TABLE 3

Ingredient Composition for Canine Large Breed Super Senior

| Ingredient | % of composition |
|---|---|
| Carbohydrate | 65.15 |
| Animal Protein | 14.79 |
| Vegetable Protein | 6.45 |
| Animal/Vegetable Fat | 6.23 |
| Omega Fat | 4.12 |
| Fiber | 1.30 |
| Minerals | 0.91 |
| Vitamins | 1.05 |

Example 3

A composition formulated for senior or super senior felines is described in Table 4.

TABLE 4

Ingredient Composition for Feline Super Senior

| Ingredient | % of composition |
|---|---|
| Carbohydrate | 31.47 |
| Animal Protein | 25.57 |
| Vegetable Protein | 20.14 |
| Animal/Vegetable Fat | 13.31 |
| Omega Fat | 1.61 |
| Fiber | 4.80 |

TABLE 4-continued

Ingredient Composition for Feline Super Senior

| Ingredient | % of composition |
|---|---|
| Minerals | 1.77 |
| Vitamins | 1.34 |

Example 4

Genomic Analysis of Control vs. Super Senior Pet Food

To further characterize the nutritional benefits of the super senior pet food compositions of the present invention, gene expression profiles from animals fed the compositions compared to control animals are assayed and the results are described in detail below.

Materials and Methods:

Study Design:

Blood samples are drawn from 9 Beagles according to conventional methods before and after feeding for 14 days on Super Senior K9 diet (a total of 18 samples). Each sample taken after the 14 day trial is compared to its own control.

Isolation of Lymphocytes from Canine Blood

Reagents:

4 ml canine blood, heparin or EDTA tubes, Hank's Balanced Salt Solution (Gibco 14175-095), HEPES buffer (Gibco 15630-080), Accu-Paque (Accurate Chemical & Scientific Corp AN3100).

Materials/Equipment:

Transfer pipettes (VWR 14670-147), 14 ml centrifuge tubes w/caps, 9" Pasteur pipettes, 1.5 ml microcentrifuge tubes (VWR 20170-038), centrifuge tube racks, microcentrifuge tube rack, waste container, Beckman Coulter Allegra 25R Centrifuge, SN AJC01J015Eppendorf Centrifuge, 5417C.

Solutions:

Hank's Balanced Salt Solution (HBSS) w/25 mM HEPES buffer solution is made by adding 12.8 ml of HEPES buffer solution to a 500 ml bottle of HBSS. Hank's Balanced Salt Solution and Accu-Paque need to be removed from the refrigerator and placed at room temperature at least 30 minutes before beginning the lymphocyte isolation. Both solutions should be place back in the refrigerator (4° C.) immediately following their use. Procedure:
1. Measure 4 ml of HBSS w/HEPES into the correct number of 14 ml centrifuge tubes (one tube for each 4 ml draw of blood)
2. Using a transfer pipette, transfer 4 ml blood from the Vacutainer® tubes to the 14 ml centrifuge tube containing the HBSS w/HEPES.
3. Mix the sample well using the transfer pipette to pipette up and down for 30 seconds.
4. Insert a 9" Pasteur pipette into each of the 14 ml centrifuge tubes. Make sure the bottom tip of the Pasteur pipette touches the bottom of the tube.
5. Using a transfer pipette, slowly add 4 ml of Accu-Paque by running the liquid down the inside of the Pasteur pipette allowing gravity to layer the Accu-Paque under the diluted blood sample.
6. Plug the top of the Pasteur pipette using your finger and gently remove the pipette.
7. Centrifuge the tubes at 800×g for 20 minutes at room temperature. For puppy blood a longer centrifugation of 45 minutes is necessary to allow for a good separation of RBC's from WBC's.
8. Using a transfer pipette, carefully remove the top layer to within 0.5 cm of the middle opaque layer and discard.
9. Using a new transfer pipette, carefully remove the middle opaque layer and transfer to a 1.5 ml microcentrifuge tube. Be careful not to transfer any of the bottom layers.
10. Centrifuge the microcentrifuge tubes at 13,200 rpm for 3.5 minutes at room temperature.
11. Carefully remove the supernatant and flash freeze the remaining pellet (lymphocytes) in liquid nitrogen. Store the final samples at −80° C.

RNA Isolation:

Reagents:

Deionized $H_2O$, Absolute ethanol (Sigma E7023), RNA Storage Solution (Ambion 7000), RNase Zap® (Ambion 9780), Buffer RLT, Buffer RW1 and Buffer RPE (provided in the RNeasy Mini Kit).

Equipment/Materials:

RNeasy Mini Kit (Qiagen 74104), QIAshredder spin columns (Qiagen 79656), P1000 Pipetman pipette (Rainin), P200 Pipetman pipette (Rainin), 100-100 µl filtered pipette tips (USA Scientific 1126-7810), 1-200 µl filtered pipette tips (USA Scientific 1120-8810), sterile transfer pipettes (VWR 14670-147), 55 ml sterile solution basin (VWR 21007-974), 2 waste containers (one for liquid, one for tips/pipettes), 1.5 ml sterile microcentrifuge tubes (VWR 20170-038), Microcentrifuge tube rack, permanent marker, Eppendorf Microcentrifuge, model #5417C.

Procedure:
1. Loosen the pellet in the microcentrifuge tubes by thawing slightly and then flick the tube to dislodge the pellet.
2. Add the appropriate volume of Buffer RLT (in this case use 600 µl). Vortex or pipette to mix.
3. Transfer sample to a QIAshredder tube to homogenize the sample. Centrifuge for 2 minutes at 14,000 rpm. Discard spin column but keep the collection tube and its contents.
4. Add one volume (600 µl) of 70% ethanol to the homogenized lysate and mix by pipetting.
5. Apply a 600 µl aliquot of the sample to an RNeasy mini column placed in a 2 ml collection tube. Close tube gently and centrifuge for 15 sec at 14,000 rpm. Discard the flow-through. Add the second 600 µl aliquot of the cell lysate to the same spin column and repeat. Discard flow-through.
6. Reuse the collection tube from step 5. Add 700 µl Buffer RW1 to the column.

Centrifuge for 15 sec at 14,000 rpm. Discard the flow-through and collection tube.

7. Transfer the column to a new 2 ml collection tube and pipette 500 µl Buffer RPE onto the column. Centrifuge for 15 sec at 14,000 rpm to wash the column. Discard the flow-through but save the collection tube for step 8.
8. Add another 500 ml Buffer RPE to the column. Centrifuge for 2 min at 14,000 rpm to dry the membrane.
9. Transfer the column to a new 1.5 ml collection tube. Pipette 10 µl of RNA Storage Solution directly onto the membrane. Centrifuge for 1 min at 14,000 rpm to elute the RNA. Add a second volume of 5 µl of RNA Storage Solution directly to the membrane and spin for an additional minute. Store the final elution of RNA at −80° C.

RNA Probe Preparation and Hybridization.

Reagent:

Ovation TM Biotin System v1.0 for probe preps.

Protocol:

User Guide (Cat#D01002, version Oct. 27, 2004, NuGEN Technologies, Inc). The experimental procedure is followed as described in the user guide. All probe preparation starts with 50 ng of total RNA.

Genechip Procedures:

The Genechips used for the test is the Canine Genome 2.0 Array (Affymetrix). This Genechip contains 44,000 probe sets. Detailed sequence information for each unique probe identification number is available from the manufacturer.

Gene Expression Analysis:

Normalization is performed using MAS 5 provided in GCOS Affymetrix software (version 1.2). Expression levels for the genes analyzed are indicated on the tables included in the examples below, where an upward facing arrow refers to "up regulation" or increase and a downward facing arrow indicates "down regulation" in gene expression. Similarly, in some tables, upward or downward facing arrows also indicate increases or decreases in activity of certain proteins involved in a particular pathway, and are otherwise self explanatory.

Gene List Selection:

15,411 genes are selected for further analysis based on their "present" calls in at least 9 out of 18 samples.

Results of the gene chip analysis indicate that 1088 genes are differentially expressed between the control and Super Senior diet treated groups. The expression levels of these 1088 genes are statistically significant when grouped by 'diet'; using a parametric test where the variances is not assumed to be equal (Welch t-test). The p-value cutoff is 0.01 with no multiple testing correction. Under those selection criteria only about 154 genes would be expected to pass the restriction by chance. The genomic data is discussed in detail below.

Results:

Effect of Nutrition on Genes Associated with Pain and Inflammation

Based on an analysis of the gene chip data, at the P<0.01 level, 1,088 genes changed compared to control expression levels (10 were up regulated and the rest down regulated). At the P<0.001 level, data indicate that 35 genes are down regulated in beagles fed the super senior food. Nine of these down regulated genes are identified as related to the inflammatory and pain response. Down regulation of these genes may be predicted to result in pain relief, cartilage protection (less damage) and reduction in inflammatory responses. The compositions disclosed herein may be part of a therapeutic regimen to treat animals suffering from pain and/or inflammatory diseases. These genes and their putative role in inflammation and pain response are provided below in Tables 5-6.

TABLE 5

Genes involved in inflammation and pain response (P < 0.001)

| Sequence ID No. | Genes | Also Known As | Probe | Best Current BLAST Annotation | % match of probe sequence to BLAST hit | Probe Target Sequence |
|---|---|---|---|---|---|---|
| 1 | Phospholipase A2 | IPLA2GAMMA, IPLA2-2 | CfaAffx.6431.1.S1_s_at | PREDICTED: Canis familiaris similar to intracellular membrane-associated calcium-independent phospholipase A2 gamma; transcript variant 3 (LOC475880); mRNA | 100 | GGAGCCATGCATTTATG ACAGTCAAACGTGGGAA AATATTCTTAAGGACAG AATGGGATCCTCGCTAA TGATTGAAACAGCAAGA AACCCTTCATGTCCTAA GGATGGAGGTTTGCTTC TGAATAACCCTTCAGCG CTAGCAATGCACGAGTG CAAATGTCTTTGGCCTG ACGTCCCATTAGAGTGC ATTGTGTCCCTGGGCAC CGGGCGTTATGAGAGTG ATGTGAGAAACTCTGTG ACATCTACAAGCTTGAA AACCAAACTGTCTAATG TCATTAACAGTGCTACA GATACAGAAGAAGTCCA CGTAATGCTTGATGGTC TTTTACCTCCTGACACC TATTTTAGAT |
| 2 | Dipeptidase 2 | Putative dipeptidase | CfaAffx.31124.1.S1_at | PREDICTED: Canis familiaris similar to dipeptidase 2 (LOC611083); mRNA | 82.197 | GTGCTGCAATGCAACCT GTTAGCTAACGTGTCCA CTGTGGCAGTTCCCACG CATCCCTGCCCTGGAAG CCCCACAGTGCTGACTC TCCATCCCTCAGATCAC TTTGACTACATCAGGGC AGTCATTGGATCCAAGT TCATTGGAATTGGTGGA GATTATGATGGGGCCAG ACGTTTCCCTCAGGGGC TGGAGGATGTGTCCACA TACCCAGTTCTGATAGA GGAGTTGCTGAGGCGTG |

TABLE 5-continued

Genes involved in inflammation and pain response (P < 0.001)

| Sequence ID No. | Genes | Also Known As | Probe | Best Current BLAST Annotation | % match of probe sequence to BLAST hit | Probe Target Sequence |
|---|---|---|---|---|---|---|
| | | | | | | GCTGGAGTAGGGAAGAG CTCCAGGGTGTCCTTCG AGGAAACCTACTGCGGG TCTTTGGACAGGTGGAA CAGGTACGGGAGGCAAG CAAGGGGCAAAGGCCCT TGGAGGATGAGTTCCCG GATGAGCAGCTGAGCAG CTCTTGCCGCTCCGTTC TCTCACGTCTGCATCAG ACACAGTACCCTGCTCC ATACCAGAAACTAACTG AGATTTCACCTGAGTGG TCCCCTAAACAGTCATT GTCAAAATCTCTCCCCA TCATGGCCCCAGGCCTC ATAGTTATTGCTGCTTG T |
| 3 | Thromboxane synthase | Thromboxane A synthase 1, Thromboxane A synthase, Platelet, Cytochrome P450 subfamily V, CYP5, CYP5A1, Thromboxane synthatase, TXA synthase, TXS | CfaAffx.6939.1.S1_s_at | PREDICTED: Canis familiaris similar to Thromboxane-A synthase (TXA synthase) (TXS) (LOC482771); mRNA | 100 | ATCGCTGGCTATGAGAT CATCACCAACACGCTCT CTTTTGCCACCTACCTC CTGGCCACCAACCCTGA CTGCCAAGAGAAGCTTC TGGCAGAGGTGGACAGC TTTAAGGAGAAATATAC GGCCCTTGACTACTGCA GCCTCCAGGAAGGCCTG CCCTACCTGGACATGGT GATTGCGGAGACCTTGA GGATCTACCCCCCGGCT TTCAGGTTCACACGGGA GGCGGCGCGGGACTGCG AGGTGCGGGGACAGCGC ATCCCCGCGGGCGCCGT GGTGGAGGTGGCCGTGG GCGCCCTGCACCGTGAC CCTGAGTACTGGCCACA ACCGGAGACCTTCAACC CCGAGAGGTTCAAGGCC GAGGCGCAGCGACGACA GCAACCCTTCACCTACC TGCCGTTCGGCGCGGGC CCCCGGAGCTGCCTCGG GGTGCGGCTGGGGCTGC TGGAGGTCAAGCTGACG CTGCTGCAGGTCCTGCA CCAGTTCCGGTTCGAGG CCTGCCCGGAGACGCAG GTACCACTGCAGCTAGA CTCCAAATCTGCCCTAG GTCCAAAGAATGGCATC TACATCAAGATTGTCTC CCGCT |
| 4 | Ubiquitin conjugating enzyme E2D 3 | Ubiquitin protein ligase, Ubiquitin carrier protein, E2 (17) KB 3, Ubiquitin conjugating enzyme E2-17 kDa 3, UBC4/5, UBCH5C | CfaAffx.275.1.S1_s_at | PREDICTED: Pan troglodytes LOC461941 (LOC461941); mRNA | 97.19626 | GATTTGGCCCGTGACCC TCCAGCACAATGTTCTG CAGGTCCTGTTTGGGAT GATATGTTTCATTGGCA AGCCACAATTATAGGAC CTAATGACAGCCCATAT CAAGG |
| 5 | NEDD8 ultimate buster-1 | Neural precursor cell expressed, developmentally down | Cfa.12556.1.A1_s_at | PREDICTED: Canis familiaris similar to NEDD8 ultimate buster-1 (NY-REN-18 | 99.12473 | GGAATGGGCTACTCTAC TCATGCAGNCAAGCAGG NCCTGCATCAGGCCAGT GGGAACCTGGACGAAGC CCTGAAGATTCTTCTCA |

TABLE 5-continued

Genes involved in inflammation and pain response (P < 0.001)

| Sequence ID No. | Genes | Also Known As | Probe | Best Current BLAST Annotation | % match of probe sequence to BLAST hit | Probe Target Sequence |
|---|---|---|---|---|---|---|
| | | regulated 8, Ubiquitin like protein NEDD8 | | antigen) (LOC475542); mRNA | | GCAATCCTCAGATGTGG TGGTTAAATGATTCAGA TCCTGAAACGANCAACC AGCAAGAAAGTCCTTCC CAGGAAAACATTGACCA ACTGGTGTACATGGGCT TCGACGCTGTGGTGGCT GATGCTGCCTTGAGAGT GTTCAGGGGAAACGTGC AGCTGGCAGCTCAGNCC CTCGCCCACAACGGAGG AACTCTTCCTCCTGACC TGCAGCTCTTGGTGGAA GACTCTTCATCAACGCC ATCCACGTCCCCTTCCG ACTCCGCAGGTACCTCT AGTGCCTCAACAGATGA AGATATGGAAACCGAAG CTGTCAATGAAATACTG GAAGATATTCCAGAACA TGAAGAAGATTATCTTG ACTCAACACTGGAAG |
| 6 | Mitogen-activated protein kinase 14 (p38) | p38, Mitogen activated protein kinase 14, Cytokine suppressive antiinflammatory drug binding protein 1, CSBP1, CSAID binding protein 1, Stress activated protein kinase 2A, SAPK2A, p38 MAP kinase, p38 alpha, RK, MXI2, Cytokine suppressive antiinflammatory drug binding protein 2, CSBP2, CSAID binding protein 2 | CfaAffx.2947.1.S1_at | Homo sapiens mitogen-activated protein kinase 14, transcript variant 2; mRNA (cDNA clone MGC: 34610 IMAGE: 5181064); complete cds | 97.84946 | GAGATGGAGTCCTGAGC ACCTGGTTTCTGTTTTG TTGATCCCACTTCACTG TGAGGGGAAGGCCTTTT CATGGAACTCTCCAAA TATCATTC |
| 7 | Matrix metalloproteinase 19 (MMP-19) | MMP 19 | Cfa.4573.1.A1_at | Homo sapiens cDNA FLJ38021 fis; clone CTONG2012847 | 48.93048 | GTAGTTGATTCCTGGTT CGCCTTTCCTCTTGGGT CCCATAGGTTCGAATCC CCTTCTACCTCAGTCGG GAGTACTGTCCTCCATG GTGCTTCCCTTCCTCTC CTTAATGTGGGGAAGAC CATGGGGCAATGCATGG CGCAGGACCTGCCTCCC CCAAAAGCAGTCTACTT GCTCCACGGAGAGAGAA CTGGGTCCACGTGCCAG AGTCTTGCCCTTTGGCC CAGAGTAGCCTGGTCTT CATGGCTGTATGGGAGA CAAGTGCCTTCTCTGCT TCTTGTTGTAGGTGATG CTAATCTCCTTAACCAA ACCTTTGTCCCAGCCGC TAATCTGTTCTAACTCT CCCTCCTCNTGATTCTC CTGCTCAAAGTCTGTTC |

TABLE 5-continued

Genes involved in inflammation and pain response (P < 0.001)

| Sequence ID No. | Genes | Also Known As | Probe | Best Current BLAST Annotation | % match of probe sequence to BLAST hit | Probe Target Sequence |
|---|---|---|---|---|---|---|
| 8 | Tissue Inhibitor of metalloproteinases (TIMP-1) | TIMP-1 | Cfa.3680.1.S1_s_at | Canis familiaris TIMP metallopeptidase inhibitor 1 (TIMP1); mRNA | 99.4 | AGATGTTCAAGGGTTTC AGCGCCTTGGGGAATGC CTCGGACATCCGCTTCG TCGACACCCCGCCCTG GAGAGCGTCTGCGGATA CTTGCACAGGTCCCAGA ACCGCAGCGAGGAGTTT CTGGTCGCCGGAAACCT GCGGGACGGACACTTGC AGATCAACACCTGCAGT TTCGTGGCCCCGTGGAG CAGCCTGAGTACCGCTC AGCGCCGGGGCTTCACC AAGACCTATGCTGCTGG CTGTGAGGGGTGCACAG TGTTTACCTGTTCATCC ATCCCCTGCAAACTGCA GAGTGACACTCACTGCT TGTGGACGGACCAGTTC CTCACAGGCTCTGACAA GGGTTTCCAGAGCCGCC ACCTGGCCTGCCTGCCA AGAGAGCCAGGGATATG CACCTGGCAGTCCCTGC GGCCCCGGATGGCCTAA ATCCTACTCCCCGTGGA AGCCAAAGCCTGCACAG TGTTCACCCCACTTCCC ACTCCTGTCTTTCTTTA TCCAAAA |
| 9 | Fatty acid amide hydrolase (FAAH) | Oleamide hydrolase Anandamide amidohydrolase FAAH | CfaAffx.7308.1.S1_x_at | PREDICTED: Canis familiaris similar to Ubiquinol-cytochrome c reductase complex 11 kDa protein; mitochondrial precursor (Mitochondrial hinge protein) (Cytochrome C1; nonheme 11 kDa protein) (Complex III subunit VIII); transcript variant 2 (LOC608530); mRNA | 63.33333 | GAAGTGGAGTAGGTGCC GCTGTTGCTGCTGGTGT TGAATTCAGAACTGTAG CGGGACATGGGGCTGGA GGACGAGCAAAAGATGC TGACCGGGTCCGGAGAT CCCAAGGAGGATCCCCT AACAACAGTGAGAGAGC AATGCGAGCAGCTGGAG AAATGTGTAAAGGCTCG GGAGCGGCTAGAGCTCT GTGACCAGCGTGTATCC TCCAGGTCACAGACAGA GGAGGATTGCACAGAGG AGCTCTTTGACTTCCTG CATGCAAGGGACCACTG TGTGGCCCACAAACTCT TTAACAGCTTG |

TABLE 6

Summary of down-regulated enzyme roles involved in the eicosanoid pathway (inflammatory response)

| Gene | Gene Expression Compared to Control | Results in | Role |
|---|---|---|---|
| Phospholipase A$_2$ | ↓ | ↓ in arachidonic release from phospholipids | ↓ in 2-series inflammatory response |
| Thromboxane synthase | ↓ | ↓ Thromboxane A$_2$ | ↓ platelet aggregation, vasoconstriction, lymphocyte proliferation and bronchoconstriction |
| Dipeptidase 2 | ↓ | ↓ Thromboxane B$_2$ | ↓ vasoconstriction |
|  | ↓ | ↓ Leukotriene E$_4$ | ↓ component of slow-reactive substance of anaphylaxis, micro-vascular vasoconstrictor and bronchoconstriction |

TABLE 6-continued

Summary of down-regulated enzyme roles involved in the eicosanoid pathway (inflammatory response)

| Gene | Gene Expression Compared to Control | Results in | Role |
|---|---|---|---|
| Ubiquitin conjugating enzyme E2D 3 (and NEDD8 ultimate buster-1) | ↓ | ↓ ubiquination or activation of TAK1, IRAK and TRAF | ↓ MMP Production |
| Mitogen activated protein kinase 14 (p38) | ↓ | ↓ in c-Jun promotor | ↓ MMP Production |
| MMP-19 | ↓ | ↓ MMP-19 | ↓ in T-cell derived MMP-19 which has been implicated in rheumatoid arthritis |
| TIMP-1 | ↓ | ↓ TIMP-1 | Deactivates MMP's concentration is directly related to MMP concentration |

TABLE 6-continued

Summary of down-regulated enzyme roles involved in the eicosanoid pathway (inflammatory response)

| Gene | Gene Expression Compared to Control | Results in | Role |
|---|---|---|---|
| Fatty acid amide hydrolase | ↓ | ↑ anandmide | ↓ pain response |

Effect of Nutrition on Genes Involved in Heart Health and Blood Coagulation

At the $P<0.001$ and $P<0.01$ level, 12 genes are identified to be related to heart health through regulation of the eicosanoid pathway and blood coagulation pathway. The genes are responsible for blood coagulation through platelet activation and aggregation. The down regulation of these genes through nutrition can prevent inappropriate blood clotting which may result in heart or brain related disorders. The compositions of the present invention may be part of a therapeutic regimen to treat animals suffering from disorders or diseases of the blood, heart or brain. These genes and their putative role in vivo are described in Tables 7 and 8 below.

TABLE 7

Genes involved in heart health and blood coagulation

| Sequence ID No. | Gene | Probe | P-value | Best current BLAST annotation | % match of probe sequence to BLAST hit | Probe Target Seq. |
|---|---|---|---|---|---|---|
| 10 | Glycoprotein Ib | Cfa.3503.1.S1_at | <0.01 | *Canis familiaris* glycoprotein Ib mRNA; complete cds | 98.57143 | TGTGGGTCCGAGCTAACAGCT ACGTGGGGCCTCTGATGGCAG GACGGCGGCCCTCTGCCCTGA GCCTGGGTCGTGGGCAGGACC TGCTAGGTACGGTGGGCGTTA GGTACTCCAGCCACAGCCTCT GAGGCGACGGTGGGCAGTTTG GGGACCTTGAGAGGCTGTGAT GGGCCCTCCTATCAGGATCTT GCTGGGGTGGGTGGGCAGGG AGCACAGGATTGGGGGGAGGC CTTAAGCACCTTTTCTGGGTC AGAAGCCTCCTCTCCGCATTG CATGTGCAACCTCAGTGAAGC AGCATGGGCAGGGGAGCCGGA CGGGCCACCCAACAGAGCTCC TTATGCTGCAGGAGGGGTTCA CAGACCACTCGGACATCACCA TCACCTTGGGGGGGTGCTTG AGGGAAAAGCAAATTGAACAG AGCGTGATTCTCACGTGCAGG TACCTAAGGGAACTGGGGAAG AGATGCACCAAGACGAGAGCC CTCGTCATCCCTGGGGAGCCC AAGCCTAGGGGTTTTCTTCCT CTTCCCGTTTAGCATTTTCCA CCATCGTATGTTAC |
| 11 | Platelet glycoprotein VI | CfaAffx.4809.1.S1_at | <0.01 | PREDICTED: *Canis familiaris* similar to glycoprotein VI | 50 | AGTTTTGACCAATTCGCTCTG TACAAGGAGGGGACACTGAG CCCCACAAGCAATCTGCAGAA CAGTACTGGGCCAATTTCCCC |

TABLE 7-continued

Genes involved in heart health and blood coagulation

| Sequence ID No. | Gene | Probe | P-value | Best current BLAST annotation | % match of probe sequence to BLAST hit | Probe Target Seq. |
|---|---|---|---|---|---|---|
| | | | | (platelet) (LOC484303); mRNA | | ATCACCGCAGTGACTGTTGCC CACAGTGGGATCTACCGATGC TATAGCTTTTCCAGCAAGTTC CCGTACCTGTGGTCAGCCCCC AGCGACCCCCTGGAGCTTGTG GTAACAGGTGAGGGAGATGCA GTCCAAGCCTTTCTTCTTCAG CTCTTGCATACTCTGGTGGAA GTTCCAGGGGAGGGGCCAACA GTGCCTTCTAGGACTATCACT GTCTCTCCAAAGGGGTCAGAC TCTCCAACTGGTCTTGCTCAC CAGCACTACACCAAGGGCAAT CTGGTCCGGATATGCCTTGGA GCTGTGATTCTAATACTCCTG GTGGGAATTCTGGCAGAAGAT TGGCACAGCAGAAAGAAACCC CTGTTGCTCCGGGTCAGAGCT GTCCACAGGCCACTCCCACCC CTCCCACAGACCCAGAAACCA CACAGTCATCAGGATGGGGGT CGACCAGATGGCCATAACCAT |
| 12 | Platelet glycoprotein IX precursor | CfaAffx.7430.1.S1_at | <0.01 | PREDICTED: Canis familiaris similar to Platelet glycoprotein IX precursor (GPIX) (CD42A) (LOC609630); mRNA | 100 | TCTGGGCTGCCACGGAGGCCA CCAACGACTGCCCCGCAGAGT GCACCTGCCAGACCCTGGAGA CCATGGGGCTGTGGGTGGACT GCAGGGGGCGGGGACTCAAGG CCCTGCCCGCCCTGCCGGTCC ACACCCGCCACCTCCTGCTGG CCAATAACAGCCTCCGCTCCG TGCCCCTGGTGCCTTCGACC ACCTGCCTGGGCTGCAGATCC TCGACGTGATGCACAACCCCT GGCACTGTGACTGCAGCCTCA CCTACCTGCGTCTCTGGCTGG AGGACCACACGCCCGAGGCCT TGCTGCAGGTCCGCTGTGCCA GCCCCGCGCTGGCCACCACCC GGCCGCTGGGCTGGCTGACGG GCTACGAGCTGGGCAGCTGCG GCTGGCAGCTACAGGCACCCT GGACCTA |
| 13 | Coagulation factor XIII A chain precursor | CfaAffx.14964.1.S1_s_at | <0.01 | PREDICTED: Canis familiaris similar to Coagulation factor XIII A chain precursor (Coagulation factor XIIIa) (Protein-glutamine gamma-glutamyltransferase A chain) (Transglutaminase A chain); transcript variant 1 (LOC478711); mRNA | 99.6008 | ATCTCTCAGGCAACATCGTCT TCTACACCGGGGTCTCCAAGA CGGAATTCAAGAAGGAGACAT TTGAAGTGACACTGGAGCCCT TGTCTTTCAAGAGAGAGGAGG TGCTGATCAGAGCGGGCAGT ACATGGGCCAGCTGCTAGAGC AAGCATACCTGCACTTCTTTG TCACAGCGCGTGTCAATGAGT CCAAGGATATTCTGGCCAAGC AGAAGTCCACCGTGCTGACGA TCCCCCAGCTCATCATCAAGG TCCGTGGCGCCAAGATGGTTG GTTCTGACATGGTGGTGACAG TTGAGTTCACCAATCCCCTGA AGAAACTCTGCGGAATGTGT GGATACACCTGGATGGTCCTG GAGTGATAAAGCCAATGAGGA AGATGTTCCGTGAAATCCAGC CCANTGCCACCATACAATGGG AAGAAGTGTGTCGACCCTGGG TGTCTGGCCCTCGGAAGCTGA TAGCCAGCATGACGAGTGACT CCCTGAGACACGTGTATG |
| 3 | Thromboxane synthase | CfaAffx.6939.1.S1_s_at | <0.001 | PREDICTED: Canis familiaris similar to Thromboxane-A | 100 | ATCGCTGGCTATGAGATCATC ACCAACACGCTCTCTTTTGCC ACCTACCTCCTGGCCACCAAC CCTGACTGCCAAGAGAAGCTT |

TABLE 7-continued

Genes involved in heart health and blood coagulation

| Sequence ID No. | Gene | Probe | P-value | Best current BLAST annotation | % match of probe sequence to BLAST hit | Probe Target Seq. |
|---|---|---|---|---|---|---|
| | | | | syhthase (TXA synthase) (TXS) (LOC482771); mRNA | | CTGGCAGAGGTGGACAGCTTT AAGGAGAAATATACGGCCCTT GACTACTGCAGCCTCCAGGAA GGCCTGCCCTACCTGGACATG GTGATTGCGGAGACCTTGAGG ATCTACCCCCCGGCTTTCAGG TTCACACGGGAGGCGGCGCGG GACTGCGAGGTGCGGGACAG CGCATCCCCGCGGGCGCCGTG GTGGAGGTGGCCGTGGGCGCC CTGCACCGTGACCCTGAGTAC TGGCCACAACCGGAGACCTTC AACCCCGAGAGGTTCAAGGCC GAGGCGCAGCGACGACAGCAA CCCTTCACCTACCTGCCGTTC GGCGCGGGCCCCCGGAGCTGC CTCGGGGTGCGGCTGGGGCTG CTGGAGGTCAAGCTGACGCTG CTGCAGGTCCTGCACCAGTTC CGGTTCGAGGCCTGCCCGGAG ACGCAGGTACCACTGCAGCTA GACTCCAAATCTGCCCTAGGT CCAAAGAATGGCATCTACATC AAGATTGTCTCCCGCT |
| 14 | Dystrobrevin binding protein 1 isoform a | CfaAffx.15541.1.S1_s_at | <0.01 | PREDICTED: Canis familiaris similar to dystrobrevin binding protein 1 isoform a (LOC610315); mRNA | 99.65986 | GGCAACATGTCGTCCATGGAG GTCAACATCGACATGCTGGAG CAGATGGACCTGATGGACATC TCTGACCAGGAGGCCCTGGAC GTCTTCCTGAACTCCGGCGCT GAAGCAACACGGTGCCGTCT CCGGTCTCAGGGCCTGGCTCG GGGGACAGTCGGCAGGAAATC ACGCTCCGGGTTCCAGATCCC GCCGAATCGCAAGCTGAGCCT CCTCCCTCGCCGTGTGCCTGT CCTGAGCTGGCCGCCCCGGCC CCCGGCGACGGTGAGGCCCCC GTGGTCCAGTCTGACGAGGAG |
| 15 | Integrin beta-7 precursor | Cfa.11961.1.A1_s_at | <0.01 | PREDICTED: Canis familiaris similar to Integrin beta-7 precursor (LOC477598); mRNA | 99.0909 | ATTACAACGTGACTCTGGCTT TGGTCCCTGTCCTGGATGACG GCTGGTGCAAAGAGAGGACCC TAGACNAACCAGCTGCTGTTC TTCCTGGTGGAGGAGGAANCC GGAGGCATGGTTGTGTTGACA GTGAGACCCCAAGAGAGAGGC GCGGATCACACCCAGGCCATC GTGCTGGGCTGTGTAGGGGGC ATCGTGGCAGTGGGGCTGGGG CTGGTCCTGGCTTACCGGCTC TCTGTGGAAATCTACGNCCGC CGAGAATTTAGCCGCTTTGAG AAGGAGCAGAAGCACCTCAAC TGGAAGCAGGAAAACAATCCT CTCTACAGAAGCGCC |
| 16 | integrin-linked kinase | Cfa.465.1.S1_s_at | <0.01 | PREDICTED: Canis familiaris similar to integrin linked kinase; transcript variant 1 (LOC476838); mRNA | 100 | TGGGCGCATGTATGCACCTGC CTGGGTGGCCCCTGAAGCTCT GCAGAAGAAGCCTGAAGATAC AAACAGACGCTCAGCAGATAT GTGGAGTTTTGCAGTGCTTCT GTGGGAACTGGTGACGAGGGA GGTACCCTTTGCTGACCTCTC CAACATGGAGATTGGAATGAA GGTGGCACTGGAAGGCCTTCG GCCTACTATCCCACCAGGCAT TTCCCCCCATGTGTGTAAGCT CATGAAGATCTGCATGAATGA AGACCCTGCTAAGCGGCCCAA GTTTGACATGATTGTGCCTAT CCTGGAGAAGATGCAGGACAA GTAGAGCTGGAAAGCCCTTGC |

TABLE 7-continued

Genes involved in heart health and blood coagulation

| Sequence ID No. | Gene | Probe | P-value | Best current BLAST annotation | % match of probe sequence to BLAST hit | Probe Target Seq. |
|---|---|---|---|---|---|---|
| | | | | | | CTAAACTCCAGAGGTGTCAGG ACACGGTTAGGGGAGTGTGTC TCCCCAAAGCAGCAGGC |
| 17 | Thrombospondin 1 | Cfa.21204.1.S1_at | <0.01 | PREDICTED: *Canis familiaris* similar to thrombospondin 1 precursor (LOC487486); mRNA | 54.83871 | ATACGAATGCAGAGATTCCTA ATCAAACTGTTGATCAAAAGA CTGATCCTAACCAATGCTGGT GTTGCACCTTCTGGAACCACG GGCTTAAGAAAACCCCCAGGA TCACTCCTCCCTGCCTTTTCT CTGCTTGCATATCATTGTGGA CACCTAGAATACGGGACTTGC CTCGAGACCATGCNNNNNTCC AAATCAGACTNNNNNNGTAGC CTCTGAACGCGAAGAGAATCT TCCAAGAGCATGAACAG |
| 18 | Thrombospondin repeat containing 1 | CfaAffx.18675.1.S1_s_at | <0.01 | PREDICTED: *Canis familiaris* similar to extracellular matrix protein 1 isoform 1 precursor (LOC808791); mRNA | 100 | GAAGCCCTTGATGGATACTGT GAACGGGAACAGGCTATAAAG ACCCACCACCACTCCTGTTGC CACCACCCTCCTAGCCCTGCC CGCGATGAGTGCTTTGCCCGT CAGGCGCCATACCCCAACTAT GACCGGGACATCCTGACCCTT GATTTCAGCCAAGTTACCCCC AACCTCATGCAACATCTCTGT GGAAATGAAGACTTCTCACC AAGCATAAACAGATTCCTGGG CTGATCCGGAACATGACTGCC CACTGCTGTGACCTGCCATTT CCAGAGCAGGCCTGCTGTGCT GAGGAGGAGAAATCGGCCTTC ATTGCAGACTTGTGTGGTTCC CGACGTAACTTCTGGCGAGAC TCTGCCCTCTGCTGTAACCTG AATCCTGGAGATGAACAGACC AACTGCTTCAACACTTATTAT CTGAGGAATGTGGCTCTAGTG GCTGGAGACAAT |
| 19 | Thrombospondin type 1 motif, 17 | CfaAffx.16694.1.S1_at | <0.01 | PREDICTED: *Canis familiaris* similar to lines homolog 1 isoform 1 (LOC607902); mRNA | 98.13084 | TGGTTGTAGCTCCTCACTTGT CCAAGACCGAAGCAGCAACCA AACTGAACTTAGCCTTTGGGC TGCTCTTGGTAGTCACAGAAA TGCCCACGCTTCAGTCCCCTG GGCTTCCAATGCTTCTGGACC TCTGAACCAGCCTGTGATGTC CAAGGAACCCCACGTCACGCT CCAGGCTGCTGCTGGTCTGTC TCCCCCACAAGCTTCTCAAAG TCTGGTAGATTATGACAGCTC TGATGATTCTGAAGTAGAAGT CACAGACCAGCACTCAACAAA CAGTAAACAAACATCTTTACA GCAAGAAGCAAAGAAGAAATT TCAGGACACAGTTAGAACAGG TCCAGATGAAAAAGAACTTAG CATGGAGCCTCAATCAAGGCC TCTGGTTCCAGAACAATCTAA TATTAATATTCCCTTCTCTGT TGACTGTGACATCTCCAAAGT AGGAATATCTTACAGGACACT GAAGTGCTTTCAGGAGCTACA GGGTGCCATTTACCGTTTGCA GAAAAAAATCTTTTCCCCTA TAATGCCACA |
| 20 | Angio-associated migratory cell protein (AAMP) | Cfa.8616.1.A1_s_at | <0.001 | *Canis familiaris* angio-associated migratory cell protein (AAMP) gene; complete cds | 64.77273 | GCGGACTGTGTTCCAACCCCT TCAGCCGACTTGCCCCCTCCG TCCCTTCTCTTAAGAGACCCA TCCCTTGGCCCCCCACCCCAC CCTCACCCAGACCTGCGGGTC CCTCAGAGGGGGGTCAGGCCT |

TABLE 7-continued

Genes involved in heart health and blood coagulation

| Sequence ID No. | Gene | Probe | P-value | Best current BLAST annotation | % match of probe sequence to BLAST hit | Probe Target Seq. |
|---|---|---|---|---|---|---|
| | | | | | | CTTTCTCTTTCACCTTCATTT GCTGGCGTGAGCTGCGGGGGT GTGTGTTTGTATGTGGGGAGT AGGTGTTTGAGGTTCCCGTTC TTTCCCTTCCCAAGTCTCTGG GGGTGGAAAGGAGGAAGAGAT ATTAGTTACAGA |

TABLE 8

Summary of down regulated enzyme roles involved in heart health and blood coagulation

| Gene | Gene Expression compared to Control | Role |
|---|---|---|
| Glycoprotein Ib | ↓ | GP-Ib, a surface membrane protein of platelets, participates in the formation of platelet plugs by binding to the A1 domain of von Willebrand factor, which is already bound to the subendothelium. |
| Platelet glycoprotein VI | ↓ | Collagen receptor belonging to the immunoglobulin-like protein family that is essential for platelet interactions with collagen |
| Platelet glycoprotein IX precursor | ↓ | The GPIb-V-IX complex functions as the von Willebrand factor receptor and mediates von Willebrand factor-dependent platelet adhesion to blood vessels. The adhesion of platelets to injured vascular surfaces in the arterial circulation is a critical initiating event in hemostasis |
| Coagulation factor XIII A chain precursor | ↓ | Factor XIII is activated by thrombin and calcium ion to a transglutaminase that catalyzes the formation of gamma-glutamyl-epsilon-lysine cross-links between fibrin chains, thus stabilizing the fibrin clot. |
| Thromboxane synthase | ↓ | ↓ platelet aggregation, vasoconstriction, lymphocyte proliferation and bronchoconstriction |
| Angio-associated migratory cell protein (AAMP) | ↓ | contains a heparin-binding domain (dissociation constant, 14 pmol) and mediates heparin-sensitive cell adhesion |
| Dystrobrevin binding protein 1 isoform a | ↓ | Plays a role in the biogenesis of lysosome-related organelles such as platelet dense granule and melanosomes |
| Thrombospondin 1 | ↓ | Adhesive glycoprotein that mediates cell-to-cell and cell-to-matrix interactions. Can bind to fibrinogen, fibronectin, laminin, type V collagen and integrins alpha-V/beta-1, alpha-V/beta-3 and alpha-IIb/beta-3. |
| Thrombospondin type 1 motif, 17 | ↓ | Metalloprotease activity |
| Thrombospondin repeat containing 1 | ↓ | |
| Integrin beta-7 precursor | ↓ | Integrin alpha-4/beta-7 (Peyer's patches-specific homing receptor LPAM-1) is expected to play a role in adhesive interactions of leukocytes. It is a receptor for fibronectin and recognizes one or more domains within the alternatively spliced CS-1 region of fibronectin. Integrin alpha-4/beta-7 is also a receptor for MADCAM1 and VCAM1. It recognizes the sequence L-D-T in MADCAM1. Integrin alpha-E/beta-7 (HML-1) is a receptor for E-cadherin. |
| Integrin linked kinase | ↓ | Receptor-proximal protein kinase regulating integrin-mediated signal transduction. May act as a mediator of inside-out integrin signaling. Focal adhesion protein part of the complex ILK-PINCH. This complex is considered to be one of the convergence points of integrin- and growth factor-signaling pathway. Could be implicated in mediating cell architecture, adhesion to integrin substrates and anchorage-dependent growth in epithelial cells. Phosphorylates beta-1 and beta-3 integrin subunit on serine and threonine residues, but also AKT1 and GSK3B. |

Effect of Nutrition on Genes Involved with Muscle and Bone Regulation

Ten down regulated genes are identified as related to body composition through regulation of bone and muscle. The genes spare muscle and bone deterioration by reducing nitric oxide production and glucocorticoid degradation of muscle. Down regulation of these genes results in a decrease in nitric oxide production and glucocorticoid response. The compositions disclosed herein may be part of a therapeutic regimen to treat animals suffering from diseases or disorders associated with or relating to muscle or bone. These genes and their putative role in muscle and bone regulation are detailed in Tables 9 and 10 below.

TABLE 9

Genes involved in muscle and bone regulation

| Sequence ID No. | Gene | Probe | P-value | Best current BLAST annotation | % match of probe sequence to BLAST hit | Probe Target Sequence |
|---|---|---|---|---|---|---|
| 21 | Capping Protein | Cfa.1044.1.S1_at | 0.001 | PREDICTED: Canis familiaris similar to F-actin capping protein beta subunit (LOC478209); mRNA | 44.87179 | AGGTCCCGTAACACCGGCATCGCG ACCGCACAGCGCCATCTCCCCAGA ATAAAGCCCAGTAAACACCCCTGN NNNNNANNNNNANNNNNCACCACG TTTTGCTATCAGAACTCTCCTTGT TTCCAGAGCCCGTGTGCTTTTGTT TGCCCCAGCCCC |
| 22 | Calmodulin | Cfa.4168.1.S1_at | 0.01 | PREDICTED: Canis familiaris similar to calmodulin 1; transcript variant 3 (LOC480416); mRNA | 52.54237 | CCACCCATGGTGACGATGACACAC ATCCTGGTGGCATGCGTGTGTTGG TTTAGCGTTGTCTGCGTTGTACTA GAGCGAAAATGGGTGTCAGGCTTG TCACCATTCACACAGAAATTTAAA AAAAAAAAAAAAANNNNGANAAAA AACCTTTACCAAGGGAGCATCTTT GGACTCTCTGTTTTTAAAACCTCC TGAACCATGACTTGGAGCCAGCAG ATTAGGCTGTGGCTGTGGACTTCA GCACAACCATCAACATTGCTGATC AAGAAATTACAATATACGTCCATT CCAAGTT |
| 23 | Dynein | Cfa.4942.1.A1_s_at | 0.001 | PREDICTED: Canis familiaris similar to dynein; cytoplasmic; heavy polypeptide 2; transcript variant 2 (LOC479461); mRNA | 99.6016 | ATACCTCAGAGGTCTCGTAGCTCG TGCCCTTGCCATCCAGAGCTGGGT GGNAGAGAGCTGAGAAGCAGGCTC TTTTCTCTGATACACTCGACCTGT CAGAACTCTTCCACCCAGACACAT TTCTCAATGCTCTTCGCCAGGAAA CAGCAAGGGTGATGGGCTGCTCTG TGGATAGCCTTAAGTTTGTAGCTT CGTGGAAAGGTCGGCTGCAAGAAG CAAAGCTGCAGATCAAGATGGGCG GCTTGCTTCTGGAAGGCTGCAGTT TTGACGGGAGCCGGCTCTCTGAAA ACCACCACGATTCTCCAAGTGTGT CACCAGTTCTCCCTTGCTGTGTTG GCTGGATTCCCCAGGGTGCATATG GTCCCTATTCTCCTGACGAGTGCA TATCTCTGCCCGTGTACACGAGCG CTGAGAGGGATCGTGTGGTAGCCA ACATCGACGTCCCGTGTGGGGGCA NCCAAGACCAGTGGATTCAGTGTG GAGCCGCTCTGTTTCTAAAAAA |
| 24 | Dynactin | Cfa.1807.1.S1_at | 0.01 | PREDICTED: Canis familiaris similar to dynactin 3 isoform 2; transcript variant 1 (LOC474750); mRNA | 100 | AGGACGACAAGGCTCAGGACGCAA AGTGTGAAACTGCCTTTGTAACAG GGCAGAAGCAGCTCTGTATTGGAT TCACAACCTACCTATCTGCATTCA GGTGGGGCTCGGAGGTCAGAGGTC TGGCTACTTGAGGTTTGCTGTTTG CAC |
| 25 | Kinesin | Cfa.10496.1.S1_s_at | 0.01 | PREDICTED: Canis familiaris similar to Kinesin-like KIF2 (Kinesin-2) (HK2); transcript variant 5 (LOC478071); mRNA | 99.73046 | AGCCACAGCATTTCCTTTTAACTT GGTTCAATTTTTGTAGCAAGACTG AGCAGTTCTAAATCCTTTGCGTGC ATGCATACCTCATCAGTGNACTGT ACATACCTTGCCCTCTCCCAGAGA CAGCTGTGCTCACCTCTTCCTGCT TTGTGCCTTGACTAAGGCTTTTGA CCCTAAATTTCTGAAGCACAGCCA AGATAAAGTACATTCCTTAATTGT CAGTGTAAATTACCTTTATTGTGT GTACATTTTTACTGTACTTGAGAC ATTTTTTGTGTGTGACTAGTTAAT TTTGCAGGATGTGCCATATCATTG AATGGAACTAAAGTCTGTGACAGT GGACATAGCTGCTGGACCATTCCA TCTTACATGTA |

TABLE 9-continued

Genes involved in muscle and bone regulation

| Sequence ID No. | Gene | Probe | P-value | Best current BLAST annotation | % match of probe sequence to BLAST hit | Probe Target Sequence |
|---|---|---|---|---|---|---|
| 26 | Heat Shock Protein 1 (HSP90) | CfaAffx.11022.1.S1_s_at | 0.01 | PREDICTED: *Canis familiaris* similar to Heat shock pro-protein HSP 90-beta (HSP 84) (Tumor specific transplantation 84 kDa antigen) (TSTA) (LOC611252); mRNA | 100 | GGTGCTACTGTTTGAAACAGCTCT ACTCTCCTCCGGCTTCTCACTGGA GGATCCCCAGACTCACTCCAACCG CATTTACCGCATGATAAAGCTAGG CCTGGGCATCGATGAAGATGAAGT GGCAGCGGAGGAACCCAGTGCTGC TGTTCCTGATGAGATCCCTCCACT TGAGGGTGATGAGGATGCCTCTCG CATGGAAGAAGTC |
| 27 | PPlase | CfaAffx.1740.1.S1_at | 0.01 | PREDICTED: *Canis familiaris* similar to Peptidyl-prolyl cis-trans isomerase C (PPLASE) (Rotamase) (Cyclophilin C) (LOC481480); mRNA | 100 | GACATCACCAGTGGAGACGGCACC GGCGGTATAAGCATTTATGGTGAG ACGTTTCCAGATGAAAACTTCAAA CTGAAGCATTATGGCATTGGTTGG GTCAGCATGGCCAACGCTGGGCCT GACACCAACGGCTCTCAGTTCTTT ATCACCTTGACCAAGCCCACTTGG TTGGATGGCAAACATGTGGTATTT GGAAAAGTCCTTGATGGAATGACT GTGGTCCACTCCATAGAACTTCAG GCAACCGATGGGCACG |
| 28 | Calcinuerin | Cfa.19761.1.S1_at | 0.001 | PREDICTED: *Canis familiaris* similar to protein phosphatase 3 (formerly 2B); catalytic subunit; beta isoform (calcineurin A beta); transcript variant 5 (LOC479248); mRNA | 98.83382 | GAATTAACAATCTGCTTGAGCCCC AAAACACTACTTATGCACTTCACT TGCCAAAAGATTTGNGCAAGGTTT TGTACCCTGGTAAATGATGCCAAA GTTTGTTTTCTGTGGTGTTTGTCA AATGTTCTATGTATAATTGACTGT CTGTAACATGCTGTTTNCTTCCTC TGCAGATGTAGCTGCTTTCCTAAA TCTGTCTGTCTTTCTTTAGGTTAG CTGTATGTCTGTAAAAGTATGTTA AATTAAATTACTCTATCAGACGCT TGTCTGTCTTTTGATGTAGAAGCA ACTTTGTAGCACCTTGTTTTGAGG TNNGCTGCATTTGTTGCTGTACTT TGTGCAT |
| 29 | Protein kinase C | CfaAffx.408.1.S1_s_at | 0.01 | PREDICTED: *Canis familiaris* similar to myeloid-associated differen-marker (LOC611521); mRNA | 99.64664 | TTCAGTTCCTGTCTCATGGCCGCT CCCGGGACCATGCCATCGCCGCCA CTGCCTTCTCCTGCATCGCTTGTG TGGCTTATGCCACCGAAGTGGCCT GGACCCGGGCCCGTCCCGGAGAGA TCACCGGCTACATGGCCANTGTGC CGGGCCTGCTCAAGGTGCTGGAGA CCTTTGTGGCCTGCATCATCTTCG CCTTCATCAGCAACCCCTCCCTGT ACCAGCACCAGCCGGCCCTGGAGT GGTGTGTGGCCGTCTACTCCATCT GTTTCATCCTGGCGGCTGTGGCCA TCCTACTGAACCTGGGGGACTGCA CCAACATGCTGCCCATCTCCTTCC CCAGTTTCCTGTCGGGCCTGGCCC TGCTCTCCGTCCTGCTGTATGCCA CGGCTCTGGNTCTCTGGCCGCTCT ACCAGTTCAACGAGAAGTATGGTG GCAGCCCCGTCGGTCGAGGGATG TTAGCTGCGCCGACAGGCACACCT ACTACGTGTGTACCTGGGACCGCC GCCTGGCTGTGGCCATCCTGACAG CCATCAACCTGCTGGCTTACGTGG CTGACCTGGTGTAC |

TABLE 9-continued

Genes involved in muscle and bone regulation

| Sequence ID No. | Gene | Probe | P-value | Best current BLAST annotation | % match of probe sequence to BLAST hit | Probe Target Sequence |
|---|---|---|---|---|---|---|
| 30 | Protein Kinase C Binding Protein | Cfa.15485.1.A1_s_at | 0.01 | PREDICTED: Canis familiaris similar to protein kinase C binding protein 1 isoform b; transcript variant 11 (LOC477252); mRNA | 100 | GGAGCAGTCAGAACTAAGACATGG TCCGTTTTACTATATGAAGCAGCC ACTCACCACAGACCCTGTTGATGT TGTACCGCAGGATGGACGGAA |

TABLE 10

Summary of genes affecting glucocorticoid receptors and nitric oxide production

| Gene | Gene Expression Compared to Control | Role |
|---|---|---|
| Kinesin | ↓ | Transport of organelles from the (−) to (+) ends. Binds microtubules. ATPase activity |
| Capping Protein | ↓ | Part of dynactin-dynein hetero-complex |
| Calmodulin | ↓ | Directly influences calcium dependent dynein activity. Binds to nitric oxide synthase and up regulates the production of nitric oxide |
| Dynein | ↓ | Transport of organelles from the (+) to (−) ends. Binds microtubules. ATPase activity and force production |
| Dynactin | ↓ | Cytoplasmic dynein activator. Binds mirotubules and ↑average length of dyein movements. |
| Heat Shock Protein 1 beta (HSP90) | ↓ | Necessary for glucocorticoid receptor binding and fast transport of dynein complex to nucleus. Calcinuerin activity. Enhances the nitric oxide production by binding to nitric oxide synthase |
| PPIase | ↓ | Necessary for dynein/glucocorticoid interaction and movement |
| Calcinuerin | ↓ | Part of dynactin-dynein hetero-complex. Catalyzes the conversion of arginine to citrulline and nitric oxide |
| Protein kinase C | ↓ | Calcium-activated, phospholipid-dependent, serine- and threonine-specific enzyme. |
| Protein Kinase C Binding Protein | ↓ | Associated with protein kinase C |

Effect of Nutrition on Genes Involved with DNA Damage/Protection and Neural Function Eleven genes are identified that are related to DNA damage/protection and neural function. With regard to the latter, the genes identified are important for rebound potentiation; they are believed to have a potential role in motor learning. Interestingly, of these genes, all were down regulated except for of gamma-aminobutyric acid (GABA) A receptor, gamma 2 which was up regulated. The compositions disclosed herein may be part of a therapeutic regimen to treat animals suffering from diseases or disorders associated with or relating to DNA damage/protection and neural function. The identity of these genes and their putative role in DNA damage/protection and neural function are described in Tables 11 and 12 below.

TABLE 11

Genes involved in DNA damage/protection and neural function

| Sequence ID No. | Gene | Probe | P-value | Best current BLAST annotation | % match of probe sequence to BLAST hit | Probe Target Sequence |
|---|---|---|---|---|---|---|
| 31 | Gamma-aminobutyric acid (GABA) A receptor, gamma 2 | CfaAffx.26362.1.S1_at | <0.01 | Homo sapiens gamma-aminobutyric acid (GABA) A receptor; gamma 2 (GABRG2); transcript variant 1; mRNA | 100 | CCTCTTCTTCGGATGTTTTCCT TCAAGGCCCCTACCATTGAT |
| 22 | Calmodulin | Cfa.4168.1.S1_at | <0.01 | PREDICTED: Canis familiaris similar to calmodulin 1; transcript variant 3 (LOC480416); mRNA | 52.54237 | CCACCCATGGTGACGATGACAC ACATCCTGGTGGCATGCGTGTG TTGGTTTAGCGTTGTCTGCGTT GTACTAGAGCGAAAATGGGTGT CAGGCTTGTCACCATTCACACA GAAATTTAAAAAAAAAAAAAAA ANNNNGANAAAAAACCTTTACC AAGGGAGCATCTTTGGACTCTC TGTTTTTAAAACCTCCTGAACC ATGACTTGGAGCCAGCAGATTA GGCTGTGGCTGTGGACTTCAGC ACAACCATCAACATTGCTGATC AAGAAATTACAATATACGTCCA TTCCAAGTT |
| 28 | Calcineurin | Cfa.19761.1.S1_at | <0.001 | PREDICTED: Canis familiaris similar to protein phosphatase 3 (formerly 2B); catalytic subunit; beta isoform (calcineurin A beta); transcript variant 5 (LOC479248); mRNA | 98.83382 | GAATTAACAATCTGCTTGAGCC CCAAAACACTACTTATGCACTT CACTTGCCAAAAGATTTGNGCA AGGTTTTGTACCCTGGTAAATG ATGCCAAAGTTTGTTTTCTGTG GTGTTTGTCAAATGTTCTATGT ATAATTGACTGTCTGTAACATG CTGTTTNCTTCCTCTGCAGATG TAGCTGCTTTCCTAAATCTGTC TGTCTTTCTTTAGGTTAGCTGT ATGTCTGTAAAAGTATGTTAAA TTAAATTACTCTATCAGACGCT TGTCTGTCTTTTGATGTAGAAG CAACTTTGTAGCACCTTGTTTT GAGGTNNGCTGCATTTGTTGCT GTACTTTGTGCAT |
| 32 | Calcium/ calmodulin-dependent protein kinase II | Cfa.3884.1.S1_at | <0.01 | Homo sapiens PTEn induced putative kinase 1 (PINK1); mRNA | 24.10714 | GGTGCTGTTCACCACAGTAAGT GGCCTCTCAGTGTTGCTGACCA AAGTGTGAAATCCTAGAGCTTC AGGGGAGAGGACGTGGGGGAAA TCCGGGGCTTGACTTTATAATA GGATTATAGAGATGAAAAGTAC ACCTTGCTTTAGGCAACAGTTG GGATTCCTAAGCGCATGTGTA AGAGCATATGTGAAATCCCTTC CCCATTGTTGATCTCTACTCAC AGAATTTGTCTTTATTATGGT GTAAGAATCACTCTTAAAGCCA CATATTCAATTCAAAGCAAATA CGTGTTCTGCAGTTGCAAATGT GTATTTAATTCTTCACAATTCC TGTAAG |
| 33 | Adenylate cyclase-associated protein 1 | CfaAffx.5462.1.S1_s_at | <0.01 | PREDICTED: Canis familiaris similar to Adenylyl cyclase-associated protein 1 (CAP 1); transcript variant 1 (LOC475317); mRNA | 100 | GAAACTCGGTCTGGTGTTCGAT GACGTCGTGGGCATTGTGGAGA TAATCAATAGTAGGGATGTCAA AGTTCAGGTAATGGGTAAAGTG CCAACCATTTCCATCAACAAAA CAGATGGCTGCCATGTTTACCT GAGCAAGAATTCCCTGGATTGC GAAATAGTCAGTGCCAAATCTT CTGAGATGAATGTCCTCATTCC TACTGAAGGCGGTGACTATAAT GAATTCCCAGTCCCTGAGCAGT TCAAGACCCTATGGAATGGGCA GAAGTTGGTCACCACAGTGACA GAAATTGCTGGATAAGCGAAGT GCCACTGGGTTCTTTGCCCTCC |

TABLE 11-continued

Genes involved in DNA damage/protection and neural function

| Sequence ID No. | Gene | Probe | P-value | Best current BLAST annotation | % match of probe sequence to BLAST hit | Probe Target Sequence |
|---|---|---|---|---|---|---|
| | | | | | | CCCTCACACCATGGGATAAATC TATCAGGACGGTTCTTTTCTAG ATTTCCTTTACCTTTCTGCTCT TAAACTGCTT |
| 34 | Protein Phosphatase I | Cfa.6174.1.A1_at | <0.01 | PREDICTED: Canis familiaris similar to protein phosphatase 1A isoform 1; transcript variant 2 (LOC480344); mRNA | 100 | AAATCTTACGAAGCCCAATATG CAGGGAGTTAACTGAAAACTAT CTTGGCAGTGAGGTTGGCACTG TTGATAAAGCTGGTCCCTTCCT TTAACTGTCTTTTAGGTTGTTC TTGCCTTGTTGCCAGGAGTATT GCAGGTAATACAGTATATTCAT AAGAATATCAATCTTGGGGCTA AAATGCCTTGATTCTTTGCACC TCTTTTACAAGTCCTTACGTTG AATTACTAATTGATAAGCAGCA GCTTCCTACATATAGTAGGAGA CTGCCACGTTTTTGCTATCATG ATTGGCTGGGCCTGCTGCTGTT CCTAGTAAGGTAT |
| 35 | Diazepam binding inhibitor | CfaAffx.14836.1.S1_s_at | <0.01 | PREDICTED: Canis familiaris similar to peroxisomal D3; D2-enoyl-CoA isomerase isoform 1 (LOC478706); mRNA | 100 | AATGGTGCCATCTTACTGAGGG ATTTTGTAGGCTGTTTTATAGA TTTTCCTAAGCCTCTGGTTGCA GTGATAAATGGTCCAGCCATAG GAATCTCCGTCACCATTCTCGG GCTATTCGATCTTGTGTATGCT TCCGACAGGGCAACATTTCACA CTCCTTTTACTCACCTGGGCCA AAGTCCAGAAGGATGTTCCTCC TATACTTTTCCCAAGATAATGG GCCAAGCCAAGGCAGCAGAGAT GCTCATGTTTGGAAAGAAGTTA ACAGCTAGAGAAGCCTGTGCTC AAGGACTTGTTACTGAAGTTTT TCCCGATAGCACTTGTCAGAAA GAAGTTTGGACCAGGCGGAAAG CATATTCAAAACTCCCCCGAAA TACCTTGCATATTTCCAAACAG AGCATCAGAAATCTTGAGAAAG AAAAGCTACATGCTGTTAACGC AGAAGAAAACAGCGTCCTCCAG GAAAGGTGGCTGTCAGACGAAT GCATAAATGCAGTCATGAGCTT CTTATCCCGGAAGGCCAA |
| 36 | Tumor protein p53 binding protein | Cfa.1611.1.A1_s_at | <0.01 | PREDICTED: Canis familiaris similar to tumor protein p53 binding protein; 1; transcript variant 4 (LOC478274); mRNA | 97.90874 | ATGATAGTTGCCATGCCAACCA GCTCCAGAATTACCGCAATTAT TTGTTGCCTGCAGGGTACAGCC TTGAGGAGCAAAGAATTCTGGA TTGGCAACCCCGTGAAAACCCT TTCCACAATCTGAAGGTACTCT TGGTGTCAGACCAACAGCAGAA CTTCCTGGAGCTCTGGTCTGAG ATCCTCATGACCGGGGGGGCAG CCTCTGTGAAGCAGCACCATTC AAGTGCCCATAACAAAGATATT GCTTTAGGGGTATTTGACGTGG TGGTGACGGATCCCTCATGCCC AGCCTCGGTGCTGAAGTGTGCT GAAGCATTGCAGCTGCCTGTGG TGTCACAAGAGTGGGTGATCCA GTGCCTCATTGTTGGGGAGAGA ATTGGATTCAAGCAGCATCCAA AATACAAACATGATTATGTTTC TCACTAATACTTGGTCTTAACT GATTTTATTCCCTGCTGTTGTG GAGATTGTGNTTNNNCCAGGTT TTAAATGTGTCTTGTGTGTAAC TGGATTCCTTGCATGGATCT |
| 4 | Ubiquitin conjugating | CfaAffx.275.1.S1_s_at | <0.001 | PREDICTED: Pan troglodytes | 97.19626 | GATTTGGCCCGTGACCCTCCAG CACAATGTTCTGCAGGTCCTGT |

TABLE 11-continued

Genes involved in DNA damage/protection and neural function

| Sequence ID No. | Gene | Probe | P-value | Best current BLAST annotation | % match of probe sequence to BLAST hit | Probe Target Sequence |
|---|---|---|---|---|---|---|
| | enzyme E2D 3 | | | LOC461941 (LOC461941); mRNA | | TTGGGATGATATGTTTCATTGG CAAGCCACAATTATAGGACCTA ATGACAGCCCATATCAAGG |
| 5 | NEDD8 ultimate buster-1 | Cfa.12556.1.A1_s_at | <0.001 | PREDICTED: *Canis familiaris* similar to NEDD8 ultimate buster-1 (NY-REN-18 antigen) (LOC475542); mRNA | 99.12473 | GGAATGGGCTACTCTACTCATG CAGNCAAGCAGGNCCTGCATCA GGCCAGTGGGAACCTGGACGAA GCCCTGAAGATTCTTCTCAGCA ATCCTCAGATGTGGTGGTTAAA TGATTCAGATCCTGAAACGANC AACCAGCAAGAAAGTCCTTCCC AGGAAAACATTGACCAACTGGT GTACATGGGCTTCGACGCTGTG GTGGCTGATGCTGCCTTGAGAG TGTTCAGGGGAAACGTGCAGCT GGCAGCTCAGNCCCTCGCCCAC AACGGAGGAACTCTTCCTCCTG ACCTTCAGCTCTTGGTGGAAGA CTCTTCATCAACGCCATCCACG TCCCCTTCCGACTCCGCAGGTA CCTCTAGTGCCTCAACAGATGA AGATATGGAAACCGAAGCTGTC AATGAAATACTGGAAGATATTC CAGAACATGAAGAAGATTATCT TGACTCAACACTGGAAG |
| 37 | BCL2-associated X protein (BAX) | CfaAffx.6742.1.S1_s_at | <0.01 | *Canis familiaris* BCL2-associated X protein (BAX); mRNA | 100 | GGCCCACCAGCTCTGAGCAGAT CATGAAGACAGGGGCCCTTTTG CTTCAGGGTTTCATCCAAGATC GAGCAGGGCGAATGGGGGGAGA GACACCTGAGCTGCCCTTGGAG CAGGTGCCCCAGGATGCATCCA CCAAGAAGCTGAGCGAATGTCT CAAGCGCATCGGAGATGAACTG GACAGTAACATGGAGTTGCAGA GGATGATCGCAGCTGTGGACAC AGACTCTCCCCGTGAGGTCTTC TTCCGAGTGGCAGCTGAGATGT TTTCTGATGGCAACTTCAACTG GGGCCGGGTTGTTGCCCTCTTC TACTTTGCCAGCAAACTGGTGC TCA |

TABLE 12

Summary of genes important for rebound potentiation and DNA integrity

| Gene | Gene Expression Compared to Control | Role |
|---|---|---|
| Gamma-aminobutyric acid (GABA) A receptor, gamma 2 | ↑ | Involved in single channel conductance (Cl-channel) |
| Calmodulin | ↓ | Influx of calcium results in calcium/calmodulin complex which activates CaMKII and calcineurin |
| Calcineurin | ↓ | Involved in the pathway for RP suppression |
| Calcium/calmodulin-dependent protein kinase II | ↓ | Involved in induction and suppression of RP |
| Adenylate cyclase-associated protein 1 | ↓ | Adenylyl cyclase is involved in suppression of RP |
| Protein Phosphatase I | ↓ | Dephosphorylates components in stress-activated pathways. Active PP-1 results in CaMKII inhibition and RP suppression |
| Diazepam binding inhibitor | ↓ | Displaces benzodiazepine Down regulates the effects of GABA |
| Tumor protein p53 binding protein | ↓ | Keep the cell from progressing through the cell cycle if there is damage to DNA present. |
| Ubiquitin conjugating enzyme E2D 3 (and NEDD8 ultimate buster-1) | ↓ | The regulated proteolysis of proteins by proteasomes removes denatured, damaged or improperly translated proteins from cells and regulates the level of proteins like cyclins or some transcription factors |

TABLE 12-continued

Summary of genes important for rebound potentiation and DNA integrity

| Gene | Gene Expression Compared to Control | Role |
|---|---|---|
| BCL2-associated X protein | ↓ | Accelerates programmed cell death by binding to, and antagonizing the apoptosis repressor BCL2 |

Effect of Nutrition on Genes Involved with Glucose Metabolism

Twenty four genes associated with glucose metabolism are down regulated in animals fed the super senior diet which would suggest that these animals are utilizing fat (fat oxidation) instead of glucose as a fuel source. The compositions disclosed herein may be part of a therapeutic regime in diabetic animals and/or for obesity prevention or treatment in an animal. These down regulated genes are identified and their putative role in glucose metabolism described in detail below in Tables 13 and 14.

TABLE 13

Genes involved in Glucose Metabolism

| Sequence ID No. | Gene | Probe | P-value | Best current BLAST annotation | % match of probe sequence to BLAST hit | Probe Target Seq. |
|---|---|---|---|---|---|---|
| 38 | Phosphorylase kinase | Cfa.10856.1.S1_at | <0.01 | PREDICTED: Canis familiaris similar to phosphorylase kinase beta; transcript variant 2 (LOC478139); mRNA | 99.3392 | GAAAGTTCACCACTGCATGTTT TATGATCAGATAACTCATTGAA ATGAGTCTTTGCTCTTTAGACT AAATTCCCACCTAGTACTGCCA TTAAAATGAATTTGCCAGCTGG TGTGCATACTGGAAATGAAAAG ATACTGAAAGAATGGAACGAAT GGTGAGCTTAACTCAGTGGCAC TGTCATACTGGAAAAATACAGT AAAATCATAAAAACAGATCTGC CAGCTGATGTTTTTATTCTCAG AAACAGCATTGTTGATAATATT TTAGTATACAGAGCTACTGTAC AATTTTTACCTTGNAAACATGA CTGTGGTTTTGTATTTGTGTTG ACTTTAGGGGTTGGGATAAAAT NCAGTATAATATATACCTTATC AAACNTTTTCTTTGAGCTCTTA CTAAAAATATGGCATGCATAAG ATTGTTCAGAAGAGTAGACTGT TAACCTAGTTTGTA |
| 39 | Phosphorylase | Cfa.10412.1.A1_s_at | <0.01 | PREDICTED: Canis familiaris phosphorylase; glycogen; liver; transcript variant 1 (PYGL); mRNA | 99.36306 | CTTCCAGAGCTGAAGCTGGCCA TTGATCNAAATTGACAATGGCT TCTTCTCTCCCAAGCAGCCTGN CCTCTTCAAAGATTTAATCAAT ATGCTATTTTATCATGACAGGT TTAAAGTCTTCGCAGACTATGA AGCCTATGTCAAGTGTCAAGAA AAAGTCAGCCAGCTGTACATGA ATCCAAAGGCCTGGAACACAAT GGTACTCAAAAACATAGCTGCC GCAGGGAAGTTCTCTAGTGACC GAACAATTAAGGAATATGCCAG GGACATCTGGAACATGGAACCT TCAGATCTCAAGATTTCCCTAT CCAATG |
| 40 | Glycogen synthase kinase 3 | Cfa.913.1.A1_s_at | <0.01 | PREDICTED: Canis familiaris similar to Glycogen synthase kinase-3 beta (GSK-3 beta); transcript variant 1 (LOC478575); mRNA | 99.49622 | GACTCCACCGGAGGCAATTGCA CTGTGTAGCCGTCTGCTGGAGT ATACACCAACTGCCCGATTGAC ACCACTGGAAGCTTGTGCACAT TCATTTTTTGATGAATTAAGGG ACCCAAATGTCAAACTACCAAA TGGGCGAGACACACCTGCACTC TTCAACTTCACCACTCAAGAAC TGTCAAGTAATCCACCTCTAGC TACCATCCTTATTCCTCCTCAT GCTCGGATTCAAGCAGCTGCTT CAACCCCTACAAATGCCACAGC AGCCTCAGATGCTAATGCCGGA GACCGTGGACAGACGAACAATG CCNCTTCTGCATCAGCTTCTAA CTCCACCTGAACAGTCCCGAGC AGCCAGCTGCACAGGAAGAACC |

TABLE 13-continued

Genes involved in Glucose Metabolism

| Sequence ID No. | Gene | Probe | P-value | Best current BLAST annotation | % match of probe sequence to BLAST hit | Probe Target Seq. |
|---|---|---|---|---|---|---|
| | | | | | | ACCAGTTACTTGAGTGTCACTCA |
| 22 | Calmodulin | Cfa.4168.1.S1_at | <0.01 | PREDICTED: *Canis familiaris* similar to calmodulin 1; transcript variant 3 (LOC480416); mRNA | 52.54237 | CCACCCATGGTGACGATGACACACATCCTGGTGGCATGCGTGTGTTGGTTTAGCGTTGTCTGCGTTGTACTAGAGCGAAAATGGGTGTCAGGCTTGTCACCATTCACACAGAAATTTAAAAAAAAAAAAAAAANNNNGANAAAAAACCTTTACCAAGGGAGCATCTTTGGACTCTCTGTTTTTAAAACCTCCTGAACCATGACTTGGAGCCAGCAGATTAGGCTGTGGCTGTGGACTTCAGCACAACCATCAACATTGCTGATCAAGAAATTACAATATACGTCCATTCCAAGTT |
| 29 | Protein Kinase C | CfaAffx.408.1.S1_s_at | <0.01 | PREDICTED: *Canis familiaris* similar to myeloid-associated differentiation marker (LOC611521); mRNA | 99.64664 | TTCAGTTCCTGTCTCATGGCCGCTCCCGGGACCATGCCATCGCCGCCACTGCCTTCTCCTGCATCGCTTGTGTGGCTTATGCCACCGAAGTGGCCTGGACCCGGGCCCGTCCCGGAGAGATCACCGGCTACATGGCCANTGTGCCGGGCCTGCTCAAGGTGCTGGAGACCTTTGTGGCCTGCATCATCTTCGCCTTCATCAGCAACCCCTCCCTGTACCAGCACCAGCCGGCCCTGGAGTGGTGTGTGGCCGTCTACTCCATCTGTTTCATCCTGGCGGCTGTGGCCATCCTACTGAACCTGGGGGACTGCACCAACATGCTGCCCATCTCCTTCCCCAGTTTCCTGTCGGGCCTGGCCCTGCTCTCCGTCCTGCTGTATGCCACGGCTCTGGNTCTCTGGCCGCTCTACCAGTTCAACGAGAAGTATGGTGGCCAGCCCCGTCGGTCGAGGGATGTTAGCTGCGCCGACAGGCACACCTACTACGTGTGTACCTGGGACCGCCGCTGGCTGTGGCCATCCTGACAGCCATCAACCTGCTGGCTTACGTGGCTGACCTGGTGTAC |
| 30 | Protein Kinase C Binding Protein | Cfa.15485.1.A1_s_at | <0.01 | PREDICTED: *Canis familiaris* similar to protein kinase C binding protein 1 isoform b; transcript variant 11 (LOC477252); mRNA | 100 | GGAGCAGTCAGAACTAAGACATGGTCCGTTTTACTATATGAAGCAGCCACTCACCACAGACCCTGTTGATGTTGTACCGCAGGATGGACGGAA |
| 41 | Hexokinase 3 | Cfa.19125.2.S1_at | <0.01 | *Macaca fascicularis* testis cDNA; clone; QtsA-14856; similar to human receptor associated protein 80 (RAP80); mRNA; RefSeq: NM_016290.3 | 76.70683 | TAATGACTGCCAACTCACTGTTTGTTGGAGTTATATGCAGAAATAAAGNCCAAGTCTTCAGAAACAGGCTTCAGGATGCCCTCACCAGGGATGGAAGAGGCAGGCTGCAGCAAAGAGATGCAGAGTTCCCTTGCACATCTCGACTTAAATGAGTCTCCCATCAAGTCTTTTGTTTCCATTTCAGAAGCCACAGATTGCTTAGTGGACTTTAAAAAGCAACTTAACGTTCGGCAAGGTAGTCGGACACGGACCAAAGCAGGCAGAGGAAGAAGGAGAAAACCCTGAATTTCTAGGGTCCAGACACCCGACAAAACCATTAGCAATAGGGGTGGGCCGTGTCATTAAGTCTTAGTGGCTTCTGTTTCATTGTTGAA |

TABLE 13-continued

Genes involved in Glucose Metabolism

| Sequence ID No. | Gene | Probe | P-value | Best current BLAST annotation | % match of probe sequence to BLAST hit | Probe Target Seq. |
|---|---|---|---|---|---|---|
| | | | | | | CAAGTTTTTTGGCCCNGCAGTT TTCACCACCAGCACCAACTCAG CATTCTTGTTTTGATGTTTTCT ATAAGCTATACAGACAATTGTG TATAGTATTCTGTTTTATAACA GTCTGGATTCACTT |
| 42 | Fructose 1,6 bisphos-phatase | CfaAffx.26135.1.S1_s_at | <0.01 | PREDICTED: *Canis familiaris* aldolase A; transcript variant 1 (LOC479787); mRNA | 100 | AGTGGCGCTGTGTGCTGAAAAT TGGGGAACACACTCCCTCAGCC CTTGCGATCATGGAAAATGCCA ACGTTCTGGCCCGTTAT |
| 43 | Glyceral-dehyde 3-phosphate dehydrogenase | AFFX-Cf_Gapdh_3_at | <0.01 | *Canis familiaris* glyceraldehyde-3-phosphate dehydrogenase (GAPDH); mRNA | 100 | AGCTCACTGGCATGGCCTTCCG TGTCCCCACCCCCAATGTATCA GTTGTGGATCTGACCTGCCGCC TGGAGAAAGCTGCCAAATATGA CGACATCAAGAAGGTAGTGAAG CAGGCATCGGAGGGACCCCTCA AAGGCATCCTGGGCTACACTGA GGACCAGGTGGTCTCCTGTGAC TTCAACAGTGACACCCACTCTT CCACCTTCGACGCCGGGGCTGG CATTGCCCTCAATGACCACTTT GTCAAGCTCATTTCCTGGTATG ACAATGAATTTGGCTACAGCAA CCGGGTGGTGGACCTCATGGTC TACATGG |
| 44 | Glucose 6-phosphate dehydrogenase | Cfa.19351.1.S1_at | <0.01 | *Homo sapiens* cDNA FLJ30869 fis; clone FEBRA2004224 | 15.11194 | GAATGTGTTGGCAGACTGAGGC CCCCCATGTTTTTAATGCGCAC TGGGGACAACCATCTAAGGTCT AGAAACTTTTGGACCATAGGAA AGATAGGTTTATGGTCCTCTTC CAGATGCAGCCCTAGGAGAGCA TTCCCATGGGGTCTCTGGATCC CTTTCNTTGCTCTGTGAGGCTC TGTGACCACCTTTTGNNNTGNN GGGGGCAGGGGGNCTTCCTCAG CTCCGCCTCCAGTGCCCCCAGG TCCCCCACGGCTCACAGTCCNT GAAAATTCAGAGCTGCCCTGTA AGGATTTTGTCCACTGGGCAAT TCAGATATACTTCGATATCCCT GAGAAAGAAGAGGCAGCAGCAA ACACTCCCNAGGGCATCTGTCT CAGNNATCTCTCNTTGNATGAG ACAGAAGCCTACTTTTCAGAAA NCTTATCANGGNTACTTTATAA GAAACTTTTTTTTTTTNCTAA AATCAGACAAAAGGTGGCTTNT GCATATTCTTNATTAATAACTG TGTCTTTGTCCTCTGCTTAA CTTTAGGA |
| 45 | Enolase | CfaAffx.30133.1.S1_s_at | <0.01 | PREDICTED: *Canis familiaris* similar to T21B10.2b; transcript variant 1 (LOC479597); mRNA | 97.72257 | GGTACATCACGCCTGATCAGCT GGCTGACCTCTACAAGTCCTTC ATCAGGGACTACCCAGTGGTGT CTATCGAAGACCCCTTCGACCA GGATGACTGGGAAGCTTGGCAG AAATTCACTGCCAGCGCTGGAA TCCAGGTGGNGGGGGANGATCT CACCGTGACCAACCCAAAGCGG ATTTCCAAGGCTGTGGGCGAGA AATNGTGCAACTGCCTCCTGCT TAAAGTGAACCAGATTGGCTCT GTGACCGAGTCTCTTCAGGCGT GCAAGCTGGCCCAGTCCAATGG GTGGGGCGTCATGGTGTCGCAT CGCTCCGGGGAGACCGAAGATA CCTTCATCGCTGACCTGGTGGT |

TABLE 13-continued

Genes involved in Glucose Metabolism

| Sequence ID No. | Gene | Probe | P-value | Best current BLAST annotation | % match of probe sequence to BLAST hit | Probe Target Seq. |
|---|---|---|---|---|---|---|
| | | | | | | GGGANTCTGCACTGGGCAGATC AAGACGGGTGCACCATGCAGAT CTGAGCGCTTGGCCAAGTACAA CCAGATCCTCAGAATTGAAGAG GAACTGGGTAGCAAGGCCAAGT TCGCCGGCAGAAGCTTCAGAA |
| 46 | Lactate dehydrogenase | Cfa.300.1.S1_at | <0.01 | PREDICTED: *Canis familiaris* similar to L-lactate dehydrogenase A chain (LDH-A) (LDH muscle subunit) (LDH-M) (Proliferation-inducing gene 19 protein); transcript variant 1 (LOC476882); mRNA | 97.99427 | ATCTGACCTGTTACTCAAGTCG TAATATTAAAATGGCCTAAGAA AAAAACATCAGTTTCCTAAAGT TACACATAGGAATGGTTCACAA AACCCTGCAGCTATGTCCTGAT GCTGGATGAGACCTGTCTTGTG TAGTCCTAAATTGGTTAACGTA ATATCGGAGGCACCACTGCCAA TGTCATATATGCTGCAGCTACT CCTTAAACCAGATGTGTATTTA CTGTGTTTTGTAACTTCTGATT CCTTCATCCCAACATCCAACAT GCCTAGGCCATCTTTTCTTCTT CAGTCACATCCTGGGATCCAAT GTATAAATTCAATATTGCATGT ATTGTGCATAACTCTTCTA |
| 47 | Citrate lyase | Cfa.10361.2.S1_at | <0.01 | PREDICTED: *Canis familiaris* similar to citrate lyase beta like (LOC476974); mRNA | 98.49624 | AGTATGCCAGATCGGAACCTTT TTCCCATTTACAGTTCATGTTA ATCCAATTTTTTTATTATCTC ACTGGCCAGTTATTCCTTTAAA AATGAACTTCCTTCTTTTTGAT TCCAAGCTTATGATTTTACTGC TCATTAATGTGTTACAAATATG CACTTAATGATTTCACAGGGAG ATAAAATAGTGAAGAGAGATGG GCTGAGGGGCTGTTAGGACTTT AATGAAACAGATCTTTCCCGAA TATTTCTCCCTTCACATTTCTC ACATTAGATGTTTCCACATTG TTCTACTCCACACTATAAATAA TTTTAAGGCCAATCTTAAAAAA TGGTAGTTAAGTGAAGGGGTTG TGTTTATTTCACTAGAAATCTG ATAAAACGAGAGATGACATAGA AAAAGTTATCATTTTTGTTCAT ACAGATGGCTTCTAAAAATAAA TCTTCAAAACTGATTACTTTTA ACCTCCACCTCCCAAAATGAAA CATCCCTACATTTGAACTGCTA GGTGAGAACTCTGAAAGCCCTC ATCC |
| 48 | Glycerol kinase | CfaAffx.21204.1 S1_s_at | <0.01 | PREDICTED: *Canis familiaris* similar to glycerol kinase isoform 2; transcript variant 8 (LOC480872); mRNA | 100 | GGGTACATCCTATGGCTGCTAT TTCGTCCCCGCGTTTTCAGGGT TATATGCACCTTACTGGGAGCC CAGTGCAAGAGGGATCATCTGT GGGCTCACTCAATTCACCAATA AATGCCATATTGCTTTTGCTGC ATTAGAAGCTGTTTGTTTCCAA ACCCGGGAGATTTTGGATGCCA TGAACCGAGACTGCGGAATTCC ACTCAGTCATTTGCAGGTAGAT GGAGGAATGACCAACAACAAAA TTCTTATGCAACTACAAGCAGA CATTCTATATATCCCAGTAGTG AAGCCCTCGATGCCAGAAACAA CTGCCCTGGGAGCTGCCATGGC AGCCGGGCTGCGGAGGGAGTT GGTGTTTGGAGTCTTGAACCCG AGGATCTGTCAGCAGTCACGAT GGAGCGATTTGAACCCCAGATC AATGCTGAGGAAAGTGAAATTC GTTACTCTACATGGAAGAAGGC TGTGATGAAGTCAGTGGGCTGG GTTACAACTCA |

TABLE 13-continued

Genes involved in Glucose Metabolism

| Sequence ID No. | Gene | Probe | P-value | Best current BLAST annotation | % match of probe sequence to BLAST hit | Probe Target Seq. |
|---|---|---|---|---|---|---|
| 49 | Transketolase | CfaAffx.13684.1.S1_s_at | <0.01 | Homo sapiens transketolase (Wernicke-Korsakoff syndrome); mRNA (cDNa clone MGC: 15349 IMAGE: 4310396); complete cds | 86.53846 | GAAGATCTGGCCATGTTTCGGT CCATCCCCACTGCTACGATCTT TTACCCAAGTGACGGGGTGTCA ACAGAGAAGGCGGTGGAATTAG CAGCCAATACAAAGGGCATCTG CTTCATCCGGACCAGCCGCCCA GAAAACGCCATCATCTATAACA ACAATGAGGATTTCCAAATCAA ACAAGCCAAGGTGGTCCTGAAG AGCAAGGATGACCAGGTGACTG TGATTGGGGCCGGAGTGACCCT ACATGAGGCCTTGGCTGCTGCT GAACTGCTGAAGAAAGAGAAGA TCAACATTCGTGTGTTGGACCC CTTCACCATCAAGCCCCTGGAC AGAAATCTCATTCTCGAAAGCG CCCGTGCGACCAAGGGCAGGAT CGTCACCGTGGAGGACCATTAC TATGAAGGTGGCATAGGTGAGG CAGTGTCCTCTGCCTTGGTGGG TGAGCCTGGCATCACCGTCTCC CGCCTTGCAGTTGGTGAGGTAC CAAGAAGCGGGAAGCCAGCTGA GCTGCTGAAGATGTTTGGCATT GACAGGGACGCCATCGCACAAG CTGTGAGGGACCTTGTCGCCAA |
| 50 | Ribulose phosphate 3-epimerase | Cfa.13084.1.A1_s_at | <0.01 | Homo sapiens SLIT-ROBO Rho GTPase activating protein 2 (SRGAP2); mRNA | 57.79468 | CCCCAAGGAGATGAGGAGCGAT GACCCCAGCAACAGGAANAACA GCCCACTGAAGGGCTGGTGTGT GTGTNCTTCACGTGCCAGAAGA GAAGTTTAGATCCTCCCAGGGG AATCGCAATGTTGTGGCGTCCT GACTTGTATGTCACGTTTTGTG TAAAAATGGTATATTCTTTAAA ATAGTGTTGATAACTGGAATAT TGTATGTATGCTTGGAGATGCT TTGTGTGAACCTAAGACTGTCA CTCAACAGATGTTGGATTGGG |
| 51 | Ribose 5-phosphate isomerase | Cfa.335.2.S1_at | <0.01 | PREDICTED: Canis familiaris similar to ribose 5-phosphate isomerase A (ribose 5-phosphate epimerase) (LOC475755); partial mRNA | 100 | AGCCTTTCTACTGACCCTGCAA GAGTGGAGCGTGTTCACCTTGA ACCCCAGCGTGCAGCTGAGGT AGACATGCCTCTCCAGGAGCCT TTGCCTTAATGCATCTGTGCCA GACAGACGGCTGG |
| 52 | Cytochrome c oxidase polypeptide VIIa-liver/heart, mitochondrial precursor | CfaAffx.4942.1.S1_s_at | <0.01 | PREDICTED: Canis familiaris similar to cytochrome c oxidase; subunit 7a 3 (LOC611134); mRNA | 100 | GGCAGTTTGAAAATAAAGTTCC AGAGAAACAAAAGCTATTTCAG GAGGATAATGGAATTCCAGTGC ATCTAAAGGGTGGAGTAGCTGA TGCCCTCCTGTATAGAGCCACT ATGATGCTTACAGTTGGTGGAA CAGCATATGCCATGTATCAGCT AGCTGTGGCTTCTTTTCCCAAG AAGCA |
| 53 | Cytochrome c oxidase subunit VIII liver form | Cfa.15065.1.S1_at | <0.01 | PREDICTED: Canis familiaris similar to Cytochrome c oxidase polypeptide VIII-liver; mitochondrial precursor (Cytochrome c oxidase subunit 8-2) (LOC476040); | 99.75961 | GGTCCGCAGTCGTTCTGTGCGG TCATGTCTGTGCTGGTGCCGCA GCTGCTGAGGGGCCTAACAGGC CTCACCCGGCGGCTCCCGGTGC ATCGTGCCCAGATCCATTCCAA GCCGCGGGAGCAGCTCGGG ACCATGGATGTTGCCGTTGGGC TCACCTNCTGCTTCCTGTGTTT CCTCCTGCCATCGGGCTGGGTC CTGTCACACCTGGAGAGCTACA AGAAGCGGGAGTGAAGGGGGCT |

TABLE 13-continued

Genes involved in Glucose Metabolism

| Sequence ID No. | Gene | Probe | P-value | Best current BLAST annotation | % match of probe sequence to BLAST hit | Probe Target Seq. |
|---|---|---|---|---|---|---|
| | | | | mRNA | | GTCCTGTCCCTCACCCTGTGAC CTGACCACCCCTGGCCTGTCCT GATCATGTCTGCTGCATTCCTG GCCGGCCTTCCATGGATCATGT CCTTCAATTACAGTGACCTCTT CTACAGTCATGACCTCTTGATT TCTCCATGGTGACATCCTGGGA CCAAACATATTGGTTTATAA |
| 54 | Ubiquinol-ucytochrome c reductase | Cfa.1425.2.A1_at | <0.01 | PREDICTED: Canis familiaris similar to Ubiquinol-cytochrom-c reductase complex core protein 2; mitochondrial precursor (Complex III subunit II); transcript variant 1 (LOC479815); mRNA | 27.18053 | CTTATGCATTCCTTCCAAAATT GGATCATTTAGGTCAAATTATT TGATGTTAAATCATAAGTTTTC ATTTGCTTACATTTACGATATC AGCGTCAGCTACGGAATCAATC TGCTGAAGGACCGTGGCTGGCG GCGTGTACGATCCAGCAACCAG CGCCTGGGACCCGACTTCATCC AGGAACCCCTCAGAAGACTCCA CTGACATTAGGAAGACTCATAA GAACCTTACAAGAAAAAGTATC AACCCCATCAAAACGGCAGAAA AGAAACATATCTTGTTATTAGT AGCTGAAATTCCATTTTCTACA TGTTGCCATACCTTATAAAAAC TACACTAAGCTACGCTTAAGGA AATACATTTTCTTAAATAAATT AGAATTGAAACCAATTTTTAAG TAAATCTAGGGNTTCAATTTAT TCTCATTGNGTNTTGTTTCTGG TGCAATCATGAANAACAGCATN CTATTAACCAACCTTGGTCCCA TGTACATAA |
| 55 | ATP synthase | CfaAffx.3186.1.S1_s_at | <0.01 | PREDICTED: Canis familiaris similar to ATP synthase; H + transporting; mitochondrial FO complex; subunit c isoform 2a precursor (LOC477595); mRNA | 98.57651 | AATTGGGACTGTGTTTGGGAGC CTCATCATTGGTTATNCCAGGA ATCCCTCTCTGAAGCAACAGCT CTTCTCCTACGCCATTCTGGGC TTTGCCCTCNCGGAGGCCATGG GGCTTTTTTGCCTGATNGTGGC CTTTCTCATCCTCTTNGCCATG TGAAGGAGTCGTCTCCACCTCC CATAGGTCTTTCTCCCATGTCT TGTCTGCCCTGTATGCCCTGTA TGTTCCTTTTCCTATACCTCCC CAGGCAGCCTGGGGAAAGTGGT TGGCTCAGGGTTTGACA |
| 56 | NADH-ubiquinone oxidoreductase | Cfa.4415.1.S1_at | <0.01 | PREDICTED: Canis familiaris similar to NADH-ubiquinone oxidoreductase MLRQ subunit (Complex I-MLRQ) (CI-MLRQ) (LOC477682); mRNA | 98.20789 | GGTGACTTTGGACGTCCGTTCC TGCTCTGTGGAGGCNNTGCTTC GTTCCGGGCCTTGCGGCAACTC GGTNTTTCCTTCCCCTGCGCGG GAGACCTCTGCCACAACCATGT TACGCCAGATCATCGGTCAGGC CAAGAAGCATCCGAGCTTGATC CCCCTCTTCATATTTATTGGGG CAGGAGGTACTGGAGCAGCGCT GTATGTATTGCGCTTGGCATTG TTCAATCCAGATGTTAGTTGGG ATAGGAAGAATAACCCAGAACC TTGGAACAAACTGGGTCCCAAT GATCAATACAAGTTCTACTCAG TGAATGTAGATTACAGCAAACT GAAGAAGAAGGTCCAGACTTC TAAATGAAATGTTTCACTATAA AGCTGCTTAGAATGAAGGTCTT CCAGAAGCCATCCGCACAATTT TCCACTTATCCAGGAAATATTT CCCCTCTAAATGCACGAAATCA TGTTGGTGTATTGTGTTGGGGT TTACACTNNANNANTAAATATC TGAAACTTGANANGTGTCACTA TTTAATGCTGAAAATTTGCTCT GAACTTTA |

TABLE 13-continued

Genes involved in Glucose Metabolism

| Sequence ID No. | Gene | Probe | P-value | Best current BLAST annotation | % match of probe sequence to BLAST hit | Probe Target Seq. |
|---|---|---|---|---|---|---|
| 57 | Facilitated glucose transporter/ Glucose transporter-like protein III (GLUT3) | Cfa.1370.1.A1_at | <0.01 | Homo sapiens cDNA FLJ44038 fis; clone TESTI4028880; highly similar to Glucose transporter type 3; brain | 23.95833 | TTGGAAGGATGGATGCTTGCCC CAGGTCATGGACACCTCCACAA ATCATCTAGTTTCCCAGTATTT TTATAAATGGAGATTGGGCTCC ATGACACTTTACTTGGTCTTCC TTCTTACATAGGTTTTTTGATT ACCCTTTCTCTCCTTGGTGCTT ATATACTTAAGACCCTTTAGCC AAACCCTTGCCAATGACAGTAT TTCAGTCACTAGTTCTCACTGT TTCCTCTGATCATTGAGCCTTT GGAAAAAAAATCTCACAGAGCT TATATGTAATGGGGCTTGGTTG AACAGATGACTTCCTGTAACTG CACCTCTACTTTTGGCTTCTCA AAAACAGTGGGTTGGCAGTAAT GCAGCGTGGAAGTTTTCCCATT TCTCAGTGAC |

TABLE 14

Summary of Genes involved in Glucose Metabolism

| Gene | Gene Expression Compared to Control | Role |
|---|---|---|
| Phosphorylase kinase | ↓ | Necessary for activation of glycogen synthase which stores glucose as glycogen |
| Phosphorylase | ↓ | Necessary for glycogen conversion to glucose 1-phosphate which feeds into glycolysis |
| Glycogen synthase kinase 3 | ↓ | Necessary for activation of glycogen synthase which stores glucose as glycogen |
| Calmodulin | ↓ | Necessary for activation of glycogen synthase which stores glucose as glycogen |
| Protein Kinase C | ↓ | Necessary for activation of glycogen synthase which stores glucose as glycogen |
| Protein Kinase C Binding Protein | ↓ | Necessary for activation of glycogen synthase which stores glucose as glycogen |
| Hexokinase 3 | ↓ | Necessary for glucose conversion to pyruvate to enter the TCA cycle |
| Fructose 1,6 bisphosphatase | ↓ | Necessary for glucose conversion to pyruvate to enter the TCA cycle |
| Glyceraldehyde 3-phosphate dehydrogenase | ↓ | Necessary for glucose conversion to pyruvate to enter the TCA cycle |
| Glucose 6-phosphate dehydrogenase | ↓ | Involved in pentose phosphate pathway |
| Enolase | ↓ | Necessary for glucose conversion to pyruvate to enter the TCA cycle |
| Lactate dehydrogenase | ↓ | Involved in converting private to lactate |
| Citrate lyase | ↓ | Necessary for citrate conversion to oxaloacetate which feeds acetyl-CoA into the fatty acid synthesis pathway |
| Glycerol kinase | ↓ | Necessary for changing glycerol into DHAP which feeds into glycolysis |
| Transketolase | ↓ | Involved in pentose phosphate pathway |
| Ribulose phosphate 3-epimerase | ↓ | Involved in pentose phosphate pathway |
| Ribose 5-phosphate isomerase | ↓ | Involved in pentose phosphate pathway |
| Cytochrome c oxidase polypeptide VIIa-liver/heart, mitochondrial precursor | ↓ | Associated with the production of ATP (energy source) in the electron transport chain which is associated with the TCA cycle |
| Cytochrome c oxidase subunit VIII liver form | ↓ | Associated with the production of ATP (energy source) in the electron transport chain which is associated with the TCA cycle |
| Ubiquinol-cytochrome c reductase | ↓ | Associated with the production of ATP (energy source) in the electron transport chain which is associated with the TCA cycle |
| ATP synthase | ↓ | Associated with the production of ATP (energy source) in the electron transport chain which is associated with the TCA cycle |
| NADH-ubiquinone oxidoreductase | ↓ | Associated with the production of ATP (energy source) in the electron transport chain which is associated with the TCA cycle |

TABLE 14-continued

Summary of Genes involved in Glucose Metabolism

| Gene | Gene Expression Compared to Control | Role |
|---|---|---|
| Facilitated glucose transporter/Glucose transporter-like protein-III (GLUT3) | ↓ | Involved in glucose uptake |

What is claimed is:

1. A method for improving the quality of life of a senior or super senior animal comprising feeding the animal a composition comprising:
   at least about 9% by weight protein;
   at least about 5% by weight fat; and
   at least about 0.05% by weight of at least one omega-3 polyunsaturated fatty acid.

2. The method of claim 1 wherein the method comprises feeding the animal the composition in an amount effective to improve the animal's quality of life, wherein improved quality of life is evidenced by an improvement in one or more characteristics selected from the group consisting of alertness, vitality, cartilage protection, maintenance of muscle mass, and skin and pelage quality.

3. The method of claim 1 wherein the method comprises feeding the animal the composition in an amount effective to improve alertness.

4. The method of claim 1 wherein the method comprises feeding the animal the composition in an amount effective to improve vitality.

5. The method of claim 1 wherein the method comprises feeding the animal the composition in an amount effective to protect cartilage.

6. The method of claim 1 wherein the method comprises feeding the animal the composition in an amount effective to maintain muscle mass.

7. The method of claim 1 wherein the method comprises feeding the animal the composition in an amount effective to improve skin and pelage quality.

8. The method of claim 1 wherein the animal is selected from the group consisting of a cat, a dog, and a horse.

9. A method for improving the quality of life of a senior or super senior animal comprising feeding the animal a composition comprising:
   at least one omega-3 polyunsaturated fatty acid selected from the group consisting of docosahexaenoic acid and eicosapentaenoic acid;
   at least one antioxidant; and at least one nutrient selected from the group consisting of choline, manganese, methionine, cysteine, L-carnitine, lysine, and mixtures thereof.

10. The method of claim 9 wherein the omega-3 polyunsaturated fatty acid in the composition is DHA and wherein the composition comprises at least about 0.02% by weight DHA as measured on a dry matter basis.

11. The method of claim 9 wherein the omega-3 polyunsaturated fatty acid in the composition is DHA and wherein the composition comprises from about 0.02% to about 0.40% by weight DHA as measured on a dry matter basis.

12. The method of claim 9 wherein the omega-3 polyunsaturated fatty acid in the composition comprises EPA and wherein the composition comprises at least about 0.1% by weight EPA as measured on a dry matter basis.

13. The method of claim 9 wherein the omega-3 polyunsaturated fatty acid in the composition comprises EPA, and wherein the composition comprises from about 0.1% by weight to about 1% by weight EPA as measured on a dry matter basis.

14. The method of claim 9 wherein the omega-3 polyunsaturated fatty acid in the composition comprises a mixture of DHA and EPA, and wherein the composition comprises at least about 0.02% by weight DHA and at least about 0.1% by weight EPA on a dry matter basis.

15. The method of claim 9 wherein the composition comprises one or more antioxidants selected from the group consisting of vitamin E, vitamin C, taurine, beta-carotene, carnitine, lipoic acid, and cystine.

16. The method of claim 9 wherein the composition comprises at least about 500 IU/kg vitamin E, at least about 50 ppm vitamin C and at least about 600 ppm taurine.

17. The method of claim 9 wherein the composition further comprises at least about 1000 ppm choline.

18. The method of claim 9 wherein the composition fed to the animal is an animal treat or an animal toy.

19. The method of claim 9 wherein the composition fed to the animal is a nutritional supplement.

20. A method for improving the quality of life of a senior or super senior small or regular breed canine comprising feeding the animal a composition comprising:
   from about 60% to about 70% by weight carbohydrate;
   from about 15% to about 25% by weight protein selected from the group consisting of animal protein and vegetable protein;
   from about 5% to about 7% by weight fat selected from the group consisting of animal fat and vegetable fat;
   from about 2.5% to about 4% by weight of at least one omega-3 polyunsaturated fatty acid;
   from about 1% to about 2% by weight fiber;
   from about 1% to about 2% by weight minerals; and
   from about 0.5 to about 1.5% by weight vitamins.

21. A method for improving the quality of life of a senior or super senior large breed dog, wherein the method comprises feeding the animal a composition comprising:
   from about 60% to about 70% by weight carbohydrate;
   from about 15% to about 25% by weight protein selected from the group consisting of animal protein and vegetable protein;
   from about 5% to about 7% by weight fat selected from the group consisting of animal fat and vegetable fat;
   from about 3% to about 5% by weight of at least one omega-3 polyunsaturated fatty acid;
   from about 1% to about 1.5% by weight fiber;
   from about 0.5% to about 1% by weight minerals; and from about 0.75 to about 1.25% by weight vitamins.

22. A method for improving the quality of life of a senior or super senior cat, wherein the method comprises feeding the animal a composition comprising:
   from about 30% to about 35% by weight carbohydrate;
   from about 40% to about 50% by weight protein selected from the group consisting of animal protein and vegetable protein;
   from about 12% to about 15% by weight fat selected from the group consisting of animal fat and vegetable fat;
   from about 1% to about 2% by weight of at least one omega-3 polyunsaturated fatty acid;
   from about 3% to about 5% by weight fiber;
   from about 1% to about 2% by weight minerals; and
   from about 1% to about 2% by weight vitamins.

23. The method of claim 1 wherein the method comprises feeding the animal the composition in an amount effective to improve the animal's quality of life, wherein improved quality of life is evidenced by improvement in one or more biological pathways selected from the group consisting of blood clotting and platelet activation and aggregation, bone and muscle integrity, inflammatory responses, cartilage degradation and pain response, DNA damage and repair pathways, neural function, glycogen synthesis and degradation, glycolysis, gluconeogenesis, the pentose phosphate pathway and electron transport.

24. The method of claim 1 wherein the method comprises feeding the animal the composition in an amount effective to improve the animal's quality of life, wherein improved quality of life is evidenced by a change in expression of one or more genes which encode proteins associated with or related to biological pathways selected from the group consisting of blood clotting and platelet activation and aggregation, bone and muscle integrity, inflammatory responses, cartilage degradation and pain response, DNA damage and repair pathways, neural function, glycogen synthesis and degradation, glycolysis, gluconeogenesis, the pentose phosphate pathway and electron transport.

25. A method to treat an animal suffering from a disorder or disease associated with or related to a biological pathway selected from the group consisting of blood clotting and platelet activation and aggregation, bone and muscle integrity, inflammatory responses, cartilage degradation and pain response, DNA damage and repair pathways, neural function, glycogen synthesis and degradation, glycolysis, gluconeogenesis, the pentose phosphate pathway and electron transport comprising administering to said animal a super senior pet food composition.

26. The method of claim 25 wherein said super senior pet food composition comprises at least about 9% by weight protein, at least about 5% by weight fat, and at least about 0.05% by weight of at least one omega-3 polyunsaturated fatty acid.

27. The method of claim 25 wherein said super senior pet food composition further comprises at least one omega-3 polyunsaturated fatty acid selected from the group consisting of docosahexaenoic acid ("DHA") and eicosapentaenoic acid ("EPA").

28. The method of claim 25 wherein said super senior pet food composition further comprises at least one antioxidant and at least one nutrient selected from the group consisting of choline, manganese, methionine, cysteine, L-carnitine, lysine, and mixtures thereof.

29. The method of claim 25 wherein said super senior pet food composition comprises the components disclosed in Table 1 or Table 1A.

30. A method to treat an animal suffering from a disorder or disease associated with or related to a biological pathway selected from the group consisting of blood clotting and platelet activation and aggregation, bone and muscle integrity, inflammatory responses, cartilage degradation and pain response, DNA damage and repair pathways, neural function, glycogen synthesis and degradation, glycolysis, gluconeogenesis, the pentose phosphate pathway and electron transport comprising modulating the expression level of one or more genes listed on Tables 5-14 in said animal in order to mimic the pattern of expression seen in vivo after administration of a super senior pet food composition.

31. The method of claim 30 wherein said super senior pet food composition comprises the components disclosed in Table 1 or Table 1A.

32. The method of claim 23 wherein said animal is selected from a group consisting of a senior or super senior large breed canine, regular breed canine, small breed canine or feline.

* * * * *